United States Patent
Mercken et al.

(10) Patent No.: US 11,365,244 B2
(45) Date of Patent: *Jun. 21, 2022

(54) ANTI-PHF-TAU ANTIBODIES AND USES THEREOF

(71) Applicant: Janssen Biotech, Inc., Horsham, PA (US)

(72) Inventors: Marc Mercken, Turnhout (BE); Thomas Malia, Philadelphia, PA (US); Marianne Borgers, Balen (BE); Kristof Van Kolen, Haacht (BE)

(73) Assignee: Janssen Biotech, Inc., Horsham, PA (US)

( * ) Notice: Subject to any disclaimer, the term of this patent is extended or adjusted under 35 U.S.C. 154(b) by 21 days.

This patent is subject to a terminal disclaimer.

(21) Appl. No.: 16/986,615

(22) Filed: Aug. 6, 2020

(65) Prior Publication Data

US 2021/0179696 A1  Jun. 17, 2021

Related U.S. Application Data

(63) Continuation of application No. 15/923,011, filed on Mar. 16, 2018, now Pat. No. 10,766,953.

(60) Provisional application No. 62/472,214, filed on Mar. 16, 2017.

(51) Int. Cl.
| | |
|---|---|
| *C07K 16/18* | (2006.01) |
| *A61P 25/28* | (2006.01) |
| *G01N 33/68* | (2006.01) |
| *A61K 9/00* | (2006.01) |
| *C07K 16/44* | (2006.01) |
| *A61K 39/00* | (2006.01) |

(52) U.S. Cl.
CPC ............ *C07K 16/18* (2013.01); *A61K 9/0019* (2013.01); *A61P 25/28* (2018.01); *C07K 16/44* (2013.01); *G01N 33/6896* (2013.01); *A61K 2039/505* (2013.01); *A61K 2039/54* (2013.01); *C07K 2317/24* (2013.01); *C07K 2317/30* (2013.01); *C07K 2317/34* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/92* (2013.01); *G01N 2800/2821* (2013.01); *G01N 2800/7047* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,225,539 A | 7/1993 | Winter | |
| 7,657,380 B2 | 2/2010 | Lazar et al. | |
| 9,221,902 B2 | 12/2015 | Smider | |
| 10,196,440 B2 | 2/2019 | Alderfer et al. | |
| 2003/0138972 A1 | 7/2003 | Vandermeeren et al. | |
| 2005/0288491 A1 | 12/2005 | Wilson et al. | |
| 2006/0140932 A1 | 6/2006 | Dickinson et al. | |
| 2007/0048785 A1 | 3/2007 | Lin et al. | |
| 2009/0142261 A1 | 6/2009 | Hsu et al. | |
| 2009/0169547 A1 | 7/2009 | Sahin et al. | |
| 2010/0261620 A1 | 10/2010 | Almagro et al. | |
| 2011/0059093 A1 | 3/2011 | Bohrmann et al. | |
| 2011/0077224 A1 | 3/2011 | Pandey et al. | |
| 2011/0092372 A1 | 4/2011 | Almagro et al. | |
| 2011/0118299 A1 | 5/2011 | Lovell et al. | |
| 2011/0143443 A9 | 6/2011 | Mercken et al. | |
| 2011/0256154 A1 | 10/2011 | Vincent et al. | |
| 2012/0058906 A1 | 3/2012 | Smider et al. | |
| 2012/0087861 A1 | 4/2012 | Nitsch et al. | |
| 2012/0276009 A1 | 11/2012 | Pfeifer et al. | |
| 2015/0307600 A1 | 10/2015 | Alderfer et al. | |

FOREIGN PATENT DOCUMENTS

| | | |
|---|---|---|
| WO | 1992/01047 A1 | 1/1992 |
| WO | 1993/08302 A1 | 4/1993 |
| WO | 1995/17429 A1 | 6/1995 |
| WO | 1996/04309 A1 | 2/1996 |
| WO | 2004/006955 A1 | 1/2004 |
| WO | 2009/017161 A1 | 2/2009 |
| WO | 2010/144711 A2 | 12/2010 |

OTHER PUBLICATIONS

Reitz "Toward precision medicine in Alzheimer's disease" Ann Transl Med 2016;4(6):107 (Year: 2016).*
Stanford "Alzheimer's Prevention, Treatment and Research—A Q&A with Dr. Frank Longo" accessed from stanfordhealthcare.org on May 3, 2016 (Year: 2016).*
Abhinandan, et al., Analysis and improvements to Kabat and Structurally Correct Numbering of antibody Variable domains., Molelcular immunology, Jul. 9, 2008, pp. 3832-3839, vol. 45.
Adams, et al., PHENIX: a comprehensive Python-based system for macromolecular structure solution., Acta Crystallographica Section D Biological Crystallography, 2010, pp. 213-221, vol. D66 Issue part 2.
Allen, et al., Abundant Tau Filaments and Nonapoptoic Neurodegenration in Transgenic Mice Expressing Human P301S Tau Protien., The Journal of Neuroscience., Nov. 1, 2002, pp. 9340-9351, vol. 22 Issue 21.
Asuni, et al., Imnlunotherapy Targeting Pathological Tau Conformers in a Tangle Mouse Model Reduces Brain Pathology with Associated Functional Improvements, The Journal of Neuroscience, Aug. 22, 2007, pp. 9115-9129, vol. 27 Issue 34.

(Continued)

*Primary Examiner* — Adam Weidner
(74) *Attorney, Agent, or Firm* — Grimes & Yvon LLP

(57) ABSTRACT

Monoclonal anti-PHF-tau antibodies and antigen-binding fragments thereof are described. Also described are nucleic acids encoding the antibodies, compositions comprising the antibodies, methods of producing the antibodies and using the antibodies for treating or preventing conditions such as tauopathies.

14 Claims, 27 Drawing Sheets

Specification includes a Sequence Listing.

(56) References Cited

OTHER PUBLICATIONS

Boutajangout, et al., Immunotherapy Targeting Pathological Tau Prevents Cognitive Decline in a New Tangle Mouse Model, The Journal of Neuroscience, Dec. 8, 2010, pp. 16559-16566, vol. 30 Issue 49.

Boutajangout, et al., Passive immunization targeting pathological phospho-tau protein in a mouse model reduces functional decline and clears tau aggregates from the brain, Journal of Neurochemistry, Jun. 1, 2011, pp. 658-667, vol. 118.

Brion, et al., Neurofilament Monoclonal Antibodies RT97 and 8D8 Recognize Different Modified Epitopes in Paired Helical Filament—? In Alzheimer's Disease, Journal of Neurochemistry, 1993, pp. 1372-1382, vol. 60 Issue 4.

Brunden, et al., Advances in tau-focused drug discovery for Alzheimer's disease and related tauopathies, Nature Reviews | Drug Discovery, 2009, pp. 783-793, vol. 8.

Butner, et al., Tau Protein Binds to Microtubules through A Flexible Array of Distributed Weak Sites., The Journal of Cell Biology, Nov. 1, 1991, pp. 717-730, vol. 115 Issue 3.

Chai, et al., Passive Immunization with Anti-Tau Antibodies in Two Transgenic Models Reduction of Tau Pathology and Delay of Disease Progression, Journal of Biological Chemistry, Sep. 30, 2011, pp. 34457-34467, vol. 286 Issue 39.

Chen, et al., Enhancement and destruction of antibody function by somatic mutation: unequal occurrence is controlled by V gene combinatorial associations, The EMBO Journal., 1995, pp. 2784-2794, vol. 14 Issue 12.

Chothia, et al., Canonical Structures for the Hypervariable Regions of Immunoglobulins, J. Mol. Biol.., Apr. 23, 1987, pp. 901-917, vol. 196.

Christiane Reitz, Toward precision medicine in Alzheimer's disease, Annals of Translational Medicine, 2016, pp. 1-7, vol. 4 Issue 6.

Clavaguera, et al., Brain homogenates from human tauopathies induce tau inclusions in mouse brain., Proc Natl Acad Sci, Jun. 4, 2013, pp. 9535-9540, vol. 110 Issue 23.

Clavaguera, et al., Transmission and spreading of tauopathy in transgenic mouse brain, Nature Cell Biology, Jun. 7, 2009, pp. 909-913, vol. 11 Issue 7.

Collaborative Computational Projecj., The CCP4 Suite: Programs for Protein Crystallography., Acta Crystallographica Section D Biological Crystallography, Mar. 21, 1994, pp. 760-763, vol. D50 Issue part 5.

Collin, et al., Neuronal uptake of tau/pS422 antibody and reduced progression of tau pathology in a mouse model of Alzheimers disease., Brain., Jul. 31, 2014, pp. 2834-2846, vol. 137 Issue 10.

Condamines, et al., New immunoassay for the mapping of neurofibrillary degeneration in Alzheimer's disease using two monoclonal antibodies against human paired helical filament tau proteins, Neuroscience Letters, May 5, 1995, pp. 81-84, vol. 192 Issue 2.

Decalignon, et al., Propagation of Tau Pathology in a Model of Early Alzheimer's Disease., Neuron, Feb. 23, 2012, pp. 685-697, vol. 73 Issue 4.

Dennis W. Dickson., Neuropathology of progressive supranuclear palsy., Handbook of Clinical Neurology, 2008, pp. 487-491, vol. 89.

Eduardo A. Padlan, A Possible Procedure for Reducing the Immunogenicity of Antibody Variable Domains While Preserving Theirligand-Binding Properties, Molecular Immunology, 1991, pp. 489-498, vol. 28 Issue 4/5.

Emsley, et al., Coot: model-building tools for molecular graphics., Acta Crystallographica Section D Biological Crystallography, Aug. 4, 2004, pp. 2126-2132, vol. D60.

Fishwild, et al., High-avidity human IgGK monoclonal antibodies from a novel strain of minilocus transgenic mice, Nature Biotechnology, May 1, 1996, pp. 845-851, vol. 14.

Foote, et al., Antibody framework residues affecting the conformation of the hypervariable loops, Journal of Molecular Biology, Mar. 20, 1992, pp. 487-499, vol. 224 Issue 2.

Frank Longo, Stanford Alzheimer's Prevention, Treatment and Research—A Q&A with Dr. Frank Longo, stanfordhealthcare.org, May 3, 2016, pp. 1-2, Page Number.

Fransson, et al., Human Framework Adaptation of a Mouse Anti-Human IL-13 Antibody., J. Mol. Biol., Mar. 10, 2010, pp. 214-231, vol. 398 Issue 2.

Frost, et al., Propagation of Tau Misfolding from the Outside to the Inside of a Cell, The Journal of Biological Chemistry, May 8, 2009, pp. 12845-12852, vol. 284 Issue 19.

Funk, et al., Distinct Therapeutic Mechanisms of Tau Antibodies Promoting Microglial Clearance Versus Blocking Neuronal Uptake., The Journal of Biological Chemistry, Aug. 28, 2015, pp. 21652-21662, vol. 290 Issue 35.

Goedert, et al., Epitope mapping of monoclonal antibodies to the paired helical filaments of Alzheimer's disease identification of phosphorylation sites in tau protein., Biochemical Journal., Aug. 1, 1994, pp. 871-877, vol. 301 Issue part 3.

Goedert, et al., Epitope Mapping of Monoclonal Antibodies to the Paired Helical Filaments of Alzheimer's Disease:Identification of Phosphorylationsites in Tau Protein, Biochemical Journal, Aug. 1, 1994, pp. 871-877, vol. 301 Issue part 03.

Greenberg, et al., A preparation of Alzheimer paired helical filaments that displays distinct T proteins by polyacrylamide gel electrophoresis, Proc. Natl. Acad. Sci, Apr. 27, 1990, pp. 5827-5831, vol. 87.

Han, et al., Beta amyloid, tau, neuroimaging, and cognition: sequence modeling of biomarkers for Alzheimer's Disease., Brain Imaging and Behavior, May 31, 2012, pp. 610-620, vol. 6 Issue 4.

Hanger, et al., Tau phosphorylation: the therapeutic challenge for neurodegenerative disease, Cell Press, Feb. 24, 2009, pp. 112-119, vol. 15 Issue 3.

Hasegawa, et al., Characterization of MAB AP422, A Novel Phosphorylation-Dependent Monoclonal Antibody Against Tau Protein, FEBS Letters, Elsevier, Amsterdam, NL., Mar. 1, 1996, pp. 25-30, vol. 384.

Hasegawa, et al., Characterization of Two Distinct Monocolonal Antibodies to Paired Helical Filaments: Further Evidence for Fetal-Type Phosphorylation of the? In Paired Helical Filaments, Journal of Neurochemistry, Jun. 1, 1993, pp. 2068-2077, vol. 60 Issue 6.

Hoffmann, et al., Unique Alzheimer's disease paired helical filament specific epitopes involve double phosphorylation at specific sites, Biochemistry., Jul. 1, 1997, pp. 8114-8124, vol. 36 Issue 26.

Holmes, et al., Proteopathic tau seeding predicts tauopathy in vivo., Proc Natl Acad Sci, Sep. 26, 2014, pp. E4376-E4385, vol. 111 Issue 41.

Iba, et al., Synthetic Tau Fibrils Mediate Transmission of Neurofibrillary Tangles in a Transgenic Mouse Model of Alzheimer's-Like Tauopathy., The Journal of Neuroscience, Jan. 16, 2013, pp. 1024-1037, vol. 33 Issue 3.

Iba, et al., Tau pathology spread in PS19 tau transgenic mice following locus coeruleus (LC) injections of synthetic tau fibrils is determined by the LC's afferent and efferent connections., Acta Neuropathol., Jul. 7, 2015, pp. 349-362, vol. 130 Issue 3.

Jicha, et al., A conformation-and phosphorylation-dependent antibody recognizing the paired helical filaments of Alzheimer's disease, Journal of Neurochemistry, 1997, pp. 2087-2095, vol. 69 Issue 5.

Juan C. Almagro., Identification of differences in the specificity-determining residues of antibodies that recognize antigens of different size: implications for the rational design of antibody repertoires, Journal of Yiolecular Recognition, Dec. 17, 2003, pp. 132-143, vol. 17.

Julien, et al., Biochemical Isolation of Insoluble Tau in Transgenic Mouse Models of Tauopathies., Methods in Molecular Biology, 2012, pp. 473-491, vol. 849.

Knappik, et al., Fully Synthetic Human Combinatorial Antibody Libraries (HuCAL) Based on Modular Consensus Frameworks and CDRs Randomized with Trinucleotides, J. Mol. Biol., 2000, pp. 57-86, vol. 296.

Knight, et al., Pharmacodynamic enhancement of the anti-platelet antibody Fab abciximab by site-specific pegylation, Platelets, 2004, pp. 409-418, vol. 15 Issue 7.

(56) References Cited

OTHER PUBLICATIONS

Koenig, et al., Mutational landscape of antibody variable domains reveals a switch modulating the interdomain conformational dynamics and antigen binding, PNAS, 2016, pp. E486-E495, Page Number.
Kohler, et al., Continuous cultures of fused cells secreting antibody of predefined specificity, Nature, Aug. 7, 1975, pp. 495-497, vol. 256.
Krebs, et al., High-throughput generation and engineering of recombinant human antibodies, Journal of Immunological Methods, Apr. 6, 2001, pp. 67-84, vol. 254.
Kussie, et al., A Single Engineered Amino Acid Substitution Changes Antibody Fine Specificity, Journal of Immunology, 1994, pp. 146-152, vol. 152 Issue 1.
Lee, et al., Antibody-Mediated Targeting of Tau In Vivo Does Not Require Effector Function and Microglial Engagement, Cell Reports, Aug. 9, 2016, pp. 1690-1700, vol. 16 Issue 6.
Lefranc, et al., IMGT unique numbering for immunoglobulin and T cell receptor variable domains and Ig superfamily V-like domains, Developmental and Comparative Immunology, May 29, 2002, pp. 55-77, vol. 27.
Leong, et al., Adapting Pharmacokinetic Properties of a Humanized Anti-Interleukin-8 Antibody for Therapeutic Applications Using Site-Specific Pegylation, Cytokine, 2001, pp. 106-119, vol. 16 Issue 3.
Li, et al., Characterization of Two VQIXXK Motifs for Tau Fibrilization in Vitro., Bio chemistry, Dec. 19, 2006, pp. 15692-15701, vol. 45 Issue 51.
Lonberg, et al., Antigen-specific human antibodies from mice comprising four distinct genetic modifications, Nature, Apr. 28, 1994, pp. 856-859, vol. 368.
Martin, et al., Structural Families in Loops of Homologous Proteins: Automatic Classification, Modelling and Application to Antibodies., J. Mol. Biol., Aug. 29, 1996, pp. 800-815, vol. 263 Issue 5.
Matsuo, et al., Biopsy-Derived Adult Human Brain Tau Is Phosphorylated at Many of the Same Sites as Alzheimer's Disease Paired Helical Filament Tau., Neuron., 1994, pp. 989-1002, vol. 13 Issue 4.
McCoy, et al., Phaser crystallographic software., Journal of Applied Crystallography, Apr. 27, 2007, pp. 658-674, vol. 40 Issue part 4.
McEwan, et al., Cytosolic Fc receptor TRIM21 inhibits seeded tau aggregation., PNAS., Jan. 17, 2017, pp. 574-579, vol. 114 Issue 3.
Mendez, et al., Functional transplant of megabase human immunoglobulin loci recapitulates human antibody response in mice, nature genetics, 1997, pp. 146-156, vol. 15.
Mercken, et al., Affinity Purification of Human T Proteins and the Construction of a Sensitive Sandwich Enzyme-Linked Immunosorbent Assay for Hllman T Detection, J. Neurochem., Jun. 25, 1991, pp. 548-553, vol. 58.
Mercken, et al., Monoclonal antibodies with selective specificity for Alzheimer Tau are directed against phosphatase-sensitive epitopes, Acta Neuropathol, Mar. 17, 1992, pp. 265-272, vol. 84.
Mocanu, et al., The Potential for B-Structure in the Repeat Domain of Tau Protein Determines Aggregation, Synaptic Decay, Neuronal Loss, and Coassembly Wth Endogenous Tau in inducible Mouse Models of Tauopathy., The Journal of Neuroscience, Jan. 16, 2008, pp. 737-748, vol. 28 Issue 3.
Morris, et al., Tau post-translational modifications in wild-type and human amyloid precursor protein transgenic mice, Nature Neuroscience, Jul. 20, 2015, pp. 1183-1189, vol. 18 Issue 8.
Morris, et al., The Many Faces of Tau, Neuron, May 12, 2011, pp. 410-426, vol. 70.
Murshudov, et al., Refinement of Macromolecular Structures by the Maximum-Likelihood Method., Acta Crystallographica Section D Biological Crystallography, 1997, pp. 240-255, vol. D53.
Oddo, et al., Genetically augmenting tau levels does not modulate the onset or progression of Ab pathology in transgenic mice., Journal of Neurochemistry, Mar. 7, 2007, pp. 1053-1063, vol. 102.

Otvos, et al., Rapid Communication Monoclonal Antibody PHF-1 Recognizes Tau Protein Phosphorylated at Serine Residues 396 and 404., Journal of Neuroscience Research, Sep. 28, 1994, pp. 669-673, vol. 39.
Peeraer, et al., Intracerebral injection of preformed synthetic tau fibrils initiates widespread tauopathy and neuronal loss in the brains of tau transgenic mice., Neurobiology of Disease, 2015, pp. 83-95, vol. 73.
Petry, et al., Specificity of Anti-Tau Antibodies when Analyzing Mice Models of Alzheimer's Disease: Problems and Solutions, PLOS ONE, May 2, 2014, pp. e94251-, vol. 9 Issue 5.
Porzig, et al., Epitope mapping of mAbs AT8 and Tau5 directed against hyperphosphorylated regions of the human tau protein, Biochemical and Biophysical Research Communications, Jun. 29, 2007, pp. 644-649, vol. 358 Issue 2.
Queen, et al., A humanized antibody that binds to the interleukin 2 receptor, Proc. Natl. Acad. Sci., Aug. 30, 1989, pp. 10029-10033, vol. 86.
Sanders, et al., Distinct Tau Prion Strains Propagate in Cells and Mice and Define Different Tauopathies, Neuron., Jun. 18, 2014, pp. 1271-1288, vol. 82.
Scattoni, et al., Early behavioural markers of disease in P301S tau transgenic mice., Behavioural Brain Research, 2010, pp. 250-257, vol. 208.
Schroeder, et al., Tau-Directed Immunotherapy: A Promising Strategy for Treating Alzheimer's Disease and Other Tauopathies., J Neuroimmune Pharmacol, 2016, pp. 9-25, vol. 11 Issue 1.
Seubert, et al., Detection of Phosphorylated Ser262 in Fetal Tau, Adult Tau, and Paired Helical Filament Tau., The Journal of Biological Chemistry, May 12, 1995, pp. 18917-18922, vol. 270 Issue 32.
Shi, et al., De Novo Selection of High-Affinity Antibodies from Synthetic Fab Libraries Displayed on Phage as pIX Fusion Proteins, J. Mol. Biol., Jan. 28, 2010, pp. 385-396, vol. 397 Issue 2.
Singer, et al., Neighbored phosphorylation sites as PHF-tau specific markers in Alzheimer's disease, Biochemical and Biophysical Research Communications, Aug. 4, 2006, pp. 819-828, vol. 346 Issue 3.
Spillantini, et al., Tau protein pathology in neurodegenerative diseases, Trends Neurosci, 1998, pp. 428-433, vol. 21 Issue 10.
Stokes, et al., Stable Isotopes of Lithium: In Vivo Differential Distribution Between Plasma and cerabrospinal Fluid ., Biological psychiatry, 1982, pp. 413-421, vol. 17 Issue 4.
Terwel, et al., Changed Conformation of Mutant Tau-P301L Underlies the Moribund Tauopathy, Absent in Progressive, Nonlethal Axonopathy of Tau-4R/2N Transgenic Mice., The Journal of Biological Chemistry, 2005, pp. 3963-3973, vol. 280 Issue 5.
William R Strohl., Optimization of Fc-mediated effector functions of monoclonal antibodies, Current Opinion in Biotechnology, Nov. 4, 2009, pp. 685-691, vol. 20.
Wischik, et al., "Structural characterization of the core of the paired helical filament of Alzheimer disease", Proc. Natl. Acad. Sci. USA, vol. 85; pp. 4884-4888 (Jul. 1988).
Wolfgang Kabsch., XDS., Acta Crystallographica Section D Biological Crystallography, 2010, pp. 125-132, vol. D66 part 2.
Wu, et al., An Analysis of the Sequences of the Variable Regions of Bence Jones Proteins and Myeloma Light Chains and Their Implications for Antibody Complementarity., Bence Jones Proteinsand Myeloma Light Chains, Aug. 1, 1970, pp. 211-250, Page number.
Wu, et al., An Analysis of the Sequences of the Variable Regions of Bence Jones Proteins and Myeloma Light Chainsand Their Implications for Antibody Complementarity*, Bence Jones Proteinsand Myeloma Light Chains, Mar. 26, 1970, pp. 211-250, Page Number.
Yang, et al., Tailoring structure-function and pharmacokinetic properties of single-chain Fv proteins by site-specific PEGylation, Protein Engineering, 2003, pp. 761-770, vol. 16 Issue 10.
Yoshiyama, et al., Synapse Loss and Microglial Activation Precede Tangles in a P301S Tauopathy Mouse Model ., Neuron, Feb. 1, 2007, pp. 337-351, vol. 53 Issue 3.
Zhao, et al., Two routes for production and purification of Fab fragments in biopharmaceutical discovery research: Papain diges-

(56) References Cited

OTHER PUBLICATIONS tion of mAb and transient expression in mammalian cells., Protein Expression and Purification, May 12, 2009, pp. 182-189, vol. 67 Issue 2.

* cited by examiner

FIG. 2

| AT8 | | AT100 | | HT7 | | BT2 | | PT3 | |
|---|---|---|---|---|---|---|---|---|---|
| NT | PT | NT | PT | NT | PT | NT | PT | NT | PT |

FIG. 3A
FIG. 3B
FIG. 3C
FIG. 3D
FIG. 3E
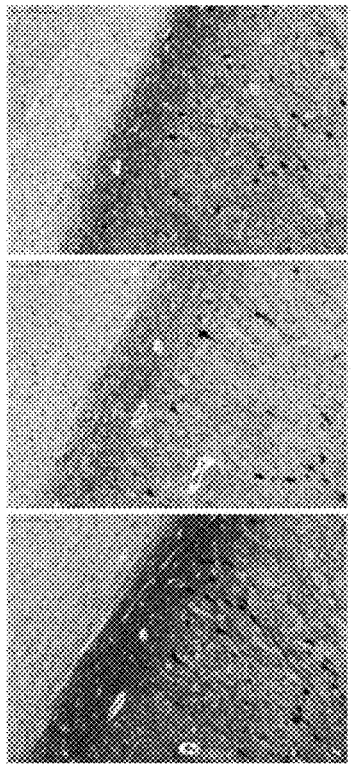
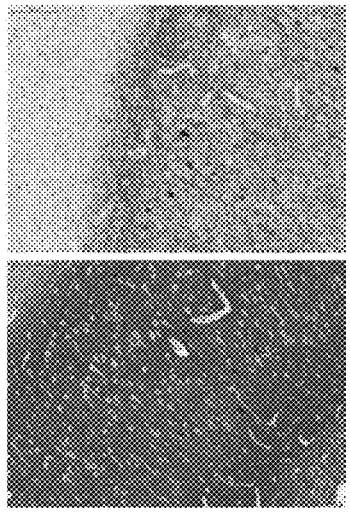

FIG. 5A
FIG. 5B
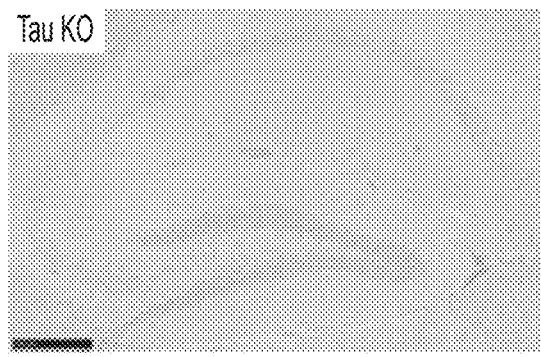
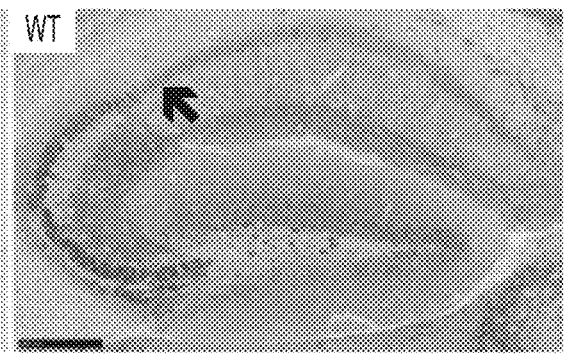

FIG. 10

```
VH         10         20         30         40         50         60         70         80         90        100       110
VH10  EVKLVESGGDLVKPGGSLKLSCAASGFTFSSYAMSWVRQNPEKRLEWVASISKGGNTYYPNSVKGRFTISRDNARNILYLQMSSLRSEDTALYYCARGWGDYGWFAYWGQVTLVTVSA
VH91  EVQLLESGGGLVQPGGSLRLSCAASGFTFSSYAMSWVRQAPGKGLEWVASISKGGNTYYADSVKGRFTISRDNSKNTLYLQMNSLRAEDTAVYYCAKGWGDYGWFAYWGQVTLVTVSS
VH92  QVQLVESGGGVVQPGRSLRLSCAASGFTFSSYAMSWVRQAPGKGLEWVSSISKGGNTYYADSVKGRFTISRDNSKNTLYLQMNSLRAEDTAVYYCARGWGDYGWFAYWGQVTLVTVSS
VH93  QVQLVESGGGLVKPGGSLRLSCAASGFTFSSYAMSWVRQAPGKGLEWVSSISKGGNTYYADSVKGRFTISRDNAKNSLYLQMNSLRAEDTAVYYCARGWGDYGWFAYWGQVTLVTVSS
VH94  QVQLVQSGAEVKKPGASVKVSCKASGFTFSSYAMSWVRQAPGQRLEMMGSISKGGNTYYSQKFQGRVTITRDTSASTAYMELSSLRSEDTAVYYCARGWGDYGWFAYWGQVTLVTVSS

VL         10         20         30         40         50         60         70         80         90        100
VL7   DIKMTQSPSSMYASLGERVTITCKASQDINRYLNWFQQKPGKSPKTLIYRANRLLDGVPSRFSGSGSGQDYSLTISSLDYEDMGIYYCLQYDEFPLTFGDGTKLELK
VL77  DIQMTQSPSSLSASVGDRVTITCKASQDINRYLNWFQQKPGKAPKSLIYRANRLLDGVPSRFSGSGSGTDFTLTISSLQPEDFATYYCLQYDEFPLTFGQGTKLEIK
VL92  DIQMTQSPSSLSASVGDRVTITCKASQDINRYLNWFQQKPGKAPKSLIYRANRLLDGVPSRFSGSGSGTDFTLTISSLQPEDFATYYCLQYDEFPLTFGQGTKLEIK
VL78  DIQMTQSPSSLSASVGDRVTITCKASQDINRYLNWFQQKPGKAPKSLIYRANRLLSGVPSRFSGSGSGTDFTLTISSLQPEDFATYYCLQYDEFPLTFGQGTKLEIK
VL79  DIQMTQSPSSLSASVGDRVTITCKASQDINRYLNWYQQKPGKAPKLLIYRANRLLDGVPSRFSGSGSGTDFTLTISSLQPEDFATYYCLQYDEFPLTFGQGTKLEIK
VL80  DIVMTQTPLSSPVTLGQPASISCKASQDINRYLNWLQRPGQPPRLLIYRANRLLDGVPDRFSGSGAGTDFTLKISRVEAEDVGVYYCLQYDEFPLTFGQGTKLEIK
```

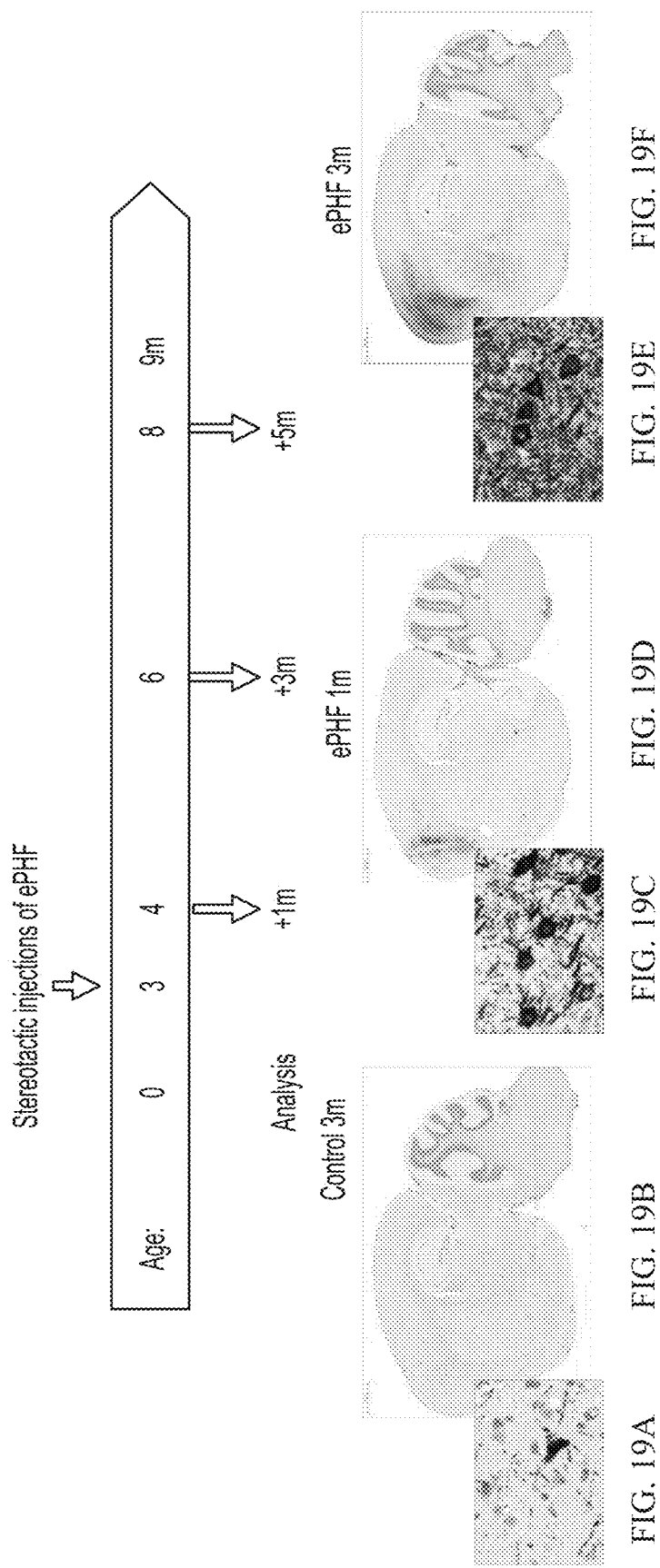

FIG. 22A
| Group | Co-injection | IP (20 mg/kg, 2x/week) | n |
|---|---|---|---|
| 1 | IgG1 | IgG1 | 19 |
| 2 | PT3(G1) | PT3(G1) | 16 |
| 3 | PT3(G2a) | PT3(G2a) | 18 |
| 4 | PT3(G2a-HFA) | PT3(G2a-HFA) | 15 |
| Inject | Amount | Total volume (µL) | Concentration (µM) |
|---|---|---|---|
| 2.5 µL ePHF | 1 pmole Tau | 5 | 0.2 |
| 2.5 mL antibody | 25 pmole ab | 5 | 5 |
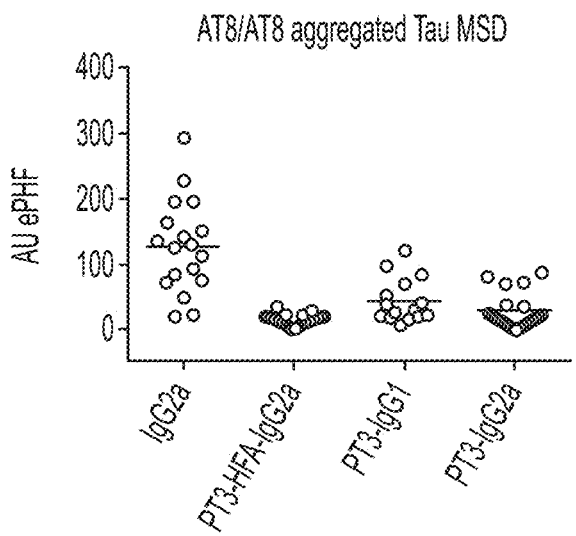
FIG. 22B
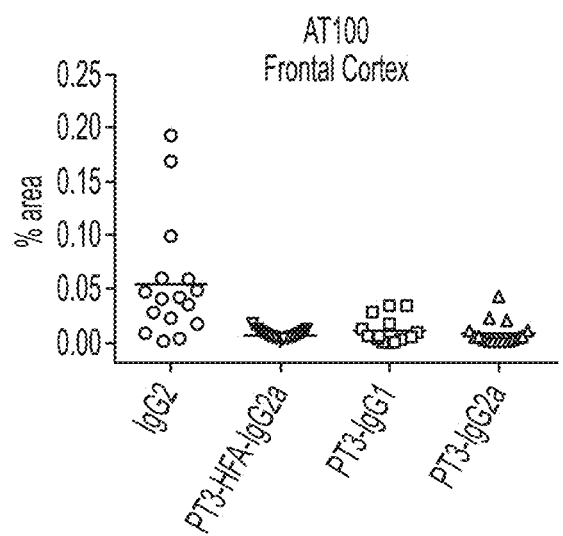
FIG. 22C

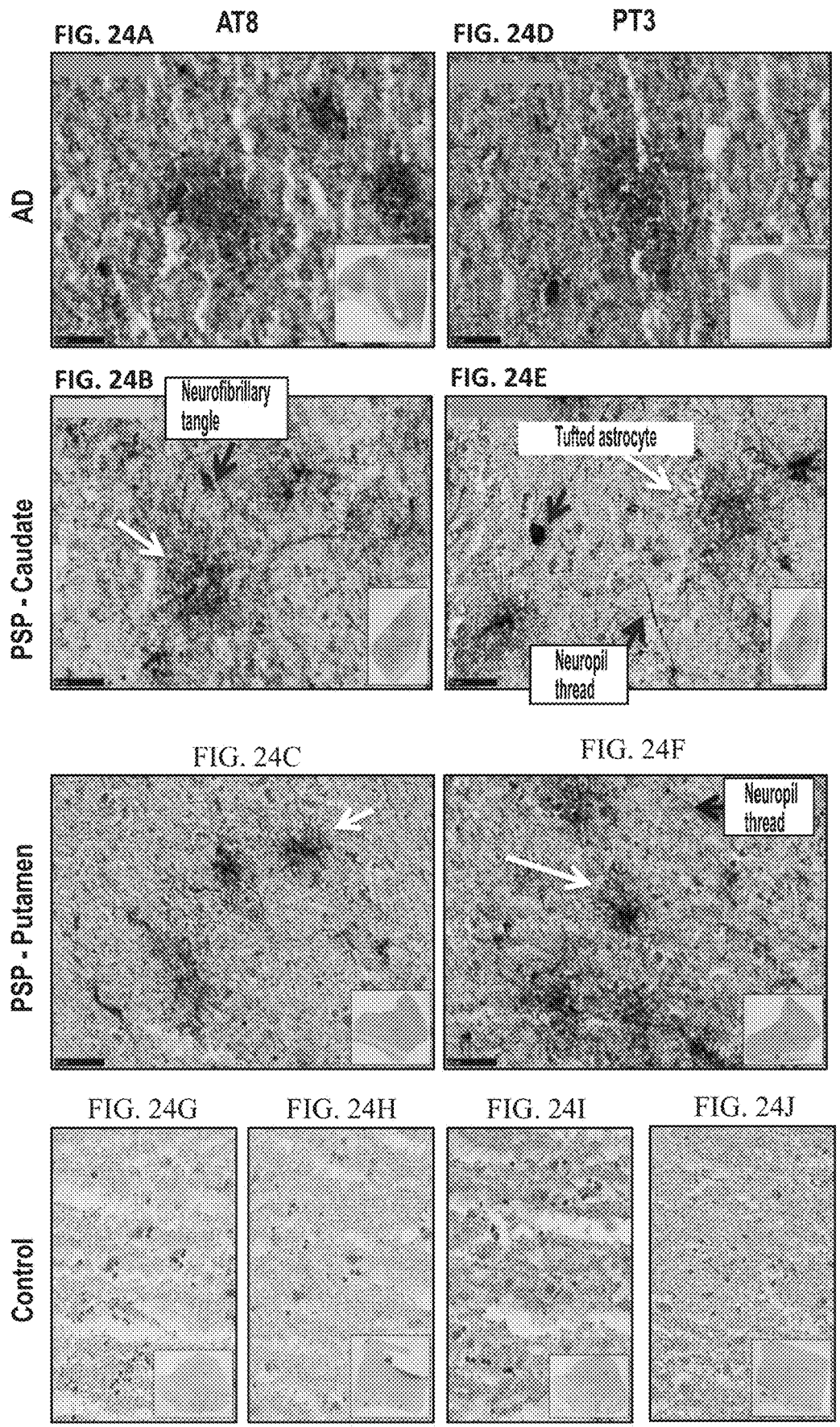

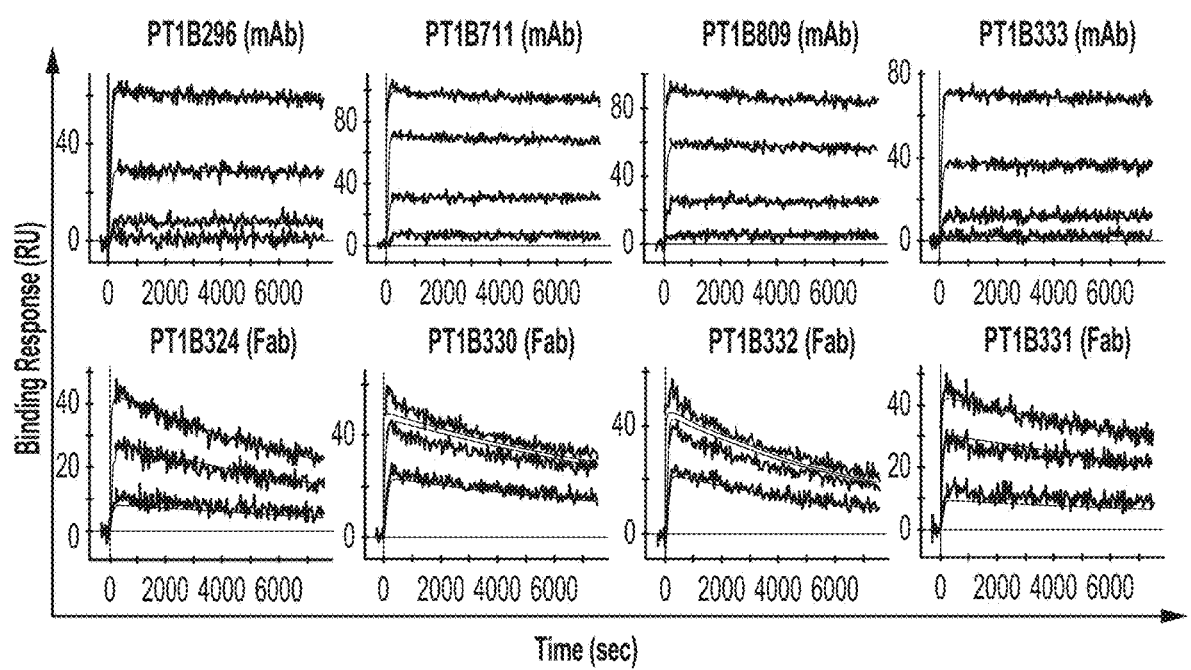

SEQUENCE LISTING

```
<160> NUMBER OF SEQ ID NOS: 81

<210> SEQ ID NO 1
<211> LENGTH: 7
<212> TYPE: PRT
<213> ORGANISM: Mus musculus

<400> SEQUENCE: 1

Gly Phe Thr Phe Ser Ser Tyr
1               5

<210> SEQ ID NO 2
<211> LENGTH: 5
<212> TYPE: PRT
<213> ORGANISM: Mus musculus

<400> SEQUENCE: 2

Ser Lys Gly Gly Asn
1               5

<210> SEQ ID NO 3
<211> LENGTH: 10
<212> TYPE: PRT
<213> ORGANISM: Mus musculus

<400> SEQUENCE: 3

Gly Trp Gly Asp Tyr Gly Trp Phe Ala Tyr
1               5                   10

<210> SEQ ID NO 4
<211> LENGTH: 10
<212> TYPE: PRT
<213> ORGANISM: Mus musculus

<400> SEQUENCE: 4

Gly Phe Thr Phe Ser Ser Tyr Ala Met Ser
1               5                   10

<210> SEQ ID NO 5
<211> LENGTH: 9
<212> TYPE: PRT
<213> ORGANISM: Mus musculus

<400> SEQUENCE: 5

Ser Ile Ser Lys Gly Gly Asn Thr Tyr
1               5

<210> SEQ ID NO 6
<211> LENGTH: 10
<212> TYPE: PRT
<213> ORGANISM: Mus musculus
```

```
<400> SEQUENCE: 6

Gly Trp Gly Asp Tyr Gly Trp Phe Ala Tyr
1               5                   10

<210> SEQ ID NO 7
<211> LENGTH: 5
<212> TYPE: PRT
<213> ORGANISM: Mus musculus

<400> SEQUENCE: 7

Ser Tyr Ala Met Ser
1               5

<210> SEQ ID NO 8
<211> LENGTH: 16
<212> TYPE: PRT
<213> ORGANISM: Mus musculus

<400> SEQUENCE: 8

Ser Ile Ser Lys Gly Gly Asn Thr Tyr Tyr Ala Asp Ser Val Lys Gly
1               5                   10                  15

<210> SEQ ID NO 9
<211> LENGTH: 10
<212> TYPE: PRT
<213> ORGANISM: Mus musculus

<400> SEQUENCE: 9

Gly Trp Gly Asp Tyr Gly Trp Phe Ala Tyr
1               5                   10

<210> SEQ ID NO 10
<211> LENGTH: 8
<212> TYPE: PRT
<213> ORGANISM: Mus musculus

<400> SEQUENCE: 10

Gly Phe Thr Phe Ser Ser Tyr Ala
1               5

<210> SEQ ID NO 11
<211> LENGTH: 7
<212> TYPE: PRT
<213> ORGANISM: Mus musculus

<400> SEQUENCE: 11

Ile Ser Lys Gly Gly Asn Thr
1               5

<210> SEQ ID NO 12
<211> LENGTH: 13
<212> TYPE: PRT
<213> ORGANISM: Mus musculus

<400> SEQUENCE: 12

Ala Arg Gly Trp Gly Asp Tyr Gly Trp Phe Ala Tyr Trp
1               5                   10

<210> SEQ ID NO 13
<211> LENGTH: 11
<212> TYPE: PRT
<213> ORGANISM: Mus musculus

<400> SEQUENCE: 13
```

Lys Ala Ser Gln Asp Ile Asn Arg Tyr Leu Asn
1               5                   10

<210> SEQ ID NO 14
<211> LENGTH: 7
<212> TYPE: PRT
<213> ORGANISM: Mus musculus

<400> SEQUENCE: 14

Arg Ala Asn Arg Leu Leu Asp
1               5

<210> SEQ ID NO 15
<211> LENGTH: 9
<212> TYPE: PRT
<213> ORGANISM: Mus musculus

<400> SEQUENCE: 15

Leu Gln Tyr Asp Glu Phe Pro Leu Thr
1               5

<210> SEQ ID NO 16
<211> LENGTH: 11
<212> TYPE: PRT
<213> ORGANISM: Mus musculus

<400> SEQUENCE: 16

Lys Ala Ser Gln Asp Ile Asn Arg Tyr Leu Asn
1               5                   10

<210> SEQ ID NO 17
<211> LENGTH: 7
<212> TYPE: PRT
<213> ORGANISM: Mus musculus

<400> SEQUENCE: 17

Arg Ala Asn Arg Leu Leu Asp
1               5

<210> SEQ ID NO 18
<211> LENGTH: 9
<212> TYPE: PRT
<213> ORGANISM: Mus musculus

<400> SEQUENCE: 18

Leu Gln Tyr Asp Glu Phe Pro Leu Thr
1               5

<210> SEQ ID NO 19
<211> LENGTH: 11
<212> TYPE: PRT
<213> ORGANISM: Mus musculus

<400> SEQUENCE: 19

Lys Ala Ser Gln Asp Ile Asn Arg Tyr Leu Asn
1               5                   10

<210> SEQ ID NO 20
<211> LENGTH: 7
<212> TYPE: PRT
<213> ORGANISM: Mus musculus

<400> SEQUENCE: 20

Arg Ala Asn Arg Leu Leu Asp

```
<210> SEQ ID NO 21
<211> LENGTH: 9
<212> TYPE: PRT
<213> ORGANISM: Mus musculus

<400> SEQUENCE: 21

Leu Gln Tyr Asp Glu Phe Pro Leu Thr
1               5

<210> SEQ ID NO 22
<211> LENGTH: 6
<212> TYPE: PRT
<213> ORGANISM: Mus musculus

<400> SEQUENCE: 22

Gln Asp Ile Asn Arg Tyr
1               5

<210> SEQ ID NO 23
<211> LENGTH: 3
<212> TYPE: PRT
<213> ORGANISM: Mus musculus

<400> SEQUENCE: 23

Arg Ala Asn
1

<210> SEQ ID NO 24
<211> LENGTH: 9
<212> TYPE: PRT
<213> ORGANISM: Mus musculus

<400> SEQUENCE: 24

Leu Gln Tyr Asp Glu Phe Pro Leu Thr
1               5

<210> SEQ ID NO 25
<211> LENGTH: 118
<212> TYPE: PRT
<213> ORGANISM: Mus musculus

<400> SEQUENCE: 25

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Asn Pro Glu Lys Arg Leu Glu Trp Val
        35                  40                  45

Ala Ser Ile Ser Lys Gly Gly Asn Thr Tyr Tyr Pro Asn Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Leu Tyr Tyr Cys Ala
                85                  90                  95

Arg Gly Trp Gly Asp Tyr Gly Trp Phe Ala Tyr Trp Gly Gln Val Thr
            100                 105                 110

Leu Val Thr Val Ser Ala
        115
```

<210> SEQ ID NO 26
<211> LENGTH: 118
<212> TYPE: PRT
<213> ORGANISM: Artificial Sequence
<220> FEATURE:
<223> OTHER INFORMATION: VH91 sequence

<400> SEQUENCE: 26

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Lys Gly Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Gly Asp Tyr Gly Trp Phe Ala Tyr Trp Gly Gln Val Thr
            100                 105                 110

Leu Val Thr Val Ser Ser
        115
```

<210> SEQ ID NO 27
<211> LENGTH: 118
<212> TYPE: PRT
<213> ORGANISM: Artificial Sequence
<220> FEATURE:
<223> OTHER INFORMATION: VH92 sequence

<400> SEQUENCE: 27

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Lys Gly Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Trp Gly Asp Tyr Gly Trp Phe Ala Tyr Trp Gly Gln Val Thr
            100                 105                 110

Leu Val Thr Val Ser Ser
        115
```

<210> SEQ ID NO 28
<211> LENGTH: 118
<212> TYPE: PRT
<213> ORGANISM: Artificial Sequence
<220> FEATURE:
<223> OTHER INFORMATION: VH93 sequence

<400> SEQUENCE: 28

```
Gln Val Gln Leu Val Glu Ser Gly Gly Gly Leu Val Lys Pro Gly Gly
 1               5                  10                  15
```

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
            35                  40                  45

Ser Ser Ile Ser Lys Gly Gly Asn Thr Tyr Tyr Ala Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
            85                  90                  95

Arg Gly Trp Gly Asp Tyr Gly Trp Phe Ala Tyr Trp Gly Gln Val Thr
            100                 105                 110

Leu Val Thr Val Ser Ser
            115

<210> SEQ ID NO 29
<211> LENGTH: 118
<212> TYPE: PRT
<213> ORGANISM: Artificial Sequence
<220> FEATURE:
<223> OTHER INFORMATION: VH94 sequence

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Tyr
            20                  25                  30

Ala Met Ser Trp Val Arg Gln Ala Pro Gly Gln Arg Leu Glu Trp Met
            35                  40                  45

Gly Ser Ile Ser Lys Gly Gly Asn Thr Tyr Tyr Ser Gln Lys Phe Gln
50                  55                  60

Gly Arg Val Thr Ile Thr Arg Asp Thr Ser Ala Ser Thr Ala Tyr Met
65                  70                  75                  80

Glu Leu Ser Ser Leu Arg Ser Glu Asp Thr Ala Val Tyr Tyr Cys Ala
            85                  90                  95

Arg Gly Trp Gly Asp Tyr Gly Trp Phe Ala Tyr Trp Gly Gln Val Thr
            100                 105                 110

Leu Val Thr Val Ser Ser
            115

<210> SEQ ID NO 30
<211> LENGTH: 107
<212> TYPE: PRT
<213> ORGANISM: Mus musculus

<400> SEQUENCE: 30

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Arg Tyr
            20                  25                  30

Leu Asn Trp Phe Gln Gln Lys Pro Gly Lys Ser Pro Lys Thr Leu Ile
            35                  40                  45

Tyr Arg Ala Asn Arg Leu Leu Asp Gly Val Pro Ser Arg Phe Ser Gly
        50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Leu
            85                  90                  95

Thr Phe Gly Asp Gly Thr Lys Leu Glu Leu Lys
        100                 105

<210> SEQ ID NO 31
<211> LENGTH: 107
<212> TYPE: PRT
<213> ORGANISM: Artificial Sequence
<220> FEATURE:
<223> OTHER INFORMATION: VL77 sequence

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Arg Tyr
            20                  25                  30

Leu Asn Trp Phe Gln Gln Lys Pro Gly Lys Ala Pro Lys Ser Leu Ile
        35                  40                  45

Tyr Arg Ala Asn Arg Leu Leu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
            85                  90                  95

Thr Phe Gly Gln Gly Thr Lys Leu Glu Ile Lys
        100                 105

<210> SEQ ID NO 32
<211> LENGTH: 107
<212> TYPE: PRT
<213> ORGANISM: Artificial Sequence
<220> FEATURE:
<223> OTHER INFORMATION: VL78 sequence

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Arg Tyr
            20                  25                  30

Leu Asn Trp Phe Gln Gln Lys Pro Gly Lys Ala Pro Lys Ser Leu Ile
        35                  40                  45

Tyr Arg Ala Asn Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
            85                  90                  95

Thr Phe Gly Gln Gly Thr Lys Leu Glu Ile Lys
        100                 105

<210> SEQ ID NO 33
<211> LENGTH: 107
<212> TYPE: PRT
<213> ORGANISM: Artificial Sequence
<220> FEATURE:
<223> OTHER INFORMATION: VL79 sequence

<400> SEQUENCE: 33

Asp Ile Gln Met Thr Gln Ser Pro Ser Ser Leu Ser Ala Ser Val Gly

```
              1               5                  10                 15
Asp Arg Val Thr Ile Thr Cys Lys Ala Ser Gln Asp Ile Asn Arg Tyr
                       20                  25                 30

Leu Asn Trp Tyr Gln Gln Lys Pro Gly Lys Ala Pro Lys Leu Leu Ile
             35                  40                  45

Tyr Arg Ala Asn Arg Leu Leu Asp Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                 85                  90                  95

Thr Phe Gly Gln Gly Thr Lys Leu Glu Ile Lys
              100                 105
```

<210> SEQ ID NO 34
<211> LENGTH: 107
<212> TYPE: PRT
<213> ORGANISM: Artificial Sequence
<220> FEATURE:
<223> OTHER INFORMATION: VL80 sequence

<400> SEQUENCE: 34

```
Asp Ile Val Met Thr Gln Thr Pro Leu Ser Ser Pro Val Thr Leu Gly
1               5                  10                 15

Gln Pro Ala Ser Ile Ser Cys Lys Ala Ser Gln Asp Ile Asn Arg Tyr
                20                  25                  30

Leu Asn Trp Leu Gln Gln Arg Pro Gly Gln Pro Pro Arg Leu Leu Ile
             35                  40                  45

Tyr Arg Ala Asn Arg Leu Leu Asp Gly Val Pro Asp Arg Phe Ser Gly
         50                  55                  60

Ser Gly Ala Gly Thr Asp Phe Thr Leu Lys Ile Ser Arg Val Glu Ala
65                  70                  75                  80

Glu Asp Val Gly Val Tyr Tyr Cys Leu Gln Tyr Asp Glu Phe Pro Leu
                 85                  90                  95

Thr Phe Gly Gln Gly Thr Lys Leu Glu Ile Lys
              100                 105
```

<210> SEQ ID NO 35
<211> LENGTH: 354
<212> TYPE: DNA
<213> ORGANISM: Mus musculus

<400> SEQUENCE: 35

```
gaagtgaagc tggtggaatc tggcggcgac ctcgtgaagc ctggcggctc tctgaagctg     60
agctgtgccg ccagcggctt caccttcagc agctacgcca tgagctgggt gcgccagaac    120
cccgagaagc ggctggaatg gtggccagc atcagcaagg gcggcaacac ctactacccc     180
aacagcgtga agggccggtt caccatctcc cgggacaacg cccggaacat cctgtacctg    240
cagatgagca gcctgcggag cgaggacacc gccctgtact attgtgccag aggctggggc    300
gactacggat ggttcgccta ttggggccaa gtgaccctcg tgaccgtgtc cgct          354
```

<210> SEQ ID NO 36
<211> LENGTH: 354
<212> TYPE: DNA
<213> ORGANISM: Artificial Sequence
<220> FEATURE:
<223> OTHER INFORMATION: VH91 sequence

<400> SEQUENCE: 36

```
gaagtgcagc tgctggaatc tggcggcgga ctggtgcagc ctggcggatc tctgagactg      60
agctgtgccg ccagcggctt caccttcagc agctacgcca tgagctgggt gcgccaggcc     120
cctggaaaag gcctggaatg ggtgtccagc atcagcaagg cggcaacac  ctactacgcc     180 gacagcgtga agggccggtt caccatctcc cgggacaaca gcaagaacac cctgtacctg     240
cagatgaaca gcctgcgggc cgaggacacc gccgtgtact attgtgccaa gggctggggc     300
gactacggat ggttcgccta ttggggccaa gtgaccctcg tgaccgtgtc ctct            354
```

<210> SEQ ID NO 37
<211> LENGTH: 354
<212> TYPE: DNA
<213> ORGANISM: Artificial Sequence
<220> FEATURE:
<223> OTHER INFORMATION: VH92 sequence

<400> SEQUENCE: 37

```
caggtgcagc tggtggaatc tggcggcgga gtggtgcagc ctggcagaag cctgagactg      60
agctgtgccg ccagcggctt caccttcagc agctacgcca tgagctgggt gcgccaggcc     120
cctggaaaag gcctggaatg ggtggccagc atcagcaagg cggcaacac  ctactacgcc     180 gacagcgtga agggccggtt caccatctcc cgggacaaca gcaagaacac cctgtacctg     240
cagatgaaca gcctgcgggc cgaggacacc gccgtgtact attgtgccag aggctggggc     300
gactacggat ggttcgccta ttggggccaa gtgaccctcg tgaccgtgtc ctct            354
```

<210> SEQ ID NO 38
<211> LENGTH: 354
<212> TYPE: DNA
<213> ORGANISM: Artificial Sequence
<220> FEATURE:
<223> OTHER INFORMATION: VH93 sequence

<400> SEQUENCE: 38

```
caggtgcagc tggtggagtc cggaggaggc ctggtgaaac ctggcggctc cctgagactg      60
agctgtgccg ccagcggctt caccttcagc agctacgcca tgagctggat caggcaggcc     120
cctggcaagg gactggagtg ggtgagcagc atcagcaagg cggcaacac  ctactacgcc     180 gacagcgtga agggcaggtt cacaatcagc agggacaacg ccaagaacag cctgtacctg     240
cagatgaact ccctgagggc cgaggacacc gccgtgtact actgcgctag ggctggggc      300 gattacggct ggttcgccta ctggggccag gtgaccctgg tgaccgtgag cagc            354
```

<210> SEQ ID NO 39
<211> LENGTH: 354
<212> TYPE: DNA
<213> ORGANISM: Artificial Sequence
<220> FEATURE:
<223> OTHER INFORMATION: VH94 sequence

<400> SEQUENCE: 39

```
caggtgcagc tggtgcagtc tggcgccgaa gtgaagaaac caggcgccag cgtgaaggtg      60
tcctgcaagg ccagcggctt caccttcagc agctacgcca tgagctgggt gcgccaggct     120
cctggccaga gactggaatg gatgggcagc atcagcaagg cggcaacac  ctactacagc     180 cagaaattcc agggcagagt gaccatcacc cgggacacct ctgccagcac cgcctacatg     240
gaactgagca gcctgcggag cgaggacacc gccgtgtact attgtgccag aggctggggc     300
gactacggat ggttcgccta ttggggccaa gtgaccctcg tgaccgtgtc ctct            354
```

<210> SEQ ID NO 40
<211> LENGTH: 321
<212> TYPE: DNA
<213> ORGANISM: Mus musculus

<400> SEQUENCE: 40

| | | | | | |
|---|---|---|---|---|---|
| gacatcaaga | tgacccagtc | tccatcttcc | atgtatgcat | ctctaggaga | gagagtcact | 60 |
| atcacttgca | aggcgagtca | ggacattaat | aggtatttaa | actggttcca | gcagaaacca | 120 |
| gggaaatctc | ctaagaccct | gatctatcgt | gcaaacagat | tgctagatgg | ggtcccatca | 180 |
| aggttcagtg | gcagtggatc | tgggcaagat | tactctctca | ccatcagcag | cctggattat | 240 |
| gaagatatgg | gaatttatta | ttgtctacag | tatgatgagt | ttccgctcac | gttcggtgat | 300 |
| gggaccaagc | tggagctgaa | a | | | | 321 |

<210> SEQ ID NO 41
<211> LENGTH: 321
<212> TYPE: DNA
<213> ORGANISM: Artificial Sequence
<220> FEATURE:
<223> OTHER INFORMATION: VL77 sequence

<400> SEQUENCE: 41

| | | | | | |
|---|---|---|---|---|---|
| gacatccaga | tgacccagag | ccccagcagc | ctgtctgcca | gcgtgggcga | cagagtgacc | 60 |
| atcacatgca | aggccagcca | ggacatcaac | agataccctga | actggttcca | gcagaagccc | 120 |
| ggcaaggccc | ccaagagcct | gatctacaga | gccaacagac | tgctagacgg | cgtgcccagc | 180 |
| agattttctg | gcagcggctc | cggcaccgac | ttcaccctga | caatcagctc | cctgcagccc | 240 |
| gaggacttcg | ccacctacta | ctgcctgcag | tacgacgagt | tcccccctgac | ctttggccag | 300 |
| ggcaccaagc | tggaaatcaa | g | | | | 321 |

<210> SEQ ID NO 42
<211> LENGTH: 321
<212> TYPE: DNA
<213> ORGANISM: Artificial Sequence
<220> FEATURE:
<223> OTHER INFORMATION: VL78 sequence

<400> SEQUENCE: 42

| | | | | | |
|---|---|---|---|---|---|
| gacatccaga | tgacccagag | ccccagcagc | ctgtctgcca | gcgtgggcga | cagagtgacc | 60 |
| atcacatgca | aggccagcca | ggacatcaac | agataccctga | actggttcca | gcagaagccc | 120 |
| ggcaaggccc | ccaagagcct | gatctacaga | gccaacagac | tgctgagcgg | cgtgcccagc | 180 |
| agattttctg | gcagcggctc | cggcaccgac | ttcaccctga | caatcagctc | cctgcagccc | 240 |
| gaggacttcg | ccacctacta | ctgcctgcag | tacgacgagt | tcccccctgac | ctttggccag | 300 |
| ggcaccaagc | tggaaatcaa | g | | | | 321 |

<210> SEQ ID NO 43
<211> LENGTH: 321
<212> TYPE: DNA
<213> ORGANISM: Artificial Sequence
<220> FEATURE:
<223> OTHER INFORMATION: VL79 sequence

<400> SEQUENCE: 43

| | | | | | |
|---|---|---|---|---|---|
| gacatccaga | tgacccagag | ccccagcagc | ctgtctgcca | gcgtgggcga | cagagtgacc | 60 |
| atcacatgca | aggccagcca | ggacatcaac | agataccctga | actggtatca | gcagaagccc | 120 |

```
ggcaaggccc ccaagctgct gatctacaga gccaacagac tgctggacgg cgtgcccagc    180
agattttctg gcagcggctc cggcaccgac ttcaccctga caatcagctc cctgcagccc    240
gaggacttcg ccacctacta ctgcctgcag tacgacagt tccccctgac ctttggccag    300
ggcaccaagc tggaaatcaa g                                              321

<210> SEQ ID NO 44
<211> LENGTH: 321
<212> TYPE: DNA
<213> ORGANISM: Artificial Sequence
<220> FEATURE:
<223> OTHER INFORMATION: VL80 sequence

<400> SEQUENCE: 44
gacatcgtga tgacccagac ccccctgagc agccctgtga ccctgggaca gcctgccagc     60
atcagctgca aggccagcca ggacatcaac agatacctga actggctgca gcagagaccc    120
ggccagcctc ctaggctgct gatctacagg gccaacagac tgctggacgg cgtgcccgac    180
agattctccg gcagcggagc tggcaccgac ttcaccctga gatcagcag ggtggaggcc    240 gaggacgtgg gcgtgtacta ctgcctgcag tacgacgagt tccccctgac cttcggccag    300
ggcaccaagc tggagatcaa g                                              321

<210> SEQ ID NO 45
<211> LENGTH: 448
<212> TYPE: PRT
<213> ORGANISM: Artificial Sequence
<220> FEATURE:
<223> OTHER INFORMATION: heavy chain sequence of HFA PT3

<400> SEQUENCE: 45

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Lys Gly Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Trp Gly Asp Tyr Gly Trp Phe Ala Tyr Trp Gly Gln Val Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 46
<211> LENGTH: 214
<212> TYPE: PRT
<213> ORGANISM: Artificial Sequence
<220> FEATURE:
<223> OTHER INFORMATION: light chain sequence of HFA PT3

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Arg Tyr
            20                  25                  30

Leu Asn Trp Phe Gln Gln Lys Pro Gly Lys Ala Pro Lys Ser Leu Ile
        35                  40                  45

Tyr Arg Ala Asn Arg Leu Leu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 47
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 47

Gly Thr Pro Gly Ser Arg Ser Arg Thr Pro Ser Leu Pro Thr Pro Pro
1               5                   10                  15
Thr Arg Glu Pro Lys Lys
            20

<210> SEQ ID NO 48
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 48

Gly Thr Pro Gly Ser Arg Ser Arg Thr Pro Ser Leu Pro Thr Pro Pro
1               5                   10                  15
Thr Arg Glu Pro Lys Lys
            20

<210> SEQ ID NO 49
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
```

<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 49

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 50
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 50

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 51
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 51

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 52
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (14)..(14)
<223> OTHER INFORMATION: PHOSPHORYLATION

<400> SEQUENCE: 52

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 53
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 53

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 54
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (9)..(9)
<223> OTHER INFORMATION: PHOSPHORYLATION

<400> SEQUENCE: 54

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 55
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (11)..(11)
<223> OTHER INFORMATION: PHOSPHORYLATION

<400> SEQUENCE: 55

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 56
<211> LENGTH: 22
<212> TYPE: PRT
<213> ORGANISM: Artificial Sequence
<220> FEATURE:
<223> OTHER INFORMATION: phospho tau peptide

```
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 56

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 57
<211> LENGTH: 19
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 57

Ser Pro Gly Thr Pro Gly Ser Arg Ser Arg Thr Pro Ser Leu Pro Thr
1               5                   10                  15

Pro Pro Thr

<210> SEQ ID NO 58
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (7)..(7)
<223> OTHER INFORMATION: PHOSPHORYLATION

<400> SEQUENCE: 58

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 59
<211> LENGTH: 22
<212> TYPE: PRT
<213> ORGANISM: Artificial Sequence
<220> FEATURE:
<223> OTHER INFORMATION: phospho tau peptide
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION
```

```
<400> SEQUENCE: 59

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 60
<211> LENGTH: 22
<212> TYPE: PRT
<213> ORGANISM: Artificial Sequence
<220> FEATURE:
<223> OTHER INFORMATION: control tau peptide

<400> SEQUENCE: 60

Gly Thr Pro Gly Ser Arg Ser Arg Thr Pro Ser Leu Pro Thr Pro Pro
1               5                   10                  15

Thr Arg Glu Pro Lys Lys
            20

<210> SEQ ID NO 61
<211> LENGTH: 14
<212> TYPE: PRT
<213> ORGANISM: Artificial Sequence
<220> FEATURE:
<223> OTHER INFORMATION: pT212/pS214/pT217-tau peptide
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 61

Gly Ser Arg Ser Arg Thr Pro Ser Leu Pro Thr Pro Pro Thr
1               5                   10

<210> SEQ ID NO 62
<211> LENGTH: 13
<212> TYPE: PRT
<213> ORGANISM: Artificial Sequence
<220> FEATURE:
<223> OTHER INFORMATION: pT212/pT217-tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 62

Ser Arg Thr Pro Ser Leu Pro Thr Pro Pro Thr Arg Glu
1               5                   10

<210> SEQ ID NO 63
<211> LENGTH: 450
<212> TYPE: PRT
<213> ORGANISM: Artificial Sequence
<220> FEATURE:
<223> OTHER INFORMATION: control tau (human tau isoform 2N4R 441 aa,
      N-terminal 6xHis-tag)
```

-continued

```
<400> SEQUENCE: 63

Met His His His His His Gly Ser Met Ala Glu Pro Arg Gln Glu
1               5                   10                  15

Phe Glu Val Met Glu Asp His Ala Gly Thr Tyr Gly Leu Gly Asp Arg
            20                  25                  30

Lys Asp Gln Gly Gly Tyr Thr Met His Gln Asp Gln Glu Gly Asp Thr
            35                  40                  45

Asp Ala Gly Leu Lys Glu Ser Pro Leu Gln Thr Pro Thr Glu Asp Gly
    50                  55                  60

Ser Glu Glu Pro Gly Ser Glu Thr Ser Asp Ala Lys Ser Thr Pro Thr
65                  70                  75                  80

Ala Glu Asp Val Thr Ala Pro Leu Val Asp Glu Gly Ala Pro Gly Lys
                85                  90                  95

Gln Ala Ala Ala Gln Pro His Thr Glu Ile Pro Glu Gly Thr Thr Ala
            100                 105                 110

Glu Glu Ala Gly Ile Gly Asp Thr Pro Ser Leu Glu Asp Glu Ala Ala
            115                 120                 125

Gly His Val Thr Gln Ala Arg Met Val Ser Lys Ser Lys Asp Gly Thr
    130                 135                 140

Gly Ser Asp Asp Lys Lys Ala Lys Gly Ala Asp Gly Lys Thr Lys Ile
145                 150                 155                 160

Ala Thr Pro Arg Gly Ala Ala Pro Pro Gly Gln Lys Gly Gln Ala Asn
                165                 170                 175

Ala Thr Arg Ile Pro Ala Lys Thr Pro Pro Ala Pro Lys Thr Pro Pro
            180                 185                 190

Ser Ser Gly Glu Pro Pro Lys Ser Gly Asp Arg Ser Gly Tyr Ser Ser
            195                 200                 205

Pro Gly Ser Pro Gly Thr Pro Gly Ser Arg Ser Arg Thr Pro Ser Leu
    210                 215                 220

Pro Thr Pro Pro Thr Arg Glu Pro Lys Lys Val Ala Val Val Arg Thr
225                 230                 235                 240

Pro Pro Lys Ser Pro Ser Ser Ala Lys Ser Arg Leu Gln Thr Ala Pro
                245                 250                 255

Val Pro Met Pro Asp Leu Lys Asn Val Lys Ser Lys Ile Gly Ser Thr
            260                 265                 270

Glu Asn Leu Lys His Gln Pro Gly Gly Gly Lys Val Gln Ile Ile Asn
            275                 280                 285

Lys Lys Leu Asp Leu Ser Asn Val Gln Ser Lys Cys Gly Ser Lys Asp
    290                 295                 300

Asn Ile Lys His Val Pro Gly Gly Gly Ser Val Gln Ile Val Tyr Lys
305                 310                 315                 320

Pro Val Asp Leu Ser Lys Val Thr Ser Lys Cys Gly Ser Leu Gly Asn
                325                 330                 335

Ile His His Lys Pro Gly Gly Gly Gln Val Glu Val Lys Ser Glu Lys
            340                 345                 350

Leu Asp Phe Lys Asp Arg Val Gln Ser Lys Ile Gly Ser Leu Asp Asn
            355                 360                 365

Ile Thr His Val Pro Gly Gly Gly Asn Lys Lys Ile Glu Thr His Lys
    370                 375                 380

Leu Thr Phe Arg Glu Asn Ala Lys Ala Lys Thr Asp His Gly Ala Glu
385                 390                 395                 400

Ile Val Tyr Lys Ser Pro Val Val Ser Gly Asp Thr Ser Pro Arg His
```

```
                        405                 410                 415
Leu Ser Asn Val Ser Ser Thr Gly Ser Ile Asp Met Val Asp Ser Pro
                420                 425                 430
Gln Leu Ala Thr Leu Ala Asp Glu Val Ser Ala Ser Leu Ala Lys Gln
            435                 440                 445
Gly Leu
    450

<210> SEQ ID NO 64
<211> LENGTH: 352
<212> TYPE: PRT
<213> ORGANISM: Homo sapiens

<400> SEQUENCE: 64

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Ala Glu Glu Ala
            35                  40                  45
Gly Ile Gly Asp Thr Pro Ser Leu Glu Asp Glu Ala Ala Gly His Val
    50                  55                  60
Thr Gln Ala Arg Met Val Ser Lys Ser Lys Asp Gly Thr Gly Ser Asp
65                  70                  75                  80
Asp Lys Lys Ala Lys Gly Ala Asp Gly Lys Thr Lys Ile Ala Thr Pro
                85                  90                  95
Arg Gly Ala Ala Pro Pro Gly Gln Lys Gly Gln Ala Asn Ala Thr Arg
            100                 105                 110
Ile Pro Ala Lys Thr Pro Pro Ala Pro Lys Thr Pro Pro Ser Ser Gly
    115                 120                 125
Glu Pro Pro Lys Ser Gly Asp Arg Ser Gly Tyr Ser Ser Pro Gly Ser
130                 135                 140
Pro Gly Thr Pro Gly Ser Arg Ser Arg Thr Pro Ser Leu Pro Thr Pro
145                 150                 155                 160
Pro Thr Arg Glu Pro Lys Lys Val Ala Val Arg Thr Pro Pro Lys
                165                 170                 175
Ser Pro Ser Ser Ala Lys Ser Arg Leu Gln Thr Ala Pro Val Pro Met
            180                 185                 190
Pro Asp Leu Lys Asn Val Lys Ser Lys Ile Gly Ser Thr Glu Asn Leu
    195                 200                 205
Lys His Gln Pro Gly Gly Gly Lys Val Gln Ile Val Tyr Lys Pro Val
210                 215                 220
Asp Leu Ser Lys Val Thr Ser Lys Cys Gly Ser Leu Gly Asn Ile His
225                 230                 235                 240
His Lys Pro Gly Gly Gly Gln Val Glu Val Lys Ser Glu Lys Leu Asp
                245                 250                 255
Phe Lys Asp Arg Val Gln Ser Lys Ile Gly Ser Leu Asp Asn Ile Thr
            260                 265                 270
His Val Pro Gly Gly Gly Asn Lys Lys Ile Glu Thr His Lys Leu Thr
    275                 280                 285
Phe Arg Glu Asn Ala Lys Ala Lys Thr Asp His Gly Ala Glu Ile Val
290                 295                 300
Tyr Lys Ser Pro Val Val Ser Gly Asp Thr Ser Pro Arg His Leu Ser
305                 310                 315                 320
```

```
Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 65
<211> LENGTH: 381
<212> TYPE: PRT
<213> ORGANISM: Homo sapiens

<400> SEQUENCE: 65

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350
```

Ser Thr Gly Ser Ile Asp Met Val Asp Ser Pro Gln Leu Ala Thr Leu
            355                 360                 365

Ala Asp Glu Val Ser Ala Ser Leu Ala Lys Gln Gly Leu
370                 375                 380

<210> SEQ ID NO 66
<211> LENGTH: 410
<212> TYPE: PRT
<213> ORGANISM: Homo sapiens

<400> SEQUENCE: 66

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
    290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys

```
                340             345             350
Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
        370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 67
<211> LENGTH: 383
<212> TYPE: PRT
<213> ORGANISM: Homo sapiens

<400> SEQUENCE: 67

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300
```

```
Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
                340                 345                 350

Val Ser Ser Thr Gly Ser Ile Asp Met Val Asp Ser Pro Gln Leu Ala
                355                 360                 365

Thr Leu Ala Asp Glu Val Ser Ala Ser Leu Ala Lys Gln Gly Leu
                370                 375                 380

<210> SEQ ID NO 68
<211> LENGTH: 441
<212> TYPE: PRT
<213> ORGANISM: Homo sapiens

<400> SEQUENCE: 68

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
                115                 120                 125

Ser Lys Ser Lys Asp Gly Thr Gly Ser Asp Asp Lys Lys Ala Lys Gly
            130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
            210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300
```

```
Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
                370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
                435                 440

<210> SEQ ID NO 69
<211> LENGTH: 441
<212> TYPE: PRT
<213> ORGANISM: Homo sapiens

<400> SEQUENCE: 69

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
                35                  40                  45

Gln Thr Pro Thr Glu Asp Gly Ser Glu Glu Pro Gly Ser Glu Thr Ser
                50                  55                  60

Asp Ala Lys Ser Thr Pro Thr Ala Glu Asp Val Thr Ala Pro Leu Val
65              70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
                115                 120                 125

Ser Lys Ser Lys Asp Gly Thr Gly Ser Asp Asp Lys Lys Ala Lys Gly
                130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
                210                 215                 220

Lys Val Ala Val Val Arg Thr Pro Pro Lys Ser Pro Ser Ser Ala Lys
```

```
                225                 230                 235                 240
Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 70
<211> LENGTH: 11
<212> TYPE: PRT
<213> ORGANISM: Mus musculus

<400> SEQUENCE: 70

Lys Ala Ser Gln Asp Ile Asn Arg Trp Leu Asn
1               5                   10

<210> SEQ ID NO 71
<211> LENGTH: 6
<212> TYPE: PRT
<213> ORGANISM: Mus musculus

<400> SEQUENCE: 71

Thr Ser Tyr Ala Met Ser
1               5

<210> SEQ ID NO 72
<211> LENGTH: 16
<212> TYPE: PRT
<213> ORGANISM: Mus musculus

<400> SEQUENCE: 72

Ser Ile Thr Lys Gly Gly Asn Thr Tyr Tyr Ala Asp Ser Val Lys Gly
1               5                   10                  15

<210> SEQ ID NO 73
<211> LENGTH: 10
<212> TYPE: PRT
<213> ORGANISM: Mus musculus
```

<400> SEQUENCE: 73

| Gly | Trp | Gly | Ile | Tyr | Gly | Trp | Phe | Ala | Tyr |
|-----|-----|-----|-----|-----|-----|-----|-----|-----|-----|
| 1   |     |     |     | 5   |     |     |     |     | 10  |

<210> SEQ ID NO 74
<211> LENGTH: 448
<212> TYPE: PRT
<213> ORGANISM: Artificial Sequence
<220> FEATURE:
<223> OTHER INFORMATION: heavy chain sequence

<400> SEQUENCE: 74

| Gln | Val | Gln | Leu | Val | Glu | Ser | Gly | Gly | Val | Gln | Pro | Gly | Arg |
|-----|-----|-----|-----|-----|-----|-----|-----|-----|-----|-----|-----|-----|-----|
| 1   |     |     |     | 5   |     |     |     |     | 10  |     |     |     | 15  |

| Ser | Leu | Arg | Leu | Ser | Cys | Ala | Ala | Ser | Gly | Phe | Thr | Phe | Ser | Ser | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Met | Ser | Trp | Val | Arg | Gln | Ala | Pro | Gly | Lys | Gly | Leu | Glu | Trp | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Ser | Ile | Ser | Lys | Gly | Gly | Asn | Thr | Tyr | Tyr | Ala | Asp | Ser | Val | Lys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gly | Arg | Phe | Thr | Ile | Ser | Arg | Asp | Asn | Ser | Lys | Asn | Thr | Leu | Tyr | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gln | Met | Asn | Ser | Leu | Arg | Ala | Glu | Asp | Thr | Ala | Val | Tyr | Tyr | Cys | Ala |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Arg | Gly | Trp | Gly | Asp | Tyr | Gly | Trp | Phe | Ala | Tyr | Trp | Gly | Gln | Val | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Leu | Val | Thr | Val | Ser | Ser | Ala | Ser | Thr | Lys | Gly | Pro | Ser | Val | Phe | Pro |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Leu | Ala | Pro | Ser | Ser | Lys | Ser | Thr | Ser | Gly | Gly | Thr | Ala | Ala | Leu | Gly |
|-----|-----|-----|-----|-----|-----|-----|-----|-----|-----|-----|-----|-----|-----|-----|-----|
|     |     | 130 |     |     |     |     | 135 |     |     |     |     | 140 |     |     |     |

| Cys | Leu | Val | Lys | Asp | Tyr | Phe | Pro | Glu | Pro | Val | Thr | Val | Ser | Trp | Asn |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ser | Gly | Ala | Leu | Thr | Ser | Gly | Val | His | Thr | Phe | Pro | Ala | Val | Leu | Gln |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ser | Ser | Gly | Leu | Tyr | Ser | Leu | Ser | Ser | Val | Val | Thr | Val | Pro | Ser | Ser |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Ser | Leu | Gly | Thr | Gln | Thr | Tyr | Ile | Cys | Asn | Val | Asn | His | Lys | Pro | Ser |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Asn | Thr | Lys | Val | Asp | Lys | Lys | Val | Glu | Pro | Lys | Ser | Cys | Asp | Lys | Thr |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| His | Thr | Cys | Pro | Pro | Cys | Pro | Ala | Pro | Glu | Leu | Leu | Gly | Gly | Pro | Ser |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Val | Phe | Leu | Phe | Pro | Pro | Lys | Pro | Lys | Asp | Thr | Leu | Met | Ile | Ser | Arg |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Thr | Pro | Glu | Val | Thr | Cys | Val | Val | Val | Asp | Val | Ser | His | Glu | Asp | Pro |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Glu | Val | Lys | Phe | Asn | Trp | Tyr | Val | Asp | Gly | Val | Glu | Val | His | Asn | Ala |
|-----|-----|-----|-----|-----|-----|-----|-----|-----|-----|-----|-----|-----|-----|-----|-----|
|     |     |     | 275 |     |     |     |     | 280 |     |     |     |     | 285 |     |     |

| Lys | Thr | Lys | Pro | Arg | Glu | Glu | Gln | Tyr | Asn | Ser | Thr | Tyr | Arg | Val | Val |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Ser | Val | Leu | Thr | Val | Leu | His | Gln | Asp | Trp | Leu | Asn | Gly | Lys | Glu | Tyr |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Lys | Cys | Lys | Val | Ser | Asn | Lys | Ala | Leu | Pro | Ala | Pro | Ile | Glu | Lys | Thr |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 75
<211> LENGTH: 214
<212> TYPE: PRT
<213> ORGANISM: Artificial Sequence
<220> FEATURE:
<223> OTHER INFORMATION: light chain sequence

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Arg Trp
            20                  25                  30

Leu Asn Trp Phe Gln Gln Lys Pro Gly Lys Ala Pro Lys Ser Leu Ile
        35                  40                  45

Tyr Arg Ala Asn Arg Leu Leu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 76
<211> LENGTH: 448
<212> TYPE: PRT
<213> ORGANISM: Artificial Sequence
<220> FEATURE:

<223> OTHER INFORMATION: heavy chain sequence

<400> SEQUENCE: 76

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Ser Ile Thr Lys Gly Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Trp Gly Ile Tyr Gly Trp Phe Ala Tyr Trp Gly Gln Val Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
            405                 410                 415
Arg Trp Gln Gln Gly Asn Val Phe Ser Cys Ser Val Met His Glu Ala
        420                 425                 430
Leu His Asn His Tyr Thr Gln Lys Ser Leu Ser Leu Ser Pro Gly Lys
        435                 440                 445

<210> SEQ ID NO 77
<211> LENGTH: 214
<212> TYPE: PRT
<213> ORGANISM: Artificial Sequence
<220> FEATURE:
<223> OTHER INFORMATION: light chain sequence

<400> SEQUENCE: 77

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Ile Asn Arg Trp
            20                  25                  30
Leu Asn Trp Phe Gln Gln Lys Pro Gly Lys Ala Pro Lys Ser Leu Ile
        35                  40                  45
Tyr Arg Ala Asn Arg Leu Leu Asp Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Gln Tyr Asp Glu Phe Pro Leu
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 78
<211> LENGTH: 448
<212> TYPE: PRT
<213> ORGANISM: Artificial Sequence
<220> FEATURE:
<223> OTHER INFORMATION: heavy chain sequence

<400> SEQUENCE: 78

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Thr Ser Tyr
            20                  25                  30
Ala Met Ser Trp Val Arg Gln Ala Pro Gly Lys Gly Leu Glu Trp Val
        35                  40                  45
```

Ala Ser Ile Thr Lys Gly Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Trp Gly Ile Tyr Gly Trp Phe Ala Tyr Trp Gly Gln Val Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 79
<211> LENGTH: 214

```
<212> TYPE: PRT
<213> ORGANISM: Artificial Sequence
<220> FEATURE:
<223> OTHER INFORMATION: light chain sequence

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Arg Tyr
            20                  25                  30

Leu Asn Trp Phe Gln Gln Lys Pro Gly Lys Ala Pro Lys Ser Leu Ile
        35                  40                  45

Tyr Arg Ala Asn Arg Leu Leu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 80
<211> LENGTH: 6
<212> TYPE: PRT
<213> ORGANISM: Mus musculus

<400> SEQUENCE: 80

Ser Ser Tyr Ala Met Ser
1               5

<210> SEQ ID NO 81
<211> LENGTH: 16
<212> TYPE: PRT
<213> ORGANISM: Mus musculus

<400> SEQUENCE: 81

Ser Ile Ser Lys Gly Gly Asn Thr Tyr Tyr Ala Asp Ser Val Lys Gly
1               5                   10                  15
```

ANTI-PHF-TAU ANTIBODIES AND USES THEREOF

This application is a U.S. application Ser. No. 15/923,011, filed on Mar. 16, 2018, now U.S. Pat. No. 10,766,953, which claims the benefit of U.S. Provisional Application No. 62/472,214 filed on Mar. 16, 2017, the entire contents of which is incorporated herein by reference in its entirety.

FIELD OF THE INVENTION

The invention relates to anti-PHF-tau antibodies, nucleic acids and expression vectors encoding the antibodies, recombinant cells containing the vectors, and compositions comprising the antibodies. Methods of making the antibodies, methods of using the antibodies to treat conditions including tauopathies, and methods of using the antibodies to diagnose diseases such as tauopathies are also provided.

BACKGROUND OF THE INVENTION

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in ethnic groups worldwide and presents a major present and future public health problem.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles of paired helical filaments, are generally found in several areas of the human brain important for memory and cognitive function in patients with AD.

The current AD treatment landscape includes only therapies approved to treat cognitive symptoms in patients with dementia. There are no approved therapies that modify or slow the progression of AD. Potential disease modifiers include Eli Lilly's humanized anti-$A_\beta$ monoclonal Solanezumab for patients with mild AD and Merck's small molecule BACE inhibitor Verubecestat for patients with mild-to-moderate AD. These therapies, and most other potential disease modifiers that may launch in the next decade, target $A_\beta$ (the principle component of the amyloid plaques that are one of the two "hallmark" pathological signs of AD).

Neurofibrillary tangles, the second hallmark pathological sign of AD, are primarily composed of aggregates of hyperphosphorylated tau protein. The main physiological function of tau is microtubule polymerization and stabilization. The binding of tau to microtubules takes place by ionic interactions between positive charges in the microtubule binding region of tau and negative charges on the microtubule lattice (Butner and Kirschner, *J Cell Biol.* 115(3):717-30, 1991). Tau protein contains 85 possible phosphorylation sites and phosphorylation at many of these sites interferes with the primary function of tau. Tau that is bound to the axonal microtubule lattice is in a hypo-phosphorylation state, while aggregated tau in AD is hyper-phosphorylated, providing unique epitopes that are distinct from the physiologically active pool of tau.

A tauopathy transmission and spreading hypothesis has been described and is based on the Braak stages of tauopathy progression in the human brain and tauopathy spreading after tau aggregate injections in preclinical tau models (Frost et al., *J Biol Chem.* 284:12845-52, 2009; Clavaguera et al., *Nat Cell Biol.* 11:909-13, 2009).

Developing therapeutics preventing or clearing tau aggregation has been of interest for many years and candidate drugs, including anti-aggregation compounds and kinase inhibitors, have entered in clinical testing (Brunden et al., *Nat Rev Drug Discov.* 8:783-93, 2009). Multiple studies have been published that show the beneficial therapeutic effects of both active and passive tau immunization in transgenic mouse models (Chai et al., *J Biol Chem.* 286: 34457-67, 2011; Boutajangout et al., *J Neurochem.* 118:658-67, 2011; Boutajangout et al., *J Neurosci.* 30:16559-66, 2010; Asuni et al., *J Neurosci.* 27:9115-29, 2007). Activity has been reported with both phospho-directed and non-phospho-directed antibodies (Schroeder et al., *J Neuroimmune Pharmacol.* 11(1):9-25, 2016).

Despite the progress in the art, there remains a need for effective therapeutics that prevent tau aggregation and tauopathy progression to treat tauopathies such as AD and other neurodegenerative diseases.

BRIEF SUMMARY OF THE INVENTION

The invention satisfies this need by providing anti-PHF-tau antibodies or antigen-binding fragments thereof that have high binding affinity towards paired helical filament (PHF)-tau and are selective for phosphorylated tau. Antibodies of the invention were generated by human framework adaptation (HFA) of mouse PHF-tau-specific antibodies. It is thought that the selectivity of the antibodies for phosphorylated tau allows for efficacy against pathogenic tau without interfering with normal tau function. The invention also provides nucleic acids encoding the antibodies, compositions comprising the antibodies, and methods of making and using the antibodies. Anti-PHF-tau antibodies or antigen-binding fragments thereof of the invention inhibit tau seeds, as measured by cellular assays using tau seeds derived from HEK cell lysates or from spinal cord lysates from mutant tau transgenic mice. In addition, a chimeric antibody with variable regions of anti-PHF-tau antibodies of the invention and mouse Ig constant regions, such as mouse IgG2a constant regions, blocked seeding activity in an in vivo mutant tau transgenic mouse model.

The progression of tauopathy in an AD brain follows distinct special spreading patterns. It has been shown in preclinical models that extracellular phospho-tau seeds can induce tauopathy in neurons (Clavaguera et al., PNAS 110(23):9535-40, 2013). It is therefore believed that tauopathy can spread in a prion-like fashion from one brain region to the next. This spreading process would involve an externalization of tau seeds that can be taken up by nearby neurons and induce further tauopathy. While not wishing to be bound by theory, it is thought that anti-PHF-tau antibodies or antigen-binding fragments thereof of the invention prevent tau aggregation or the spreading of tauopathy in the brain by interacting with phospho-tau seeds.

In one general aspect, the invention relates to an isolated monoclonal antibody or an antigen-binding fragment thereof that binds PHF-tau. In a specific embodiment, the antibody is a humanized monoclonal antibody.

According to a particular aspect, the invention relates to an isolated monoclonal antibody or antigen-binding fragment thereof that binds to a phosphorylated tau protein at a phosphorylated epitope in the proline rich domain of the tau protein. In a more particular aspect, the phosphorylated epitope comprises phosphorylated T212 and/or phosphorylated T217 of the tau protein, and the phosphorylated epitope having or within any of the amino acid sequences of SEQ ID NOs:48, 52 and 54. In some embodiments, an antibody of the invention binds to the phosphorylated epitope comprises phosphorylated T212 and phosphorylated T217 of the tau protein.

According to a particular aspect, the invention relates to an isolated monoclonal antibody or an antigen-binding fragment thereof, comprising:

(1) immunoglobulin heavy chain complementarity determining regions (HCDRs) HCDR1, HCDR2 and HCDR3 having the polypeptide sequences of SEQ ID NOs: 4, 5 and 6, respectively and immunoglobulin light chain complementarity determining regions (LCDRs) LCDR1, LCDR2 and LCDR3 having the polypeptide sequences of SEQ ID NOs: 16, 17 and 18, respectively;

(2) HCDR1, HCDR2 and HCDR3 having the polypeptide sequences of SEQ ID NOs: 1, 2 and 3, respectively and LCDR1, LCDR2 and LCDR3 having the polypeptide sequences of SEQ ID NOs: 13, 14 and 15, respectively;

(3) HCDR1, HCDR2 and HCDR3 having the polypeptide sequences of SEQ ID NOs: 7, 8 and 9, respectively and LCDR1, LCDR2 and LCDR3 having the polypeptide sequences of SEQ ID NOs: 19, 20 and 21, respectively;

(4) HCDR1, HCDR2 and HCDR3 having the polypeptide sequences of SEQ ID NOs: 10, 11 and 12, respectively and LCDR1, LCDR2 and LCDR3 having the polypeptide sequences of SEQ ID NOs: 22, 23 and 24, respectively;

(5) HCDR1, HCDR2 and HCDR3 having the polypeptide sequences of SEQ ID NOs:80, 81 and 9, respectively and LCDR1, LCDR2 and LCDR3 having the polypeptide sequences of SEQ ID NOs: 70, 20 and 21, respectively;

(6) HCDR1, HCDR2 and HCDR3 having the polypeptide sequences of SEQ ID NOs: 71, 72, 73, respectively and LCDR1, LCDR2 and LCDR3 having the polypeptide sequences of SEQ ID NOs: 70, 20 and 21, respectively;

(7) HCDR1, HCDR2 and HCDR3 having the polypeptide sequences of SEQ ID NOs: 71, 72 and 73, respectively and LCDR1, LCDR2 and LCDR3 having the polypeptide sequences of SEQ ID NOs: 19, 20 and 21, respectively;

(8) HCDR1, HCDR2 and HCDR3 of a $V_H$ region having the polypeptide sequence of SEQ ID NO: 26 and LCDR1, LCDR2 and LCDR3 of a $V_L$ region having the polypeptide sequence of SEQ ID NO: 31;

(9) HCDR1, HCDR2 and HCDR3 of a $V_H$ region having the polypeptide sequence of SEQ ID NO: 28 and LCDR1, LCDR2 and LCDR3 of a $V_L$ region having the polypeptide sequence of SEQ ID NO: 34;

(10) HCDR1, HCDR2 and HCDR3 of a $V_H$ region having the polypeptide sequence of SEQ ID NO: 26 and LCDR1, LCDR2 and LCDR3 of a $V_L$ region having the polypeptide sequence of SEQ ID NO: 34; or

(11) HCDR1, HCDR2 and HCDR3 of a $V_H$ region having the polypeptide sequence of SEQ ID NO: 28 and LCDR1, LCDR2 and LCDR3 of a $V_L$ region having the polypeptide sequence of SEQ ID NO: 31;

wherein the antibody or antigen-binding fragment thereof binds PHF-tau, preferably human PHF-tau.

In a more particular aspect, the framework regions in the heavy chain variable region domain and in the light chain variable region domain comprise amino acid sequences from a human immunoglobulin.

According to another particular aspect, the invention relates to isolated monoclonal antibodies or antigen-binding fragments thereof comprising a heavy chain variable region having a polypeptide sequence at least 80%, preferably at least 85%, preferably at least 90%, more preferably at least 95%, more preferably at least 98% identical, and most preferably 100%, identical to any one of SEQ ID NOs: 26, 27, 28 and 29 or a $V_H$ region of any heavy chain of any one of SEQ ID NOs: 74, 76, and 78, or a light chain variable region having a polypeptide sequence at least 80%, preferably at least 85%, preferably at least 90%, more preferably at least 95%, more preferably at least 98% identical, and most preferably 100% identical to any one of SEQ ID NOs: 31, 32, 33 and 34 or a $V_L$ region of any one of light chain of SEQ ID NOs: 75, 77 and 79.

According to another particular aspect, the invention relates to an isolated monoclonal antibody or antigen-binding fragment thereof comprising a heavy chain having the polypeptide sequence at least 80%, preferably at least 85%, preferably at least 90%, more preferably at least 95%, more preferably at least 98% identical, and most preferably 100% identical to any one of SEQ ID NOs: 45, 74, 76, and 78; and a light chain having the polypeptide sequence at least 80%, preferably at least 85%, preferably at least 90%, more preferably at least 95%, more preferably at least 98% identical, and most preferably 100% identical to any one of SEQ ID NO: 46, 75, 77 and 79.

According to another particular aspect, the isolated monoclonal antibodies or antigen-binding fragments thereof of the invention further comprise a constant region, such as a human or mouse heavy chain IgG constant region, and a human or mouse antibody light chain kappa or lambda constant region.

In another general aspect, the invention relates to an isolated nucleic acid encoding a monoclonal antibody or antigen-binding fragment thereof of the invention.

In another general aspect, the invention relates to a vector comprising an isolated nucleic acid encoding a monoclonal antibody or antigen-binding fragment thereof of the invention.

In another general aspect, the invention relates to a host cell comprising an isolated nucleic acid encoding a monoclonal antibody or antigen-binding fragment thereof of the invention.

In another general aspect, the invention relates to a pharmaceutical composition comprising an isolated monoclonal antibody or antigen-binding fragment thereof of the invention and a pharmaceutically acceptable carrier.

In another general aspect, the invention relates to a method of reducing pathological tau aggregation or spreading of tauopathy in a subject in need thereof, comprising administering to the subject a pharmaceutical composition of the invention.

In another general aspect, the invention relates to a method of treating a tauopathy in a subject in need thereof, comprising administering to the subject a pharmaceutical composition of the invention. The tauopathy includes, but is not limited to, one or more selected from the group consisting of familial Alzheimer's disease, sporadic Alzheimer's disease, frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica (boxing disease).

In another general aspect, the invention relates to a method of producing a monoclonal antibody or antigen-binding fragment thereof of the invention, comprising culturing a cell comprising a nucleic acid encoding the monoclonal antibody or antigen-binding fragment under conditions to produce the monoclonal antibody or antigen-binding fragment thereof, and recovering the monoclonal antibody or antigen-binding fragment thereof from the cell or cell culture.

In another general aspect, the invention relates to a method of producing a pharmaceutical composition comprising a monoclonal antibody or antigen-binding fragment thereof of the invention, comprising combining the monoclonal antibody or antigen-binding fragment thereof with a pharmaceutically acceptable carrier to obtain the pharmaceutical composition.

In another general aspect, the invention relates to a method of detecting the presence of phosphorylated PHF-tau in a subject or a method of diagnosing a tauopathy in a subject by detecting the presence of PHF-tau in the subject using a monoclonal antibody or antigen-binding fragment thereof of the invention.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

FIG. 2 shows western blot analysis of mouse anti-tau monoclonal antibodies after SDS-PAGE of recombinant normal human tau ("NT") and sarcosyl-insoluble PHF-tau ("PT").

FIGS. 3A-3E shows immunohistochemical analysis of PT3 on AD hippocampal tissue which is anti-amyloid 4G8 positive. Monoclonal antibodies used were (A) PT1, (B) PT2, (C) PT3, (D) AT8 and (E) HT7.

FIGS. 5A-5B show the phospho-tau specific staining pattern of PT3 in (A) tau knock out or (B) wild type mouse brain.

FIG. 10 shows the sequences of HFA PT3 heavy chain variable regions, VH91 (SEQ ID NO: 26), VH92 (SEQ ID NO: 27), VH93 (SEQ ID NO: 28), VH94 (SEQ ID NO: 29), and light chain variable regions VL77 (SEQ ID NO: 31), VL78 (SEQ ID NO: 32), VL79 (SEQ ID NO: 33), and VL80 (SEQ ID NO: 34), where the HFA variants are aligned with the PT3 mouse parental V-regions, VH10 (SEQ ID NO: 25) and VL7 (SEQ ID NO: 30). The parental CDRs transferred to human FRs are underlined, and the residue numbering is sequential.

FIGS. 19A-19G show a schematic of the injection model in transgenic mice expressing mutant human P301L tau. IHC images show representative AT8 staining from the injected hemispheres from mice injected with (A-B) a control extract 3 months after injection (C-D) AD-brain-derived ePHF-tau 1 month after injection and (E-F) AD-brain-derived ePHF-tau 3 months after injection. (G) A histogram shows representative biochemistry data from mice treated with increasing amounts of ePHF.

FIGS. 22A-22C show the effect on tau aggregation of co-injection combined with IP peripheral administration of PT3 isotypes followed by seeding with AD-brain-derived PHF-tau in transgenic mice expressing mutant human P301L tau. Mice treated according to (A) show the effect in (B) the injected hemisphere and (C) the non-injected hemisphere.

FIGS. 24A-24J show staining with the (A-C) AT8 or (D-F) PT3 antibodies on cryosections from brain tissue of (A, D) AD patients or (B, C, E, F) PSP patients demonstrated staining in the anatomical regions affected in PSP. (G-J) Controls showed no staining.

FIGS. 25A-25H show SPR binding sensorgrams for affinity-matured mAbs and their Fabs with PHF-tau. Solid lines (gray) indicate kinetics fitting using bivalent binding model (mAbs) or 1:1 Langmuir model (Fabs). (A) B296 mAb (B) B711 mAb (C) B809 mAb (D) B333 mAb (E) B324 Fab of B296 (F) B330 Fab of B711 (G) B332 Fab of B809 (H) B331 Fab of B333.

DETAILED DESCRIPTION OF THE INVENTION

Figure 1:
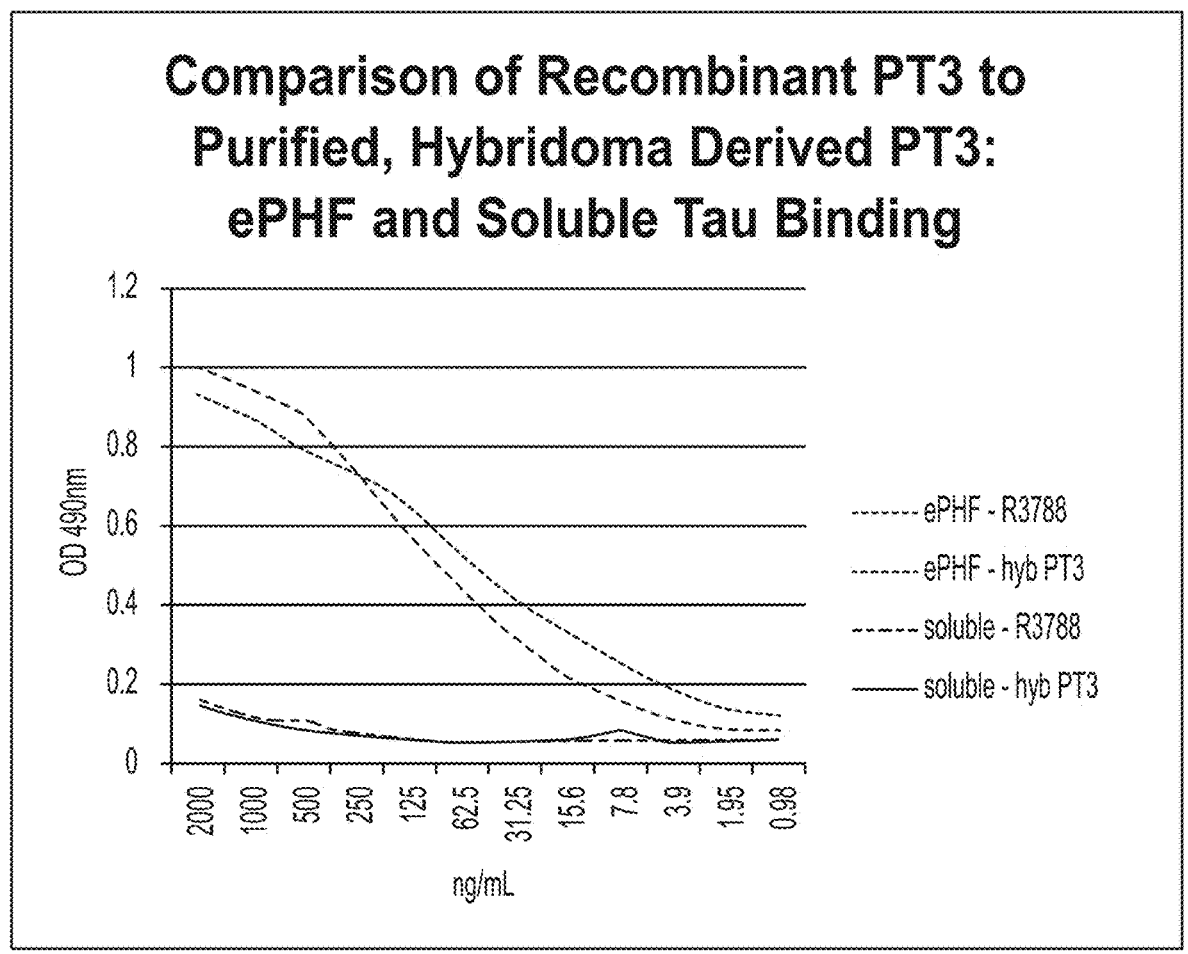
FIG. 1 shows binding of recombinantly expressed PT3 ("R3788") and hybridoma-expressed PT3 ("hyb") to PHF-tau and soluble tau.
Figure 4A:
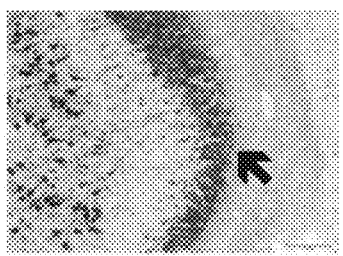
FIGS. 4A-4E show immunohistochemical analysis of PT3 on control hippocampal tissue, which is anti-amyloid 4G8 negative. Monoclonal antibodies used were (A) PT1, (B) PT2, (C) PT3, (D) AT8 and (E) HT7.
Figure 4B:
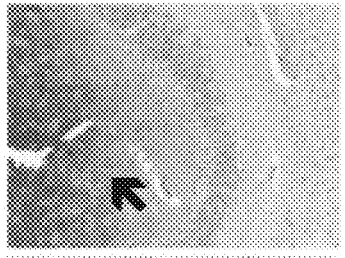
Figure 4C:
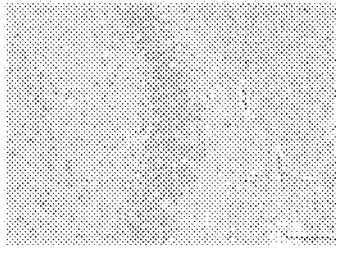
Figure 4D:
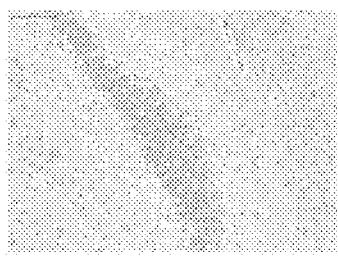
Figure 4E:
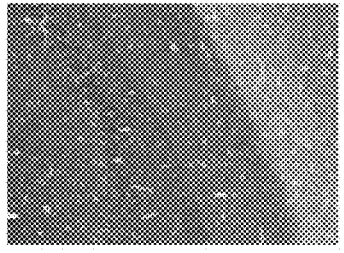

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Definitions

Unless defined otherwise, all technical and scientific terms used herein have the same meaning commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical value, such as a concentration or a concentration range described herein, are to be understood as being modified in all instances by the term "about." Thus, a numerical value typically includes 10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

As used herein, the term "isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids.

As used herein, the term "antibody" or "immunoglobulin" is used in a broad sense and includes immunoglobulin or antibody molecules including polyclonal antibodies, monoclonal antibodies including murine, human, human-adapted, humanized and chimeric monoclonal antibodies and antibody fragments.

In general, antibodies are proteins or peptide chains that exhibit binding specificity to a specific antigen. Antibody structures are well known. Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibodies of the invention include those that have variations in their Fc region such that they have altered properties as compared to wild type Fc regions including, but not limited to, extended half-life, reduced or increased ADCC or CDC and silenced Fc effector functions. Antibody light chains of any vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from mouse antibodies or human antibodies.

In addition to the heavy and light constant domains, antibodies contain light and heavy chain variable regions. An immunoglobulin light or heavy chain variable region consists of a "framework" region interrupted by "antigen-binding sites." The antigen-binding sites are defined using various terms and numbering schemes as follows:

(i) Kabat: "Complementarity Determining Regions" or "CDRs" are based on sequence variability (Wu and Kabat, *J Exp Med.* 132:211-50, 1970). Generally, the antigen-binding site has three CDRs in each variable region (e.g., HCDR1, HCDR2 and HCDR3 in the heavy chain variable region (VH) and LCDR1, LCDR2 and LCDR3 in the light chain variable region (VL));

(ii) Chothia: The term "hypervariable region," "HVR" or "HV" refers to the regions of an antibody variable domain which are hypervariable in structure as defined by Chothia and Lesk (Chothia and Lesk, *J Mol Biol.* 196:901-17, 1987). Generally, the antigen-binding site has three hypervariable regions in each VH (H1, H2, H3) and VL (L1, L2, L3). Numbering systems as well as annotation of CDRs and HVs have been revised by Abhinandan and Martin (Abhinandan and Martin, *Mol Immunol.* 45:3832-9, 2008);

(iii) IMGT: Another definition of the regions that form the antigen-binding site has been proposed by Lefranc (Lefranc et al., *Dev Comp Immunol.* 27:55-77, 2003) based on the comparison of V domains from immunoglobulins and T-cell receptors. The International ImMunoGeneTics (IMGT) database provides a standardized numbering and definition of these regions. The correspondence between CDRs, HVs and IMGT delineations is described in Lefranc et al., 2003, Id.;

(iv) AbM: A compromise between Kabat and Chothia numbering schemes is the AbM numbering convention described by Martin (Martin ACR (2010) Antibody Engineering, eds Kontermann R, Dubel S (Springer-Verlag, Berlin), Vol 2, pp 33-51).

(v) The antigen-binding site can also be delineated based on "Specificity Determining Residue Usage" (SDRU) (Almagro, *Mol Recognit.* 17:132-43, 2004), where SDR, refers to amino acid residues of an immunoglobulin that are directly involved in antigen contact.

"Framework" or "framework sequence" is the remaining sequences within the variable region of an antibody other than those defined to be antigen-binding site sequences. Because the exact definition of an antigen-binding site can be determined by various delineations as described above, the exact framework sequence depends on the definition of the antigen-binding site. The framework regions (FRs) are the more highly conserved portions of variable domains. The variable domains of native heavy and light chains each comprise four FRs (FR1, FR2, FR3 and FR4, respectively) which generally adopt a beta-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., *J. Mol. Biol.* 227: 799-817, 1992; Tramontano et al., *J. Mol. Biol.* 215:175-182, 1990). Despite their high sequence variability, five of the six loops adopt just a small repertoire of main-chain conformations, called "canonical structures." These conformations are first of all determined by the length of the loops and secondly by the presence of key residues at certain positions in the loops and in the framework regions that determine the conformation through their packing, hydrogen bonding or the ability to assume unusual main-chain conformations.

As used herein, the term "antigen-binding fragment" refers to an antibody fragment such as, for example, a diabody, a Fab, a Fab', a F(ab')2, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi-specific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the constant region of the heavy chain. According to other particular embodiments, the antigen-binding fragment comprises Fab and F(ab').

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "epitope" refers to a site on an antigen to which an immunoglobulin, antibody, or antigen-binding fragment thereof, specifically binds. Epitopes can be formed both from contiguous amino acids or from noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, G. E. Morris, Ed. (1996).

As used herein, the term "tau" or "tau protein" refers to an abundant central and peripheral nervous system protein having multiple isoforms. In the human central nervous system (CNS), six major tau isoforms ranging in size from 352 to 441 amino acids in length exist due to alternative splicing (Hanger et al., *Trends Mol Med.* 15:112-9, 2009). The isoforms differ from each other by the regulated inclusion of 0-2 N-terminal inserts, and 3 or 4 tandemly arranged microtubule-binding repeats, and are referred to as 0N3R (SEQ ID NO: 64), 1N3R (SEQ ID NO: 65), 2N3R (SEQ ID NO: 66), 0N4R (SEQ ID NO: 67), 1N4R (SEQ ID NO: 68) and 2N4R (SEQ ID NO: 69). As used herein, the term "control tau" refers to the tau isoform of SEQ ID NO: 69 that is devoid of phosphorylation and other post-translational modifications. As used herein, the term "tau" includes proteins comprising mutations, e.g., point mutations, fragments, insertions, deletions and splice variants of full length wild type tau. The term "tau" also encompasses post-translational modifications of the tau amino acid sequence. Post-translational modifications include, but are not limited to, phosphorylation.

Tau binds microtubules and regulates transport of cargo through cells, a process that can be modulated by tau phosphorylation. In AD and related disorders, abnormal phosphorylation of tau is prevalent and thought to precede and/or trigger aggregation of tau into fibrils, termed paired helical filaments (PHF). The major constituent of PHF is hyper-phosphorylated tau. As used herein, the term "paired helical filament-tau" or "PHF-tau" refers to tau aggregates in paired helical filaments. Two major regions in PHF structure are evident in electron microscopy, the fuzzy coat and the core filament; the fuzzy coat being sensitive to proteolysis and located outside of the filaments, and the protease-resistant core of filaments forming the backbone of PHFs (Wischik et al. *Proc Natl Acad Sci USA.* 85:4884-8, 1988).

An "isolated humanized antibody that binds PHF-tau" or an "isolated humanized anti-PHF-tau antibody", as used herein, is intended to refer to a humanized anti-PHF-tau antibody which is substantially free of other antibodies having different antigenic specificities (for instance, an isolated humanized anti-PHF-tau antibody is substantially free of antibodies that specifically bind antigens other than PHF-tau). An isolated humanized anti-PHF-tau antibody can, however, have cross-reactivity to other related antigens, for instance from other species (such as PHF-tau species homologs).

As used herein, the term "specifically binds" or "specific binding" refers to the ability of an anti-PHF-tau antibody of the invention to bind to a predetermined target with a dissociation constant ($K_D$) of about $1\times10^{-6}$ M or tighter, for example, about $1\times10^{-7}$ M or less, about $1\times10^{-8}$ M or less, about $1\times10^{-9}$ M or less, about $1\times10^{-10}$ M or less, about $1\times10^{-11}$ M or less, about $1\times10^{-12}$ M or less, or about $1\times10^{-13}$ M or less. The KD is obtained from the ratio of Kd to Ka (i.e., Kd/Ka) and is expressed as a molar concentration (M). KD values for antibodies can be determined using methods in the art in view of the present disclosure. For example, the KD value of an anti-PHF-tau antibody can be determined by using surface plasmon resonance, such as by using a biosensor system, e.g., a Biacore® system, a Proteon instrument (BioRad), a KinExA instrument (Sapidyne), ELISA or competitive binding assays known to those skilled in the art. Typically, an anti-PHF-tau antibody binds to a predetermined target (i.e. PHF-tau) with a $K_D$ that is at least ten fold less than its $K_D$ for a nonspecific target as measured by surface plasmon resonance using, for example, a ProteOn Instrument (BioRad). The anti-PHF-tau antibodies that specifically bind to PHF-tau can, however, have cross-reactivity to other related targets, for example, to the same predetermined target from other species (homologs).

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

As used herein, the term "vector" is a replicon in which another nucleic acid segment can be operably inserted so as to bring about the replication or expression of the segment.

As used herein, the term "host cell" refers to a cell comprising a nucleic acid molecule of the invention. The "host cell" can be any type of cell, e.g., a primary cell, a cell in culture, or a cell from a cell line. In one embodiment, a "host cell" is a cell transfected with a nucleic acid molecule of the invention. In another embodiment, a "host cell" is a progeny or potential progeny of such a transfected cell. A progeny of a cell may or may not be identical to the parent cell, e.g., due to mutations or environmental influences that can occur in succeeding generations or integration of the nucleic acid molecule into the host cell genome.

The term "expression" as used herein, and refer to the biosynthesis of a gene product. The term encompasses the transcription of a gene into RNA. The term also encompasses translation of RNA into one or more polypeptides, and further encompasses all naturally occurring post-transcriptional and post-translational modifications. The expressed humanized antibody or antigen-binding fragment thereof that binds PHF-tau can be within the cytoplasm of a host cell, into the extracellular milieu such as the growth medium of a cell culture, or anchored to the cell membrane.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

As used herein, the term "subject" refers to an animal, and preferably a mammal. According to particular embodiments, the subject is a mammal including a non-primate (e.g., a camel, donkey, zebra, cow, pig, horse, goat, sheep, cat, dog, rat, rabbit, guinea pig or mouse) or a primate (e.g., a monkey, chimpanzee, or human). In particular embodiments, the subject is a human.

As used herein, the term "therapeutically effective amount" refers to an amount of an active ingredient or component that elicits the desired biological or medicinal response in a subject. A therapeutically effective amount can be determined empirically and in a routine manner, in relation to the stated purpose. For example, in vitro assays can optionally be employed to help identify optimal dosage ranges. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

As used herein, the terms "treat," "treating," and "treatment" are all intended to refer to an amelioration or reversal of at least one measurable physical parameter related to a tauopathy which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the tauopathy. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

As used herein a "tauopathy" encompasses any neurodegenerative disease that involves the pathological aggregation of tau within the brain. In addition to familial and sporadic AD, other exemplary tauopathies are frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, and chronic traumatic encephalopathy, such as dementia pugulistica (boxing disease) (Morris et al., *Neuron*, 70:410-26, 2011).

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Anti-PHF-tau Antibodies

In one general aspect, the invention relates to isolated monoclonal antibodies or antigen-binding fragments thereof that bind PHF-tau. Such anti-PHF-tau antibodies can have the properties of binding a phosphorylated epitope on PHF-tau or binding to a non-phosphorylated epitope on PHF-tau. Anti-PHF-tau antibodies can be useful as therapeutics, and as research or diagnostic reagents to detect PHF-tau in biological samples, for example in tissues or cells.

According to a particular aspect, the invention relates to an isolated humanized antibody or an antigen-binding fragment thereof that binds to a phosphorylated tau protein at an epitope in the proline rich domain of the tau protein. In a more particular aspect, the invention relates to an isolated humanized antibody or an antigen-binding fragment thereof that binds to a phosphorylated tau protein at an epitope comprising phosphorylated T212 and/or T217 residues. In a more particular aspect, the invention relates to an isolated monoclonal antibody or an antigen-binding fragment thereof that binds to a phosphorylated epitope of any of SEQ ID NOs: 48, 52, and 54. In an even more particular aspect, the invention relates to an isolated monoclonal antibody or an antigen-binding fragment thereof that binds to a phosphorylated epitope of SEQ ID NO: 48. The antibody of the invention can a be a humanized antibody.

Table 1 shows the heavy and light chain variable regions for 5 humanized mAbs that bind to phopho tau by SEQ ID NO. Heavy and light chain sequences are also shown for humanized mAb B296. This mAb was affinity matured (see Table 3).

Table 2 shows antigen-binding site residues (i.e., CDR regions) of exemplary antibodies of the invention defined according to Chothia, ABM, Kabat and IMGT numbering schemes. Amino acid sequences of exemplary heavy chain variable regions are shown in SEQ ID NOs: 26-29, and amino acid sequences of exemplary light chain variable regions are shown in SEQ ID NOs: 31-34.

Table 3 shows the sequences of affinity matured monoclonal antibodies generated from B296 (i.e., B333, B711 and B809). Variable region sequences are underlined in the heavy and light chain sequences. The bolded amino acids in the CDRs of the affinity matured monoclonal antibodies indicate a substitution as compared to the B296 CDR sequence. CDR sequences are determine by Kabat numbering schemes.

TABLE 1

| Humanized phospho tau mAbs | | | | |
|---|---|---|---|---|
| mAb | $V_H$ | $V_L$ | Heavy Chain | Light Chain |
| B235 | 26 | 31 | | |
| B252 | 28 | 34 | | |
| B280 | 26 | 34 | | |
| B282 | 28 | 31 | | |
| B296 | 27 | 31 | 45 | 46 |

TABLE 2

CDR sequences for the VH (VH10) and VL (VL7) domains of the humanized anti-PHF-tau antibody B296

| V-region ID | CDR-1 | CDR-2 | CDR-3 |
|---|---|---|---|
| Chothia numbering scheme | | | |
| VH10 | GFTFSSY (SEQ ID NO: 1) | SKGGN (SEQ ID NO: 2) | GWGDYGWFAY (SEQ ID NO: 3) |
| VL7 | KASQDINRYLN (SEQ ID NO: 13) | RANRLLD (SEQ ID NO: 14) | LQYDEFPLT (SEQ ID NO: 15) |
| ABM numbering scheme | | | |
| VH10 | GFTFSSYAMS (SEQ ID NO: 4) | SISKGGNTY (SEQ ID NO: 5) | GWGDYGWFAY (SEQ ID NO: 6) |

TABLE 2-continued

CDR sequences for the VH (VH10) and VL (VL7) domains of the humanized anti-PHF-tau antibody B296

| V-region ID | CDR-1 | CDR-2 | CDR-3 |
|---|---|---|---|
| VL7 | KASQDINRYLN (SEQ ID NO: 16) | RANRLLD (SEQ ID NO: 17) | LQYDEFPLT (SEQ ID NO: 18) |

Kabat numbering scheme

| | | | |
|---|---|---|---|
| VH10 | SYAMS (SEQ ID NO: 7) | SISKGGNTYYADSVKG (SEQ ID NO: 8) | GWGDYGWFAY (SEQ ID NO: 9) |
| VL7 | KASQDINRYLN (SEQ ID NO: 19) | RANRLLD (SEQ ID NO: 20) | LQYDEFPLT (SEQ ID NO: 21) |

IMGT numbering scheme

| | | | |
|---|---|---|---|
| VH10 | GFTFSSYA (SEQ ID NO: 10) | ISKGGNT (SEQ ID NO: 11) | ARGWGDYGWFAYW (SEQ ID NO: 12) |
| VL7 | QDINRY (SEQ ID NO: 22) | RAN (SEQ ID NO: 23) | LQYDEFPLT (SEQ ID NO: 24) |

TABLE 3

Affinity Matured B296

| mAb | | Name | SEQ ID NO | Sequence |
|---|---|---|---|---|
| PT1B333 | V<sub>H</sub> | CDR1 | 80 | SSYAMS |
| | | CDR2 | 81 | SISKGGNTYYADSVKG |
| | | CDR3 | 9 | GWGDYGWFAY |
| | | Heavy Chain | 74 | QVQLVESGGGVVQPGRSLRLSCAASGFTFSSYAMSWVRQAPGKGLE WVASISKGGNTYYADSVKGRFTISRDNSKNTLYLQMNSLRAEDTAV YYCARGWGDYGWFAYWGQVTLVTVSSASTKGPSVFPLAPSSKSTSG GTAALGCLVKDYFPEPVTVSWNSGALTSGVHTFPAVLQSSGLYSLS SVVTVPSSSLGTQTYICNVNHKPSNTKVDKKVEPKSCDKTHTCPPC PAPELLGGPSVFLFPPKPKDTLMISRTPEVTCVVVDVSHEDPEVKF NWYVDGVEVHNAKTKPREEQYNSTYRVVSVLTVLHQDWLNGKEYKC KVSNKALPAPIEKTISKAKGQPREPQVYTLPPSREEMTKNQVSLT CLVKGFYPSDIAVEWESNGQPENNYKTTPPVLDSDGSFFLYSKLT VDKSRWQQGNVFSCSVMHEALHNHYTQKSLSLSPGK |
| | V<sub>L</sub> | CDR1 | 70 | KASQDINRWLN |
| | | CDR2 | 20 | RANRLLD |
| | | CDR3 | 21 | LQYDEFPLT |
| | | Light Chain | 75 | DIQMTQSPSSLSASVGDRVTITCKASQDINRWLNWFQQKPGKAPK SLIYRANRLLDGVPSRFSGSGSGTDFTLTISSLQPEDFATYYCLQ YDEFPLTFGQGTKLEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| PT1B711 | V<sub>H</sub> | CDR1 | 71 | TSYAMS |
| | | CDR2 | 72 | SITKGGNTYYADSVKG |
| | | CDR3 | 73 | GWGIYGWFAY |
| | | Heavy Chain | 76 | QVQLVESGGGVVQPGRSLRLSCAASGFTFTSYAMSWVRQAPGK GLEWVASITKGGNTYYADSVKGRFTISRDNSKNTLYLQMNSLR AEDTAVYYCARGWGIYGWFAYWGQVTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| | V<sub>L</sub> | CDR1 | 70 | KASQDINRWLN |
| | | CDR2 | 20 | RANRLLD |
| | | CDR3 | 21 | LQYDEFPLT |
| | | Light Chain | 77 | DIQMTQSPSSLSASVGDRVTITCKASQDINRWLNWFQQKPGKAP KSLIYRANRLLDGVPSRFSGSGSGTDFTLTISSLQPEDFATYYC LQYDEFPLTFGQGTKLEIKRTVAAPSVFIFPPSDEQLKSGTASV VCLLNNFYPREAKVQWKVDNALQSGNSQESVTEQDSKDSTYSLSS TLTLSKADYEKHKVYACEVTHQGLSSPVTKSFNRGEC |

TABLE 3-continued

Affinity Matured B296

| mAb | Name | SEQ ID NO | Sequence |
|---|---|---|---|
| PT1B809 | V$_H$ CDR1 | 71 | TSYAMS |
| | CDR2 | 72 | SITKGGNTYYADSVKG |
| | CDR3 | 73 | GWGIYGWFAY |
| | Heavy Chain | 78 | QVQLVESGGGVVQPGRSLRLSCAASGFTFTSYAMSWVRQAPG KGLEWVASITKGGNTYYADSVKGRFTISRDNSKNTLYLQMNS LRAEDTAVYYCARGWGIYGWFAYWGQVTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPELLGGPSVFLFPPKPKDTLMISR TPEVTCVVVDVSHEDPEVKFNWYVDGVEVHNAKTKPREEQYN STYRVVSVLTVLHQDWLNGKEYKCKVSNKALPAPIEKTISKAK GQPREPQVYTLPPSREEMTKNQVSLTCLVKGFYPSDIAVEWES NGQPENNYKTTPPVLDSDGSFFLYSKLTVDKSRWQQGNVFSCS VMHEALHNHYTQKSLSLSPGK |
| | V$_L$ CDR1 | 19 | KASQDINRYLN |
| | CDR2 | 20 | RANRLLD |
| | CDR3 | 21 | LQYDEFPLT |
| | Light Chain | 79 | DIQMTQSPSSLSASVGDRVTITCKASQDINRYLNWFQQKPG KAPKSLIYRANRLLDGVPSRFSGSGSGTDFTLTISSLQPED FATYYCLQYDEFPLTFGQGTKLEIKRTVAAPSVFIFPPSDE QLKSGTASVVCLLNNFYPREAKVQWKVDNALQSGNSQESVTE QDSKDSTYSLSSTLTLSKADYEKHKVYACEVTHQGLSSPVTK SFNRGEC |

Humanized antibodies have variable region framework residues substantially from a human antibody (termed an acceptor antibody) and complementarity determining regions substantially from a non-human antibody (i.e., mouse-antibody), (referred to as the donor immunoglobulin). See Queen et al., *Proc. Natl. Acad. Sci. USA*. 86:10029-10033, 1989, WO 90/07861, U.S. Pat. Nos. 5,693,762, 5,693,761, 5,585,089, 5,530,101, and 5,225,539. The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid: (1) noncovalently binds antigen directly, (2) is adjacent to a CDR region, (3) otherwise interacts with a CDR region (e.g. is within about 6 angstroms of a CDR region), or (4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

Antibody humanization can be accomplished using well known methods, such as specificity determining residues resurfacing (SDRR) (US2010/0261620), resurfacing (Padlan et al., *Mol. Immunol.* 28:489-98, 1991), super humanization (WO 04/006955) and human string content optimization (U.S. Pat. No. 7,657,380). Human framework sequences useful for grafting or humanization can be selected from relevant databases by those skilled in the art. The selected frameworks can further be modified to preserve or enhance binding affinity by techniques such as those disclosed in Queen et al., 1989, Id. According to particular embodiments, methods for humanizing anti-PHF-tau antibodies from mouse parental antibodies include those described in Example 4 below.

Antibodies of the present invention can be produced by a variety of techniques, for example by the hybridoma method (Kohler and Milstein, *Nature*. 256:495-7, 1975). Chimeric monoclonal antibodies containing a light chain and heavy chain variable region derived from a donor antibody (typically murine) in association with light and heavy chain constant regions derived from an acceptor antibody (typically another mammalian species such as human) can be prepared by a method disclosed in U.S. Pat. No. 4,816,567. CDR-grafted monoclonal antibodies having CDRs derived from a non-human donor immunoglobulin (typically murine) and the remaining immunoglobulin-derived parts of the molecule being derived from one or more human immunoglobulins can be prepared by techniques known to those skilled in the art such as that disclosed in U.S. Pat. No. 5,225,539. Fully human monoclonal antibodies lacking any non-human sequences can be prepared from human immunoglobulin transgenic mice by techniques referenced in (Lonberg et al., *Nature.* 368:856-9, 1994; Fishwild et al., *Nat Biotechnol.* 14:845-51, 1996; Mendez et al., *Nat Genet.* 15:146-56, 1997). Human monoclonal antibodies can also be prepared and optimized from phage display libraries (Knappik et al., *J Mol Biol.* 296:57-86, 2000; Krebs et al., *J Immunol Methods.* 254:67-84, 2001; Shi et al., *J Mol Biol.* 397:385-96, 2010).

Monoclonal antibodies of the invention comprising an antibodies having an HCDR1 of any of SEQ ID NOs: 1, 4, 7, 10, 71, 80; an HCDR2 of any of SEQ ID NOs: 2, 5, 8, 11, 72, 81; an HCDR3 of any of SEQ ID NOs: 3, 6, 9, 12, 73; an LCDR1 of any of SEQ ID NOs: 13, 16, 19, 22, 70; an LCDR2 of any of SEQ ID NOs: 14, 17, 20, 23; an LCDR3 of any of SEQ ID NOs: 15, 18, 21, 24. The invention also encompasses monoclonal antibodies that have CDR sequences that are at least 90%, more preferably at least 95%, more preferably at least 98% identical, more preferably at least 99% identical to an HCDR1 of any of SEQ ID NOs: 1, 4, 7, 10, 71, 80; an HCDR2 of any of SEQ ID NOs: 2, 5, 8, 11, 72, 81; an HCDR3 of any of SEQ ID NOs: 3, 6, 9, 12, 73; an LCDR1 of any of SEQ ID NOs: 13, 16, 19, 22, 70; an LCDR2 of any of SEQ ID NOs: 14, 17, 20, 23; an LCDR3 of any of SEQ ID NOs: 15, 18, 21, 24.

According to a particular aspect, the invention relates to an isolated humanized antibodies or antigen-binding fragments thereof comprising:

(1) HCDR1, HCDR2 and HCDR3 having the polypeptide sequences of SEQ ID NOs: 4, 5 and 6, respectively LCDR1, LCDR2 and LCDR3 having the polypeptide sequences of SEQ ID NOs: 16, 17 and 18, respectively;
(2) HCDR1, HCDR2 and HCDR3 having the polypeptide sequences of SEQ ID NOs: 1, 2 and 3, respectively and LCDR1, LCDR2 and LCDR3 having the polypeptide sequences of SEQ ID NOs: 13, 14 and 15, respectively;
(3) HCDR1, HCDR2 and HCDR3 having the polypeptide sequences of SEQ ID NOs: 7, 8 and 9, respectively and LCDR1, LCDR2 and LCDR3 having the polypeptide sequences of SEQ ID NOs: 19, 20 and 21, respectively;
(4) HCDR1, HCDR2 and HCDR3 having the polypeptide sequences of SEQ ID NOs: 10, 11 and 12, respectively and LCDR1, LCDR2 and LCDR3 having the polypeptide sequences of SEQ ID NOs: 22, 23 and 24, respectively;
(5) HCDR1, HCDR2 and HCDR3 having the polypeptide sequences of SEQ ID NOs:80, 81 and 9, respectively and LCDR1, LCDR2 and LCDR3 having the polypeptide sequences of SEQ ID NOs: 70, 20 and 21, respectively;
(6) HCDR1, HCDR2 and HCDR3 having the polypeptide sequences of SEQ ID NOs: 71, 72, 73, respectively and LCDR1, LCDR2 and LCDR3 having the polypeptide sequences of SEQ ID NOs: 70, 20 and 21, respectively;
(7) HCDR1, HCDR2 and HCDR3 having the polypeptide sequences of SEQ ID NOs: 71, 72 and 73, respectively and LCDR1, LCDR2 and LCDR3 having the polypeptide sequences of SEQ ID NOs: 19, 20 and 21, respectively;
(8) HCDR1, HCDR2 and HCDR3 of a $V_H$ region having the polypeptide sequence of SEQ ID NO: 26 and LCDR1, LCDR2 and LCDR3 of a $V_L$ region having the polypeptide sequence of SEQ ID NO: 31;
(9) HCDR1, HCDR2 and HCDR3 of a $V_H$ region having the polypeptide sequence of SEQ ID NO: 28 and LCDR1, LCDR2 and LCDR3 of a $V_L$ region having the polypeptide sequence of SEQ ID NO: 34;
(10) HCDR1, HCDR2 and HCDR3 of a $V_H$ region having the polypeptide sequence of SEQ ID NO: 26 and LCDR1, LCDR2 and LCDR3 of a $V_L$ region having the polypeptide sequence of SEQ ID NO: 34; or
(11) HCDR1, HCDR2 and HCDR3 of a $V_H$ region having the polypeptide sequence of SEQ ID NO: 28 and LCDR1, LCDR2 and LCDR3 of a $V_L$ region having the polypeptide sequence of SEQ ID NO: 31;

wherein the antibody or antigen-binding fragment thereof binds PHF-tau, preferably human PHF-tau, and wherein the framework regions in the heavy chain variable region domain and in the light chain variable region domain comprise amino acid sequences from a human immunoglobulin.

According to another particular aspect, the invention relates to an isolated humanized antibody or antigen-binding fragment thereof comprising a heavy chain variable region having a polypeptide sequence at least 80%, preferably at least 85%, preferably at least 90%, more preferably at least 95%, more preferably at least 98% identical, and most preferably 100% identical to SEQ ID NO: 26, 27, 28 or 29, or a light chain variable region having a polypeptide sequence at least 80%, preferably at least 85%, preferably at least 90%, more preferably at least 95%, more preferably at least 98% identical, and most preferably 100% identical to SEQ ID NO: 31, 32, 33 or 34.

According to another particular aspect, the invention relates to an isolated humanized antibody or antigen-binding fragment thereof comprising a heavy chain variable region having a polypeptide sequence at least 80%, preferably at least 85%, preferably at least 90%, more preferably at least 95%, more preferably at least 98% identical, and most preferably 100% identical to the variable region in a heavy chain of any of SEQ ID NO: 74, 76, and 78, or a light chain variable region having a polypeptide sequence at least 80%, preferably at least 85%, preferably at least 90%, more preferably at least 95%, more preferably at least 98% identical, and most preferably 100% identical to the variable region in a light chain of any of SEQ ID NOs: 75, 77, and 79.

According to another particular aspect, the invention relates to an isolated humanized antibody or antigen-binding fragment thereof comprising a heavy chain variable region having the polypeptide sequence at least 80%, preferably at least 85%, preferably at least 90%, more preferably at least 95%, more preferably at least 98% identical, and most preferably 100% identical to SEQ ID NO: 26, and a light chain variable region having the polypeptide sequence at least 80%, preferably at least 85%, preferably at least 90%, more preferably at least 95%, more preferably at least 98% identical, and most preferably 100% identical to SEQ ID NO: 31.

According to another particular aspect, the invention relates to an isolated humanized antibody or antigen-binding fragment thereof comprising a heavy chain variable region having the polypeptide sequence at least 80%, preferably at least 85%, preferably at least 90%, more preferably at least 95%, more preferably at least 98% identical, and most preferably 100% identical to SEQ ID NO: 28, and a light chain variable region having the polypeptide sequence at least 80%, preferably at least 85%, preferably at least 90%, more preferably at least 95%, more preferably at least 98% identical, and most preferably 100% identical to SEQ ID NO: 34.

According to another particular aspect, the invention relates to an isolated humanized antibody or antigen-binding fragment thereof comprising a heavy chain variable region having the polypeptide sequence at least 80%, preferably at least 85%, preferably at least 90%, more preferably at least 95%, more preferably at least 98% identical, and most preferably 100% identical to SEQ ID NO: 26, and a light chain variable region having the polypeptide sequence at least 80%, preferably at least 85%, preferably at least 90%, more preferably at least 95%, more preferably at least 98% identical, and most preferably 100% identical to SEQ ID NO: 34.

According to another particular aspect, the invention relates to an isolated humanized antibody or antigen-binding fragment thereof comprising a heavy chain variable region having the polypeptide sequence at least 80%, preferably at least 85%, preferably at least 90%, more preferably at least 95%, more preferably at least 98% identical, and most preferably 100% identical to SEQ ID NO: 28, and a light chain variable region having the polypeptide sequence at least 80%, preferably at least 85%, preferably at least 90%, more preferably at least 95%, more preferably at least 98% identical, and most preferably 100% identical to SEQ ID NO: 31.

According to another particular aspect, the invention relates to an isolated humanized antibody or antigen-binding fragment thereof comprising a heavy chain variable region having the polypeptide sequence at least 80%, preferably at least 85%, preferably at least 90%, more preferably at least 95%, more preferably at least 98% identical, and most preferably 100% identical to SEQ ID NO: 27, and a light chain variable region having the polypeptide sequence at least 80%, preferably at least 85%, preferably at least 90%, more preferably at least 95%, more preferably at least 98% identical, and most preferably 100% identical to SEQ ID NO: 31.

According to another particular aspect, the invention relates to an isolated humanized antibody or antigen-binding fragment thereof comprising a heavy chain variable region having the polypeptide sequence at least 80%, preferably at least 85%, preferably at least 90%, more preferably at least 95%, more preferably at least 98% identical, and most preferably 100% identical to the variable region in the heavy chain of SEQ ID NO: 74, and a light chain variable region having the polypeptide sequence at least 80%, preferably at least 85%, preferably at least 90%, more preferably at least 95%, more preferably at least 98% identical, and most preferably 100% identical to the variable region in the light chain of SEQ ID NO: 75.

According to another particular aspect, the invention relates to an isolated humanized antibody or antigen-binding fragment thereof comprising a heavy chain variable region having the polypeptide sequence at least 80%, preferably at least 85%, preferably at least 90%, more preferably at least 95%, more preferably at least 98% identical, and most preferably 100% identical to the variable region in the heavy chain of SEQ ID NO: 76, and a light chain variable region having the polypeptide sequence at least 80%, preferably at least 85%, preferably at least 90%, more preferably at least 95%, more preferably at least 98% identical, and most preferably 100% identical to the variable region in the light chain of SEQ ID NO: 77.

According to another particular aspect, the invention relates to an isolated humanized antibody or antigen-binding fragment thereof comprising a heavy chain variable region having the polypeptide sequence at least 80%, preferably at least 85%, preferably at least 90%, more preferably at least 95%, more preferably at least 98% identical, and most preferably 100% identical to the variable region in the heavy chain of SEQ ID NO: 78, and a light chain variable region having the polypeptide sequence at least 80%, preferably at least 85%, preferably at least 90%, more preferably at least 95%, more preferably at least 98% identical, and most preferably 100% identical to the variable region in the light chain of SEQ ID NO: 79.

According to another particular aspect, the invention relates to an isolated humanized antibody or antigen-binding fragment thereof comprising a heavy chain having a polypeptide sequence at least 80%, preferably at least 85%, preferably at least 90%, more preferably at least 95%, more preferably at least 98% identical, and most preferably 100% identical to SEQ ID NO: 45 and a light chain having a polypeptide sequence at least 80%, preferably at least 85%, preferably at least 90%, more preferably at least 95%, more preferably at least 98% identical, and most preferably 100% identical to SEQ ID NO: 46. According to another particular aspect, the invention relates to an isolated humanized antibody or antigen-binding fragment thereof comprising a heavy chain having the polypeptide sequence of SEQ ID NO: 45 and a light chain having the polypeptide sequence of SEQ ID NO: 46.

According to another particular aspect, the invention relates to an isolated humanized antibody or antigen-binding fragment thereof comprising a heavy chain having a polypeptide sequence at least 80%, preferably at least 85%, preferably at least 90%, more preferably at least 95%, more preferably at least 98% identical, and most preferably 100% identical to SEQ ID NO: 74 and a light chain having a polypeptide sequence at least 80%, preferably at least 85%, preferably at least 90%, more preferably at least 95%, more preferably at least 98% identical, and most preferably 100% identical to SEQ ID NO: 75. According to another particular aspect, the invention relates to an isolated humanized antibody or antigen-binding fragment thereof comprising a heavy chain having the polypeptide sequence of SEQ ID NO: 74 and a light chain having the polypeptide sequence of SEQ ID NO: 75.

According to another particular aspect, the invention relates to an isolated humanized antibody or antigen-binding fragment thereof comprising a heavy chain having a polypeptide sequence at least 80%, preferably at least 85%, preferably at least 90%, more preferably at least 95%, more preferably at least 98% identical, and most preferably 100% identical to SEQ ID NO: 76 and a light chain having a polypeptide sequence at least 80%, preferably at least 85%, preferably at least 90%, more preferably at least 95%, more preferably at least 98% identical, and most preferably 100% identical to SEQ ID NO: 77. According to another particular aspect, the invention relates to an isolated humanized antibody or antigen-binding fragment thereof comprising a heavy chain having the polypeptide sequence of SEQ ID NO: 76 and a light chain having the polypeptide sequence of SEQ ID NO: 77.

According to another particular aspect, the invention relates to an isolated humanized antibody or antigen-binding fragment thereof comprising a heavy chain having a polypeptide sequence at least 80%, preferably at least 85%, preferably at least 90%, more preferably at least 95%, more preferably at least 98% identical, and most preferably 100% identical to SEQ ID NO: 78 and a light chain having a polypeptide sequence at least 80%, preferably at least 85%, preferably at least 90%, more preferably at least 95%, more preferably at least 98% identical, and most preferably 100% identical to SEQ ID NO: 79. According to another particular aspect, the invention relates to an isolated humanized antibody or antigen-binding fragment thereof comprising a heavy chain having the polypeptide sequence of SEQ ID NO: 78 and a light chain having the polypeptide sequence of SEQ ID NO: 79.

According to another particular aspect, the invention relates to an isolated humanized antibody or antigen-binding fragment thereof comprising a human heavy chain IgG1 constant region and a human light chain kappa constant region.

According to another particular aspect, the invention relates to an isolated humanized antibody or antigen-binding fragment thereof, wherein the antibody or antigen-binding fragment binds to human PHF-tau with a dissociation constant ($K_D$) of $5\times10^{-9}$ M or less, preferably a $K_D$ of $1\times10^{-9}$ M or less or $1\times10^{-10}$ M or less, wherein the $K_D$ is measured by surface plasmon resonance analysis, such as by using a Biacore or ProteOn system.

The functional activity of humanized antibodies and antigen-binding fragments thereof that bind PHF-tau can be characterized by methods known in the art and as described herein. Methods for characterizing antibodies and antigen-binding fragments thereof that bind PHF-tau include, but are not limited to, affinity and specificity assays including Biacore, ELISA, and FACS analysis; immunohistochemistry analysis; in vitro cellular assays and in vivo injection assays to determine the efficacy of the antibodies in inhibiting tau seeding; cell cytotoxicity assays to detect the presence of antibody-dependent cell-mediated cytotoxicity (ADCC), and complement dependent cytotoxicity (CDC) activity of the antibodies; etc. According to particular embodiments, methods for characterizing antibodies and antigen-binding fragments thereof that bind PHF-tau include those described in Examples 5, 6, 8 and 9 below. An exemplary mouse parental antibody of humanized antibodies binding PHF-tau but not control tau is antibody PT3, which has a heavy chain variable region of SEQ ID NO: 25 and a light chain variable region of SEQ ID NO: 30 (see e.g., U.S. Pat. No. 9,371,376 which is incorporated by reference in its entirety).

Several well-known methodologies can be employed to determine the binding epitope of the antibodies of the invention. For example, when the structures of both individual components are known, in silico protein-protein docking can be carried out to identify compatible sites of interaction. Hydrogen-deuterium (H/D) exchange can be carried out with the antigen and antibody complex to map regions on the antigen that are bound by the antibody. Segment and point mutagenesis of the antigen can be used to locate amino acids important for antibody binding. The co-crystal structure of an antibody-antigen complex is used to identify residues contributing to the epitope and paratope. According to particular embodiments, methods for determining the binding epitope of antibodies of the invention include those described in Examples 2, 3 and 7 below.

Antibodies of the invention can be bispecific or multispecific. An exemplary bispecific antibody can bind two distinct epitopes on PHF-tau or can bind PHF-tau and amyloid beta (Abeta). Another exemplary bispecific antibody can bind PHF-tau and an endogenous blood-brain barrier transcytosis receptor such as insulin receptor, transferring receptor, insulin-like growth factor-1 receptor, and lipoprotein receptor. An exemplary antibody is of IgG1 type.

Immune effector properties of the antibodies of the invention can be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), phagocytosis, down regulation of cell surface receptors (e.g., B cell receptor; BCR), etc. can be provided and/or controlled by modifying residues in the Fc responsible for these activities. Pharmacokinetic properties can also be enhanced by mutating residues in the Fc domain that extend antibody half-life (Strohl, *Curr Opin Biotechnol.* 20:685-91, 2009).

Additionally, antibodies of the invention can be post-translationally modified by processes such as glycosylation, isomerization, deglycosylation or non-naturally occurring covalent modification such as the addition of polyethylene glycol moieties and lipidation. Such modifications can occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function (Knight et al., *Platelets.* 15:409-18, 2004; Leong et al., *Cytokine.* 16:106-19, 2001; Yang et al., *Protein Eng.* 16:761-70, 2003).

In another general aspect, the invention relates to an isolated polynucleotide encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding humanized antibodies or antigen-binding fragments thereof of the invention can be altered without changing the amino acid sequences of the proteins. Exemplary isolated polynucleotides are polynucleotides encoding polypeptides comprising immunoglobulin heavy chain CDRs HCDR1, HCDR2 and HCDR3 shown in SEQ ID NOs: 4, 5 and 6, respectively, or polypeptides comprising immunoglobulin light chain CDRs LCDR1, LCDR2 and LCDR3 shown in SEQ ID NOs: 16, 17 and 18, respectively. Other exemplary isolated polynucleotides are polynucleotides having the sequences shown in SEQ ID NOs: 36-39 or 41-44, encoding antibody variable regions of the invention. Other polynucleotides which, given the degeneracy of the genetic code or codon preferences in a given expression system, encode the antibodies of the invention are also within the scope of the invention. The isolated nucleic acids of the present invention can be made using well known recombinant or synthetic techniques. DNA encoding the monoclonal antibodies is readily isolated and sequenced using methods known in the art. Where a hybridoma is produced, such cells can serve as a source of such DNA. Alternatively, display techniques wherein the coding sequence and the translation product are linked, such as phage or ribosomal display libraries, can be used.

In another general aspect, the invention relates to a vector comprising an isolated polynucleotide encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated polynucleotide encoding a monoclonal antibody or antigen-binding fragment thereof of the invention. Any host cell known to those skilled in the art in view of the present disclosure can be used for recombinant expression of antibodies or antigen-binding fragments thereof of the invention. Such host cells can be eukaryotic cells, bacterial cells, plant cells or archaeal cells. Exemplary eukaryotic cells can be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1 SV (Lonza Biologics), CHO-K1 (ATCC CRL-61, Invitrogen) or DG44.

In another general aspect, the invention relates to a method of producing a monoclonal antibody or antigen-binding fragment thereof of the invention, comprising culturing a cell comprising a polynucleotide encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art.

Pharmaceutical Compositions and Methods of Treatment

Anti-PHF-tau antibodies of the invention or fragments thereof of the invention can be used to treat, reduce or prevent symptoms in patients having a neurodegenerative disease that involves pathological aggregation of tau within the brain, or a tauopathy, such as patients suffering from AD.

Thus, in another general aspect, the invention relates to a pharmaceutical composition comprising an isolated monoclonal antibody or antigen-binding fragment thereof of the invention and a pharmaceutically acceptable carrier.

In another general aspect, the invention relates to a method of treating or reducing symptoms of a disease, disorder or condition, such as a tauopathy, in a subject in need thereof, comprising administering to the subject a pharmaceutical composition of the invention.

In another general aspect, the invention relates to a method of reducing pathological tau aggregation or spreading of tauopathy in a subject in need thereof, comprising administering to the subject a pharmaceutical composition of the invention.

According to embodiments of the invention, the pharmaceutical composition comprises a therapeutically effective amount of the monoclonal anti-PHF-tau antibody or antigen-binding fragment thereof. As used herein with reference to humanized anti-PHF-tau antibodies or antigen-binding fragments thereof, a therapeutically effective amount means an amount of the monoclonal anti-PHF-tau antibody or antigen-binding fragment thereof that results in treatment of a disease, disorder, or condition; prevents or slows the progression of the disease, disorder, or condition; or reduces or completely alleviates symptoms associated with the immune disease, disorder, or condition.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

According to particular embodiments, the disease, disorder or condition to be treated is a tauopathy. According to more particular embodiments, the disease, disorder or condition to be treated, includes, but is not limited to, familial Alzheimer's disease, sporadic Alzheimer's disease, frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, or dementia pugulistica (boxing disease).

A tauopathy-related behavioral phenotype includes, but is not limited to, cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

Patients amenable to treatment include, but are not limited to, asymptomatic individuals at risk of AD or other tauopathy, as well as patients presently showing symptoms. Patients amenable to treatment include individuals who have a known genetic risk of AD, such as a family history of AD or presence of genetic risk factors in the genome. Exemplary risk factors are mutations in the amyloid precursor protein (APP), especially at position 717 and positions 670 and 671 (Hardy and Swedish mutations, respectively). Other risk factors are mutations in the presenilin genes PS1 and PS2 and in ApoE4, family history of hypercholesterolemia or atherosclerosis. Individuals presently suffering from AD can be recognized from characteristic dementia by the presence of risk factors described above. In addition, a number of diagnostic tests are available to identify individuals who have AD. These include measurement of cerebrospinal fluid tau and Abeta 42 levels. Elevated tau and decreased Abeta 42 levels signify the presence of AD. Individuals suffering from AD can also be diagnosed by AD and Related Disorders Association criteria.

Anti-PHF-tau antibodies of the invention are suitable both as therapeutic and prophylactic agents for treating or preventing neurodegenerative diseases that involve pathological aggregation of tau, such as AD or other tauopathies. In asymptomatic patients, treatment can begin at any age (e.g., at about 10, 15, 20, 25, 30 years). Usually, however, it is not necessary to begin treatment until a patient reaches about 40, 50, 60, or 70 years. Treatment typically entails multiple dosages over a period of time. Treatment can be monitored by assaying antibody, or activated T-cell or B-cell responses to the therapeutic agent over time. If the response falls, a booster dosage can be indicated.

In prophylactic applications, pharmaceutical compositions or medicaments are administered to a patient susceptible to, or otherwise at risk of, AD in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions or medicaments are administered to a patient suspected of, or already suffering from, such a disease in an amount sufficient to reduce, arrest, or delay any of the symptoms of the disease (biochemical, histologic and/or behavioral). Administration of a therapeutic can reduce or eliminate mild cognitive impairment in patients that have not yet developed characteristic Alzheimer's pathology.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

The antibodies of the invention can be prepared as pharmaceutical compositions containing a therapeutically effective amount of the antibody as an active ingredient in a pharmaceutically acceptable carrier. The carrier can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They can be sterilized by conventional, well-known sterilization techniques (e.g., filtration). The compositions can contain pharmaceutically acceptable auxiliary substances as required to approximate physiological conditions such as pH adjusting and buffering agents, stabilizing, thickening, lubricating and coloring agents, etc. The concentration of the antibodies of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected.

The mode of administration for therapeutic use of the antibodies of the invention can be any suitable route that delivers the agent to the host. For example, the compositions described herein can be formulated to be suitable for parenteral administration, e.g., intradermal, intramuscular, intraperitoneal, intravenous, subcutaneous, intranasal or intracranial administration, or they can be administered into the cerebrospinal fluid of the brain or spine.

The treatment can be given in a single dose schedule, or as a multiple dose schedule in which a primary course of treatment can be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The antibodies of the invention can be lyophilized for storage and reconstituted in a suitable carrier prior to use. This technique has been shown to be effective with antibody and other protein preparations and art-known lyophilization and reconstitution techniques can be employed.

According to particular embodiments, a composition used in the treatment of a tauopathy can be used in combination with other agents that are effective for treatment of related neurodegenerative diseases. In the case of AD, antibodies of the invention can be administered in combination with agents that reduce or prevent the deposition of amyloid-beta (Abeta). It is possible that PHF-tau and Abeta pathologies are synergistic. Therefore, combination therapy targeting the clearance of both PHF-tau and Abeta and Abeta-related pathologies at the same time can be more effective than targeting each individually. In the case of Parkinson's Disease and related neurodegenerative diseases, immune modulation to clear aggregated forms of the alpha-synuclein protein is also an emerging therapy. A combination therapy which targets the clearance of both tau and alpha-synuclein proteins simultaneously can be more effective than targeting either protein individually.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Diagnostic Methods and Kits

Monoclonal anti-PHF-tau antibodies of the invention can be used in methods of diagnosing AD or other tauopathies in a subject.

Thus, in another general aspect, the invention relates to methods of detecting the presence of PHF-tau in a subject and methods of diagnosing tauopathies in a subject by detecting the presence of PHF-tau in the subject using a monoclonal antibody or antigen-binding fragment thereof of the invention.

Phosphorylated tau can be detected in a biological sample from a subject (e.g., blood, serum, plasma, interstitial fluid, or cerebral spinal fluid sample) by contacting the biological sample with the diagnostic antibody reagent, and detecting binding of the diagnostic antibody reagent to phosphorylated tau in the sample from the subject. Assays for carrying out the detection include well-known methods such as ELISA, immunohistochemistry, western blot, or in vivo imaging. An exemplary diagnostic antibody is antibody PT3 of the invention.

Diagnostic antibodies or similar reagents can be administered by intravenous injection into the body of the patient, or directly into the brain by any suitable route that delivers the agent to the host. The dosage of antibody should be within the same ranges as for treatment methods. Typically, the antibody is labeled, although in some methods, the primary antibody with affinity for phosphorylated tau is unlabeled, and a secondary labeling agent is used to bind to the primary antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled PHF-tau, tau aggregates, and/or neurofibrillary tangles in a sample from the subject or in the subject, to corresponding baseline values. The baseline values can represent the mean levels in a population of healthy individuals. Baseline values can also represent previous levels determined in the same subject.

The diagnostic methods described above can also be used to monitor a subject's response to therapy by detecting the presence of phosphorylated tau in a subject before, during or after the treatment. A decrease in values relative to baseline signals a positive response to treatment. Values can also increase temporarily in biological fluids as pathological tau is being cleared from the brain.

The present invention is further directed to a kit for performing the above described diagnostic and monitoring methods. Typically, such kits contain a diagnostic reagent such as the antibodies of the invention, and optionally a detectable label. The diagnostic antibody itself can contain the detectable label (e.g., fluorescent molecule, biotin, etc.) which is directly detectable or detectable via a secondary reaction (e.g., reaction with streptavidin). Alternatively, a second reagent containing the detectable label cab be used, where the second reagent has binding specificity for the primary antibody. In a diagnostic kit suitable for measuring PHF-tau in a biological sample, the antibodies of the kit can be supplied pre-bound to a solid phase, such as to the wells of a microtiter dish.

The contents of all cited references (including literature references, issued patents, published patent applications, and co-pending patent applications) cited throughout this application are hereby expressly incorporated by reference.

EMBODIMENTS

The invention provides also the following non-limiting embodiments.

Embodiment 1 is an isolated monoclonal antibody or antigen-binding fragment thereof that binds to a phosphorylated tau protein at a phosphorylated epitope in the proline rich domain of the tau protein.

Embodiment 2 is an isolated monoclonal antibody or antigen-binding fragment thereof that binds to a phosphorylated tau protein at a phosphorylated epitope comprising phosphorylated T212 of the tau protein, preferably the isolated monoclonal antibody or antigen-binding fragment thereof binds to a phosphorylated epitope having or within the amino acid sequence of SEQ ID NO:54.

Embodiment 3 is an isolated monoclonal antibody or antigen-binding fragment thereof that binds to a phosphorylated tau protein at a phosphorylated epitope comprising phosphorylated T217 of the tau protein, preferably the isolated monoclonal antibody or antigen-binding fragment thereof binds to a phosphorylated epitope having or within the amino acid sequence of SEQ ID NO:52.

Embodiment 4 is an isolated monoclonal antibody or antigen-binding fragment thereof that binds to a phosphorylated tau protein at a phosphorylated epitope comprising phosphorylated T212 and phosphorylated T217 of the tau protein, preferably the isolated monoclonal antibody or antigen-binding fragment thereof binds to a phosphorylated epitope having or within the amino acid sequence of SEQ ID NO:48.

Embodiment 5 an isolated monoclonal antibody or antigen-binding fragment comprising:
(1) HCDR1, HCDR2 and HCDR3 having the polypeptide sequences of SEQ ID NOs: 4, 5 and 6, respectively LCDR1, LCDR2 and LCDR3 having the polypeptide sequences of SEQ ID NOs: 16, 17 and 18, respectively;
(2) HCDR1, HCDR2 and HCDR3 having the polypeptide sequences of SEQ ID NOs: 1, 2 and 3, respectively and LCDR1, LCDR2 and LCDR3 having the polypeptide sequences of SEQ ID NOs: 13, 14 and 15, respectively;
(3) HCDR1, HCDR2 and HCDR3 having the polypeptide sequences of SEQ ID NOs: 7, 8 and 9, respectively and LCDR1, LCDR2 and LCDR3 having the polypeptide sequences of SEQ ID NOs: 19, 20 and 21, respectively;
(4) HCDR1, HCDR2 and HCDR3 having the polypeptide sequences of SEQ ID NOs: 10, 11 and 12, respectively and LCDR1, LCDR2 and LCDR3 having the polypeptide sequences of SEQ ID NOs: 22, 23 and 24, respectively;
(5) HCDR1, HCDR2 and HCDR3 having the polypeptide sequences of SEQ ID NOs:80, 81 and 9, respectively and LCDR1, LCDR2 and LCDR3 having the polypeptide sequences of SEQ ID NOs: 70, 20 and 21, respectively;
(6) HCDR1, HCDR2 and HCDR3 having the polypeptide sequences of SEQ ID NOs: 71, 72, 73, respectively and LCDR1, LCDR2 and LCDR3 having the polypeptide sequences of SEQ ID NOs: 70, 20 and 21, respectively;
(7) HCDR1, HCDR2 and HCDR3 having the polypeptide sequences of SEQ ID NOs: 71, 72 and 73, respectively and LCDR1, LCDR2 and LCDR3 having the polypeptide sequences of SEQ ID NOs: 19, 20 and 21, respectively;
(8) HCDR1, HCDR2 and HCDR3 of a $V_H$ region having the polypeptide sequence of SEQ ID NO: 26 and LCDR1, LCDR2 and LCDR3 of a $V_L$ region having the polypeptide sequence of SEQ ID NO: 31;
(9) HCDR1, HCDR2 and HCDR3 of a $V_H$ region having the polypeptide sequence of SEQ ID NO: 28 and LCDR1, LCDR2 and LCDR3 of a $V_L$ region having the polypeptide sequence of SEQ ID NO: 34;
(10) HCDR1, HCDR2 and HCDR3 of a $V_H$ region having the polypeptide sequence of SEQ ID NO: 26 and LCDR1, LCDR2 and LCDR3 of a $V_L$ region having the polypeptide sequence of SEQ ID NO: 34; or
(11) HCDR1, HCDR2 and HCDR3 of a $V_H$ region having the polypeptide sequence of SEQ ID NO: 28 and LCDR1, LCDR2 and LCDR3 of a $V_L$ region having the polypeptide sequence of SEQ ID NO: 31;

wherein the antibody or antigen-binding fragment thereof binds PHF-tau, and wherein the framework regions in the heavy chain variable region domain and in the light chain variable region domain comprise amino acid sequences from a human immunoglobulin.

Embodiment 6 is an isolated monoclonal antibody or antigen-binding fragment comprising a heavy chain variable region having a polypeptide sequence at least 80%, preferably at least 85%, preferably at least 90%, more preferably at least 95%, more preferably at least 98% identical, and most preferably 100% identical to SEQ ID NO: 26, 27, 28 or 29, or a light chain variable region having a polypeptide sequence at least 80%, preferably at least 85%, preferably at least 90%, more preferably at least 95%, more preferably at least 98% identical, and most preferably 100% identical to SEQ ID NO: 31, 32, 33 or 34.

Embodiment 7 is an isolated monoclonal antibody or antigen-binding fragment comprising a heavy chain variable region having a polypeptide sequence at least 80%, preferably at least 85%, preferably at least 90%, more preferably at least 95%, more preferably at least 98% identical, and most preferably 100% identical to the variable region in a heavy chain of any of SEQ ID NO: 74, 76, and 78, or a light chain variable region having a polypeptide sequence at least 80%, preferably at least 85%, preferably at least 90%, more preferably at least 95%, more preferably at least 98% identical, and most preferably 100% identical to the variable region in a light chain of any of SEQ ID NOs: 75, 77, and 79.

Embodiment 8 is an isolated monoclonal antibody or antigen-binding fragment comprising:
(1) a $V_H$ having the polypeptide sequence of SEQ ID NO: 26 and a VL having the polypeptide sequence of SEQ ID NO: 31;
(2) a $V_H$ having the polypeptide sequence of SEQ ID NO: 28 and a VL having the polypeptide sequence of SEQ ID NO: 34;
(3) a $V_H$ having the polypeptide sequence of SEQ ID NO: 26 and a VL having the polypeptide sequence of SEQ ID NO: 34;
(4) a $V_H$ having the polypeptide sequence of SEQ ID NO: 28 and a VL having the polypeptide sequence of SEQ ID NO: 31;
(5) a $V_H$ having the polypeptide sequence of SEQ ID NO: 27 and a VL having the polypeptide sequence of SEQ ID NO: 31;
(6) a $V_H$ having the polypeptide sequence of the heavy chain of SEQ ID NO: 74 and a VL having the polypeptide sequence of the light chain of SEQ ID NO: 75;
(7) a $V_H$ having the polypeptide sequence of the heavy chain of SEQ ID NO: 76 and a VL having the polypeptide sequence of the light chain of SEQ ID NO: 77; or
(8) a $V_H$ having the polypeptide sequence of the heavy chain of SEQ ID NO: 78 and a VL having the polypeptide sequence of the light chain of SEQ ID NO: 79.

Embodiment 9 is an isolated monoclonal antibody or antigen-binding fragment comprising a heavy chain having the polypeptide sequence at least 80 preferably at least 85%, preferably at least 90%, more preferably at least 95%, more preferably at least 98% identical, and most preferably 100% identical to SEQ ID NO: 45 and a light chain having the polypeptide sequence at least 80%, preferably at least 85%, preferably at least 90%, more preferably at least 95%, more preferably at least 98% identical, and most preferably 100% identical to SEQ ID NO: 46.

Embodiment 10 is the isolated monoclonal antibody or antigen-binding fragment of any of Embodiments 1 to 9, comprising a human heavy chain IgG1 constant region and a human light chain kappa constant region.

Embodiment 11 is the isolated monoclonal antibody or antigen-binding fragment of any of Embodiments 1 to 10, wherein the antibody or antigen-binding fragment binds to human PHF-tau with a $K_D$ of $5\times10^{-9}$ M or less, preferably a $K_D$ of $1\times10^{-9}$ M or less or $1\times10^{-10}$ M or less, wherein the $K_D$ is measured by surface plasmon resonance analysis, such as by using a Biacore system.

Embodiment 12 is an isolated nucleic acid encoding the monoclonal antibody or antigen-binding fragment of any of Embodiments 1 to 12.

Embodiment 13 is a vector comprising the isolated nucleic acid of Embodiment 12.

Embodiment 14 is a host cell comprising the nucleic acid of Embodiment 13.

Embodiment 15 is a pharmaceutical composition comprising the isolated monoclonal antibody or antigen-binding fragment of any of Embodiments 1 to 11 and a pharmaceutically acceptable carrier.

Embodiment 16 is a method of reducing pathological tau aggregation or spreading of tauopathy in a subject in need thereof, comprising administering to the subject the pharmaceutical composition of Embodiment 15.

Embodiment 17 is a method of treating a tauopathy, in a subject in need thereof, comprising administering to the subject the pharmaceutical composition of Embodiment 15.

Embodiment 18 is the method of Embodiment 17, further comprising administering to the subject an additional agent for treating the tauopathy in the subject in need thereof.

Embodiment 19 is a method of treating a tauopathy in a subject in need thereof, comprising administering to the subject the pharmaceutical composition of Embodiment 15, wherein the tauopathy is selected from the group consisting of familial Alzheimer's disease, sporadic Alzheimer's disease, frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica (boxing disease).

Embodiment 20 is the method of Embodiment 19, further comprising administering to the subject an additional agent for treating the tauopathy in the subject in need thereof.

Embodiment 21 is a method of producing the monoclonal antibody or antigen-binding fragment of any of Embodiments 1 to 11, comprising culturing a cell comprising a nucleic acid encoding the antibody or antigen-binding fragment under conditions to produce the antibody or antigen-binding fragment, and recovering the antibody or antigen-binding fragment from the cell or cell culture.

Embodiment 22 is a method of producing a pharmaceutical composition comprising the monoclonal antibody or antigen-binding fragment of any of Embodiments 1 to 11, comprising combining the antibody or antigen-binding fragment with a pharmaceutically acceptable carrier to obtain the pharmaceutical composition.

Embodiment 23 is an isolated monoclonal antibody or antigen-binding fragment of any of Embodiments 1 to 11 for use in treating a tauopathy, in a subject in need thereof.

Embodiment 24 is an isolated monoclonal antibody or antigen-binding fragment of any of Embodiments 1 to 11 or the pharmaceutical composition of Embodiment 15 for use in treating a tauopathy, such as familial Alzheimer's disease, sporadic Alzheimer's disease, frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, or dementia pugulistica (boxing disease), in a subject in need thereof.

Embodiment 25 is a use of an isolated monoclonal antibody or antigen-binding fragment of any of Embodiments 1 to 11 for manufacturing a medicament in treating a tauopathy in a subject in need thereof.

Embodiment 26 is a use of an isolated monoclonal antibody or antigen-binding fragment of any of Embodiments 1 to 11 for manufacturing a medicament for treating a tauopathy, such as familial Alzheimer's disease, sporadic Alzheimer's disease, frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, or dementia pugulistica (boxing disease), in a subject in need thereof.

Embodiment 27 is a method of detecting the presence of phosphorylated tau in a biological sample from a subject, comprising contacting the biological sample with the antibody or antigen-binding fragment of any of Embodiments 1 to 11, and detecting binding of the antibody or antigen-binding fragment to PHF-tau in the sample from the subject.

Embodiment 28 is the method of Embodiment 27, wherein the biological sample is a blood, serum, plasma, interstitial fluid, or cerebral spinal fluid sample.

Embodiment 29 is a method of diagnosing a tauopathy in a subject by detecting the presence of phosphorylated tau in a biological sample from the subject, comprising contacting the biological sample with the antibody or antigen-binding fragment of any of Embodiments 1 to 11, and detecting binding of the antibody or antigen-binding fragment to PHF-tau in the sample from the subject.

EXAMPLES

The following examples of the invention are to further illustrate the nature of the invention. It should be understood that the following examples do not limit the invention and that the scope of the invention is to be determined by the appended claims.

Example 1—Antibody Characterization

PT3 and a set of antibodies derived from immunization of a Balb/c mouse with enriched PHF-tau (ePHF-tau) from AD brain was tested for target selectivity for phospho-tau versus non-phospho-tau in direct enzyme-linked immunosorbent assay (ELISA), Western blot, and immunohistochemistry (IHC). PT3 is a mouse-hybridoma-derived antibody having heavy chain variable region amino acid sequence of SEQ ID NO: 25 and light chain variable region amino acid sequence of SEQ ID NO: 30. The CDR sequences for the VH and VL domains of PT3 are shown in U.S. Pat. No. 9,371,376. PT3 was humanized using the Human Framework Adaptation (HFA) method (see Example 4) to generate humanized anti-phospho-tau antibodies of the invention (see Tables 1 and 2). Humanized B296 has the same CDR sequences as PT3. Humanized mAb B296 was affinity matured to generate additional antibodies of the invention (see Table 3).

ELISA

Recombinant PT3 as mouse IgG1 (mIgG1) was evaluated for binding to enriched PHF-tau and recombinant human wild-type tau in ELISA format. This recombinantly derived PT3 was compared to hybridoma-derived, purified PT3. The results demonstrated comparable binding titration curves between both purified hybridoma-derived and recombinantly derived PT3 antibody batches (FIG. 1). Strong binding was present on PHF-tau, and minimal binding was present on soluble tau at the higher concentrations.

Western Blot

Figure 2:
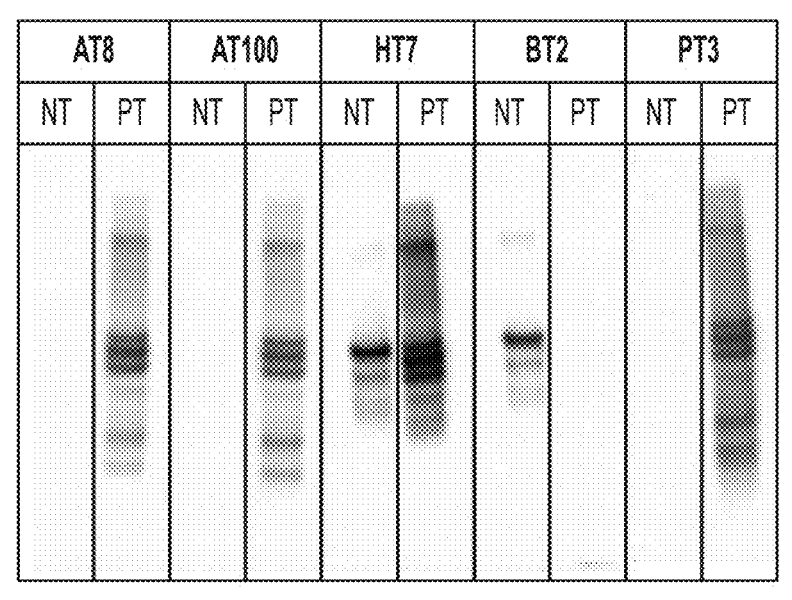

Western blot analysis was performed with PT3 against purified non-phosphorylated recombinant human tau and sarcosyl-insoluble PHF-tau prepared from AD brain. PT3 showed a selective reactivity with PHF-tau, similar to the phospho-selective reference antibodies AT8 pS202/pT205/pS208 (Mercken et al., *Acta Neuropathol.* 84(3):265-72, 1992; Malia et al., *Proteins.* 84:427-434, 2016) and AT100 pT212/pS214 (Mercken et al., 1992, Id.; Hoffmann et al., *Biochemistry.* 36(26):8114-24, 1997) (FIG. 2). The phospho-independent reference antibody HT7 (Mercken, Ph.D. Thesis: University of Antwerp, Wilrijk-Antwerp, 1991) reacted with both recombinant tau and PHF-tau. BT2, which is directed to an epitope that is phospho-sensitive, reacted only with recombinant tau not phosphorylated at S199/S202 (Mercken, 1991, Id.). In other western blot experiments, PT3 showed a weak reactivity with recombinant tau even when blotted at a higher concentration.

Immunohistochemistry on Human Brain

Immunohistochemical analysis was performed on formalin-fixed paraffin-embedded sections of AD and control brain to confirm reactivity with tauopathy in situ. PT3 showed a similar, but stronger, reactivity pattern as the reference tauopathy-specific diagnostic antibody positive control AT8 (FIGS. 3A-3E). No significant reaction with normal tau in control brain was detected under these experimental conditions (FIGS. 4A-4E).

Immunohistochemistry on Wild-Type and Tau Knock-Out Mice

Figures 6A, 6B:
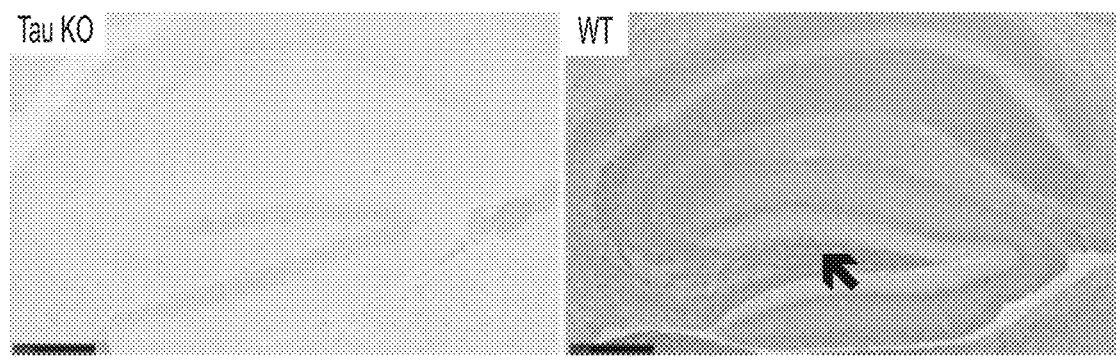
FIGS. 6A-6B show the non-phospho-tau specific staining pattern of tau-1 in in (A) tau knock out or (B) wild type mouse brain.

IHC analysis was performed with PT3 in wild-type and tau knock-out mouse brain. IHC analysis with PT3 in wild-type mouse brain indicates that reactivity with a selected pool of wild-type tau can be observed under conditions of optimal epitope conservation. The staining pattern of PT3 reveals a somatodentritic localization (FIG. 5B, arrow), reminiscent of the staining described in the literature for anti-phospho-tau antibodies in rat and human-biopsy-derived tissue (Matsuo et al., *Neuron.* 13(4):989-1002, 1994). The typical non-phospho axonal staining pattern for tau as observed with the tau-1 antibody (FIG. 6B, arrow) is not present, indicating that PT3 has limited reactivity with the physiologically important pool of microtubule-bound tau. The absence of reactivity in tau knock-out animals confirms the tau specificity of the PT3 staining pattern.

The presence of phosphorylation at the PT3 epitope (pT212/pT217, see Example 2) in wild-type mouse brain is supported by the detection of phosphorylation at the mouse homologue of T212 and T217 in mass spectrometric analysis by Morris et al. (*Nat Neurosci.* 18(8):1183-9, 2015). It suggests that the PT3 epitope will also be present at an early stage of tau phosphorylation and aggregate formation, which would be preferred for a therapeutic antibody epitope.

Binding Assessment by Surface Plasmon Resonance (SPR)

The interactions with PHF-tau and recombinant tau were assessed by SPR on ProteOn (Bio-Rad, Hercules, Calif.) and Biacore (Biacore, Uppsala, Sweden) instruments for PT1 and PT3 anti-PHF-tau antibodies. The total tau antibody HT7 was tested as a positive control, and AT8 was tested as a reference anti-PHF-tau antibody.

Tables 4 and 5 show representative results of the affinity assessment of the antibodies with PHF-tau and recombinant tau. PT3 monoclonal antibody showed very tight binding to PHF-tau (Table 4).

TABLE 4

ProteOn SPR affinities for hybridoma and recombinant mAbs and Fabs with PHF-tau

| mAb/Fab name | $k_{on}$ (1/Ms) | $k_{off}$ (1/s) | $K_D$ (pM) [a] |
|---|---|---|---|
| HT7 mAb | $(7.06 \pm 0.62) \times 10^5$ | $(9.26 \pm 2.77) \times 10^{-5}$ | $131 \pm 41$ |
| PT1 mAb (hyb) | $2.01 \times 10^5$ | $6.47 \times 10^{-5}$ | 322 |
| PT3 mAb (rec mG2a) | $(3.12 \pm 0.40) \times 10^6$ | $<5.0 \times 10^{-5}$ | ≤16 |
| PT3 Fab | $(1.83 \pm 0.08) \times 10^6$ | $(1.15 \pm 0.02) \times 10^{-4}$ | $63 \pm 3$ |
| AT8 mAb (hyb) | $(2.30 \pm 0.19) \times 10^6$ | $(2.11 \pm 0.07) \times 10^{-4}$ | $92 \pm 8$ |
| AT8 Fab | $(8.89 \pm 0.87) \times 10^5$ | $(2.30 \pm 0.14) \times 10^{-2}$ | $25,844 \pm 2,995$ |

For n ≥ 3 replicates, standard deviation is reported;
hyb, hybridoma-expressed mAb; rec, recombinant mAb;
[a] $K_D$ values in parentheses were obtained by excluding the 75 nM injected mAb concentration.

The apparent binding affinity ($K_D$) of recombinant PT3-mG2a was equal to or tighter than 16 pM with very slow off-rates. Only very weak binding to recombinant tau was observed for hybridoma-expressed PT3 in one of four replicates (Table 5).

TABLE 5

Biacore SPR affinities for hybridoma and recombinant mAbs and Fabs with recombinant tau

| mAb/Fab name | $k_{on}$ (1/Ms) | $k_{off}$ (1/s) | $K_D$ (pM) |
|---|---|---|---|
| HT7 mAb | $(3.86 \pm 2.00) \times 10^6$ | $(1.18 \pm 0.54) \times 10^2$ | $3,050 \pm 2,110$ |
| PT1 mAb (hyb) | | No significant binding [a] | |
| PT3 mAb (hyb) | | Low binding observed only in 1 of 4 replicates [a] | |
| PT3 mAb (rec mG2a) | | No Binding | |
| PT3 Fab | | No binding | |
| AT8 mAb (hyb) | | No binding [a] | | hyb, hybridoma-expressed mAb; rec, recombinant;
[a] Tested on ProteOn with recombinant tau from Sigma-Aldrich (St. Louis, MO) (0.12-75 nM at 5-fold dilutions) which was later determined to be aggregated. For all other tested samples, in-house-generated recombinant tau was used on Biacore.

Because of the multimeric/aggregated nature of PHF-tau with multiple copies of the epitope and the bivalent nature of IgGs, monoclonal antibody affinity was influenced by avidity in this study format. Fab affinity provides information on the intrinsic affinity of the antibody. PT3 Fab showed strong intrinsic binding affinity to PHF-tau ($K_D$=63 pM) and a slow off-rate (Table 4). Reactivity of the Fab with recombinant tau in Biacore SPR was below the detection limit under the conditions of the analysis (Table 5).

Characterization studies demonstrated that PT3 selectively binds PHF-tau and that it has a high affinity towards PHF-tau derived from AD brain.

Example 2—Epitope Mapping of PT3

The epitope of PT3 was determined by Surface Plasmon Resonance (ProteOn) with a panel of phosphopeptides depicted in Table 6.

Materials and Methods. PT3 Fab (B187) was produced as a chimeric version with a mouse variable and a human IgG1/κ constant region, with a 6×His tag at the C-terminus of the heavy chain (VH10, SEQ ID NO: 25 and VL7, SEQ ID NO: 30). The Fab was produced by transient expression in HEK 293 cells, purified by Ni-affinity chromatography, and dialyzed into 20 mM Tris pH 7.4, 50 mM NaCl (Sino Biologicals).

The binding affinity of PT3 Fab towards each of the fourteen tau phosphopeptides shown in Table 6 was assessed by surface plasmon resonance (SPR) using a Bio-Rad ProteOn XPR36. Peptides were synthesized by standard chemical methods (New England Peptide) with short-chain biotin and a PEG4 moiety at the N-terminus. Biotinylated peptide was captured on a neutravidin-coated NLC biosensor chip and PT3 Fab was flowed over the surface to measure kinetic parameters.

All experiments were performed at 25° C. using phosphate buffered saline, pH 7.4, 0.005% Tween 20 (PBST) as both running buffer and sample dilution buffer. Prior to running samples, the NLC chip was conditioned by running PBST over the chip surface for 1 h. Approximately 5-10 RU of peptide was captured on the chip surface by diluting peptide to 10 ng/mL in PBST and injecting over the flow channels at 30 μL/min for 100 s. Serial dilutions of PT3 Fab (1.1-90 nM) were analyzed and, with the exception of Peptide-8, each concentration was measured in duplicate. After capture of peptides, the antibody titration was injected at 60 μL/min for 3 minutes (association phase), followed by 300 s of buffer only (dissociation phase).

The data were double referenced by subtraction of the interspot response and the curves generated by the buffer-only injection. The chip surface was regenerated using a single injection of 0.85% phosphoric acid at 30 μL/min for 100 s contact time, followed by four injections of running buffer before the next antibody titration injection. The data processing and kinetic analysis were done using the instrument software. The data were analyzed using a simple Langmuir 1:1 binding model.

Results. The kinetic rate constants and equilibrium binding affinities for PT3 Fab are shown in Table 6.

TABLE 6

ProteOn SPR affinity data for PT3 Fab binding to peptides

| Peptide Name | Phosphorylated sites | Sequence*** | Avg KD (nM) | KD range or STDEV (nM) | Avg ka (1/Ms) |
|---|---|---|---|---|---|
| Peptide-1 | 212/214/217 | GTPGSRSR(pT)P(pS)LP(pT)PPTREPKK (SEQ ID NO: 47) | 0.26 | 0.14-0.38 | 1.27E+06 |
| Peptide-2 | 212/217 | GTPGSRSR(pT)PSLP(pT)PPTREPKK (SEQ ID NO: 48) | 0.27 | 0.09-0.45 | 7.64E+05 |
| Peptide-3* | 214/217 | GTPGSRSRTP(pS)LP(pT)PPTREPKK (SEQ ID NO: 49) | 5.57 | 1.64 | 1.04E+06 |
| Peptide-4 | 210/217 | GTPGSR(pS)RTPSLP(pT)PPTREPKK (SEQ ID NO: 50) | 6.60 | 6.48-6.71 | 9.68E+05 |
| Peptide-5 | 210/214/217 | GTPGSR(pS)RTP(pS)LP(pT)PPTREPKK (SEQ ID NO: 51) | 8.70 | 6.6-10.8 | 7.04E+05 |
| Peptide-6 | 217 | GTPGSRSRTPSLP(pT)PPTREPKK (SEQ ID NO: 52) | 11.4 | 10.9-11.9 | 5.41E+05 |
| Peptide-7 | 212/214 | GTPGSRSR(pT)P(pS)LPTPPTREPKK (SEQ ID NO: 53) | 13.5 | 11.3-15.7 | 4.22E+05 |
| Peptide-8** | 212 | GTPGSRSR(pT)PSLPTPPTREPKK (SEQ ID NO: 54) | 23 | n/a | 2.81E+05 |
| Peptide-9 | 214 | GTPGSRSRTP(pS)LPTPPTREPKK (SEQ ID NO: 55) | >500 | n/a | n/a |
| Peptide-10 | 210/214 | GTPGSR(pS)RTP(pS)LPTPPTREPKK (SEQ ID NO: 56) | >500 | n/a | n/a |
| Peptide-11# | 208/212/214 | SPGTPG(pS)RSR(pT)P(pS)LPTPPT (SEQ ID NO: 57) | no binding | n/a | n/a |
| Peptide-12 | 210 | GTPGSR(pS)RTPSLPTPPTREPKK (SEQ ID NO: 58) | no binding | n/a | n/a |
| Peptide-13 | 214/220 | GTPGSRSRTP(pS)LPTPP(pT)REPKK (SEQ ID NO: 59) | no binding | n/a | n/a |
| Peptide-C | none | GTPGSRSRTPSLPTPPTREPKK (SEQ ID NO: 60) | no binding | n/a | n/a |

| Peptide Name | ka range or STDEV (1/Ms) | Avg kd (1/s) | kd range or STDEV (1/s) | # of replicates |
|---|---|---|---|---|
| Peptide-1 | (0.87-1.67)E+06 | 2.80E-04 | (2.36-3.24)E-04 | 2 |
| Peptide-2 | (5.46-9.82)E+05 | 1.68E-04 | (0.91-2.45)E-04 | 2 |
| Peptide-3* | 2.83E+06 | 5.47E-03 | 1.77E-04 | 3 |
| Peptide-4 | (9.22-9.68)E+05 | 6.27E-03 | (6.19-6.27)E-03 | 2 |
| Peptide-5 | (5.45-8.63)E+05 | 5.84E-03 | (5.69-5.98)E-03 | 2 |
| Peptide-6 | (5.24-5.58)E+05 | 6.16E-03 | (6.06-6.25)E-03 | 2 |
| Peptide-7 | (3.57-4.87)E+05 | 5.55E-03 | (5.49-5.60)E-03 | 2 |
| Peptide-8** | n/a | 6.46E-03 | n/a | 1 |
| Peptide-9 | n/a | n/a | n/a | 1 |
| Peptide-10 | n/a | n/a | n/a | 2 |
| Peptide-11# | n/a | n/a | n/a | 1 |
| Peptide-12 | n/a | n/a | n/a | 2 |

TABLE 6-continued

ProteOn SPR affinity data for PT3 Fab binding to peptides

| | | | | |
|---|---|---|---|---|
| Peptide-13 | n/a | n/a | n/a | 2 |
| Peptide-C | n/a | n/a | n/a | 4 |

For n = 2, range is reported;
*For Peptide-3, n = 3, standard deviation is reported;
**For Peptide-8, n = 1, no average or range is reported;
***Unless noted, all peptides include tau residues 204-225 (isoform 2N4R) and contain a short chain biotin moiety (SCBiot) and dPEG4 at the N-terminus and an amide at the C-terminus;
Peptide-11 includes tau residues 202-220 (isoform 2N4R).

PT3 Fab showed nanomolar binding to peptides phosphorylated at T212 or T217, and PT3 Fab's binding was enhanced when both T212 and T217 were phosphorylated. PT3 Fab bound best to peptides containing pT212 and/or pT217. PT3 Fab bound with similar affinity to tau peptide phosphorylated at T212/T217 (Peptide-2) and to tau peptide phosphorylated at T212/S214/T217 (Peptide-1), demonstrating that the additional phosphorylation at S214 does not enhance the binding of PT3 Fab. PT3 Fab had only very weak binding to pS214-tau peptide (Peptide-9). Little to no effect of binding was observed when S210 was phosphorylated alone or in combination with other phosphorylated residues. Phosphorylation at T220 appeared to contribute to loss of binding activity for PT3 Fab (Peptide-9 vs. Peptide-13). No binding activity was detected for PT3 Fab against non-phosphorylated tau peptide (Peptide-C). PT3 binds to a phosphoepitope within the proline rich domain of tau.

The binding studies suggest that the PT3 epitope includes pT212 and pT217, and that a maximal binding epitope of PT3 includes doubly phosphorylated pT212/pT217-tau. The epitope of PT3 is distinct from other reported epitopes for phospho-dependent anti-tau antibodies, such as AT8 (pS202/pT205/pS208; Malia et al., 2016 Id.), AT180 (pT231; Goedert et al., Biochemical J. 301(Pt3):871-877), AT270 (pT181; Goedert et al., Id.), PHF1 (pS396/pS404; Otvos et al., J Neurosci Res. 39(6):669-73, 1994), 12E8 (pS262; Seubert et al., J Biol Chem. 270(32):18917-22, 1995), anti-tau pS422 antibody (Collin et al., Brain. 137(Pt 10):2834-46, 2014), and anti-tau pS409 antibody (Lee et al., Cell Rep. 16(6): 1690-700, 2016).

Example 3—Crystal Structure of PT3 Fab+pT212/pT217-Tau Peptide Complex

The co-structures of PT3 Fab (B187) with two tau phosphopeptides were determined by X-ray crystallography which led to the identification of the tau epitope and PT3 paratope.

Sample Preparation and Crystallization. Peptides for crystallization were synthesized by New England Peptides and had the following sequences: Ac-GSRSR(pT)P(pS)LP(pT)PPT-OH (SEQ ID NO: 61) corresponding to residues 207-220 of tau-441 (2N4R isoform) phosphorylated at residues T212, S214, and T217 (pT212/pS214/pT217-tau peptide), and Ac-SR(pT)PSLP(pT)PPTRE-OH (SEQ ID NO: 62), corresponding to residues 210-222 phosphorylated at T212 and T217 (pT212/pT217-tau peptide). Lyophilized peptides were dissolved in 100 mM Tris pH 8.5 to approximately 55 mg/mL.

PT3 Fab was concentrated to 19.64 or 17.76 mg/mL and mixed with a 10.7- or 9.3-fold molar excess of pT212/pS214/pT217-tau peptide or pT212/pT217-tau peptide to bring the final complex concentration to 16.9 and 16.7 mg/mL in 20 mM Tris pH 7.5, 100 mM or 50 mM NaCl, respectively. Crystallization was performed with in-house screens and PEGs (Qiagen) using the Mosquito crystallization robot, mixing 150 nL complex and 150 nL reservoir solution. Crystals for diffraction were obtained in the following conditions: PT3 Fab+pT212/pS214/pT217-tau peptide complex in 0.1 M Acetate pH 4.5, 18% PEG 3350, 0.2 M MgCl$_2$, and PT3 Fab+pT212/pT217-tau peptide complex in 20% PEG 3350, 0.2 M ammonium phosphate (monobasic).

Data Collection and Structure Determination. A crystal of PT3 Fab+pT212/pS214/pT217-tau peptide complex was harvested from 0.1 M Acetate pH 4.5, 18% PEG 3350, 0.2 M MgCl$_2$ (mother liquor) and mixed with cryoprotectant solution composed of the mother liquor supplemented with 20% glycerol. The crystal was flash-cooled in liquid nitrogen, and data were collected on a Rigaku MicroMax™-007HF microfocus X-ray generator equipped with Osmic™ VariMax™ confocal optics, Saturn 944 CCD detector, and an X-Stream™ 2000 cryocooling system (Rigaku).

The data were processed with XDS (Kabsch, Acta Crystallogr D Biol Crystallogr. 66(Pt 2):125-32, 2010). Molecular replacement was performed with phaser (McCoy et al., J Appl Crystallogr. 40(Pt 4):658-674, 2007) in the PHENIX suite of programs (Adams et al., Acta Crystallogr D Biol Crystallogr. 66(Pt 2):213-21, 2010) using Fab H3-23:L1-39 (PDB ID: 5119) Fab as the search model. Phenix.xtriage identified pseudomerohedral twinning in the crystal with 7% twinned fraction. Refinement was performed using twin refinement for the majority of model building. Model building was with Coot (Emsley and Cowtan, Acta Crystallogr D Biol Crystallogr. 60(Pt 12 Pt 1):2126-32, 2004) and refinement was with phenix.refine (Adams et al., 2010, Id.). The final stage of refinement was without twin refinement, since it was later determined that twin refinement did not improve the maps. Data and refinement statistics are shown in Table 7.

TABLE 7

X-ray data and refinement statistics

| | PT3 Fab+<br>pT212/pS214/<br>pT217-<br>tau peptide complex | PT3 Fab+<br>pT212/pT217-tau<br>peptide complex |
|---|---|---|
| Beamline/detector | Rigaku MicroMax-<br>007HF/Saturn 944 | APS IMCA-CAT/<br>Pilatus 6M |
| Data | | |
| Wavelength (Å) | 1.5418 | 1.000 |
| Resolution range (Å) | 30-2.5 (2.6-2.5) | 8.94-2.0 (2.05-2.00) |
| Space group | C2 | C2 |
| Unit-cell axes (Å) | 125.21, 83.50, 167.41 | 126.24, 83.66, 166.87 |

TABLE 7-continued

X-ray data and refinement statistics

|  | PT3 Fab+<br>pT212/pS214/<br>pT217-<br>tau peptide complex | PT3 Fab+<br>pT212/pT217-tau<br>peptide complex |
|---|---|---|
| Unit-cell angles (°) | 90.00, 91.71, 90.00 | 90.00, 92.50, 90.00 |
| Molecules/asym. unit | 3 | 3 |
| $V_m$ (Å³/Da)/solv.(%) | 2.92/58 | 3.08/60 |
| Completeness (%) | 97.0 (89.3) | 99.2 (99.6) |
| $R_{merge}$ | 0.108 (0.318) | 0.053 (0.555) |
| Mean I/σ(I) | 4.9 (1.7) | 13.09 (2.49) |
| No. of measured reflections | 177373 (11739) | 384718 (27833) |
| No. of unique reflections | 57942 (3878) | 116430 (8607) |
| B-factor (Wilson) (Å²) | 29.1 | 36.49 |
| Refinement statistics |  |  |
| No. of atoms | 11165 | 10968 |
| No. of water molecules | 961 | 779 |
| $R_{work}/R_{free}$ (%) | 19.4/23.1 | 18.6/21.3 |
| R.m.s.d. from ideal geometry |  |  |
| Bond lengths (Å) | 0.005 | 0.008 |
| Bond angles (°) | 1.005 | 1.215 |
| Average B factors (Å²) | 26.87 | 41.2 |
| Ramachandran plot |  |  |
| Residues in favored regions (%) | 97.23 | 98.31 |
| Residues in allowed regions (%) | 2.47 | 1.62 |
| Outliers (%) | 0.31 | 0.08 |

Values for the highest resolution shell are indicated in parentheses.

A single crystal of PT3 Fab+pT212/pT217-tau peptide complex was extracted from the crystallization drop, immersed for a few seconds in the reservoir solution (20% PEG 33500, 0.2 M ammonium phosphate (monobasic)) supplemented with 20% glycerol and flash-cooled in liquid nitrogen. Data were collected at the Advanced Photon Source (Argonne, Ill.) IMCA-CAT beamline 17-ID-B at 100 K. Diffraction intensities were collected on a Pilatus 6M detector over a 180° rotation with an exposure time of 0.5 s per half-degree image. The data were processed with XDS (Kabsch, 2010, Id.) to the maximum resolution of 2.0 Å. The structure was determined by molecular replacement with the program Phaser (McCoy et al., 2007, Id.) using the PT3 Fab+pT212/pS214/pT217-tau peptide structure as the search model. Structure refinement was performed with phenix.refine using NCS (Adams et al., 2010, Id.). Model adjustments were carried out using the program Coot (Emsley and Cowtan, 2004, Id.). X-ray data collection and refinement statistics are shown in Table 7. Intermolecular contact distances were calculated with CONTACT (Collaborative Computational Project, Number 4, *Acta Crystallogr D Biol Crystallogr.* 50(Pt 5):760-3, 1994) using a distance cutoff of 4.0 Å and inspected visually with Pymol.

Structural Analysis. The structure of PT3 Fab with pT212/pS214/pT217-tau peptide was determined to 2.5 Å resolution. There are three copies of the complex per asymmetric unit as described below for the PT3 Fab+pT212/pT217-tau peptide structure. The structure shows that PT3 does not interact with the phosphate of pS214 when T212 and T217 are also phosphorylated (data not shown), which is supported by phosphopeptide mapping by ProteOn (Example 2).

Figure 7:
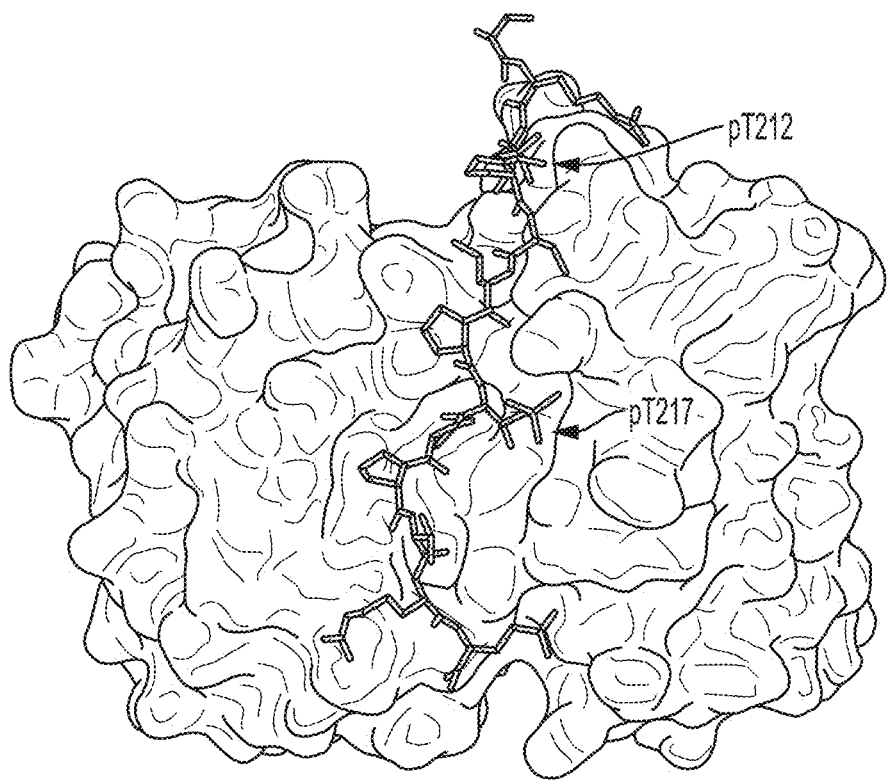
FIG. 7 shows the crystal structure of the PT3 Fab+pT212/pT217-tau peptide complex, with PT3 Fab shown in a space filling representation (light gray), and tau peptide shown in stick representation (black).
Figure 8:
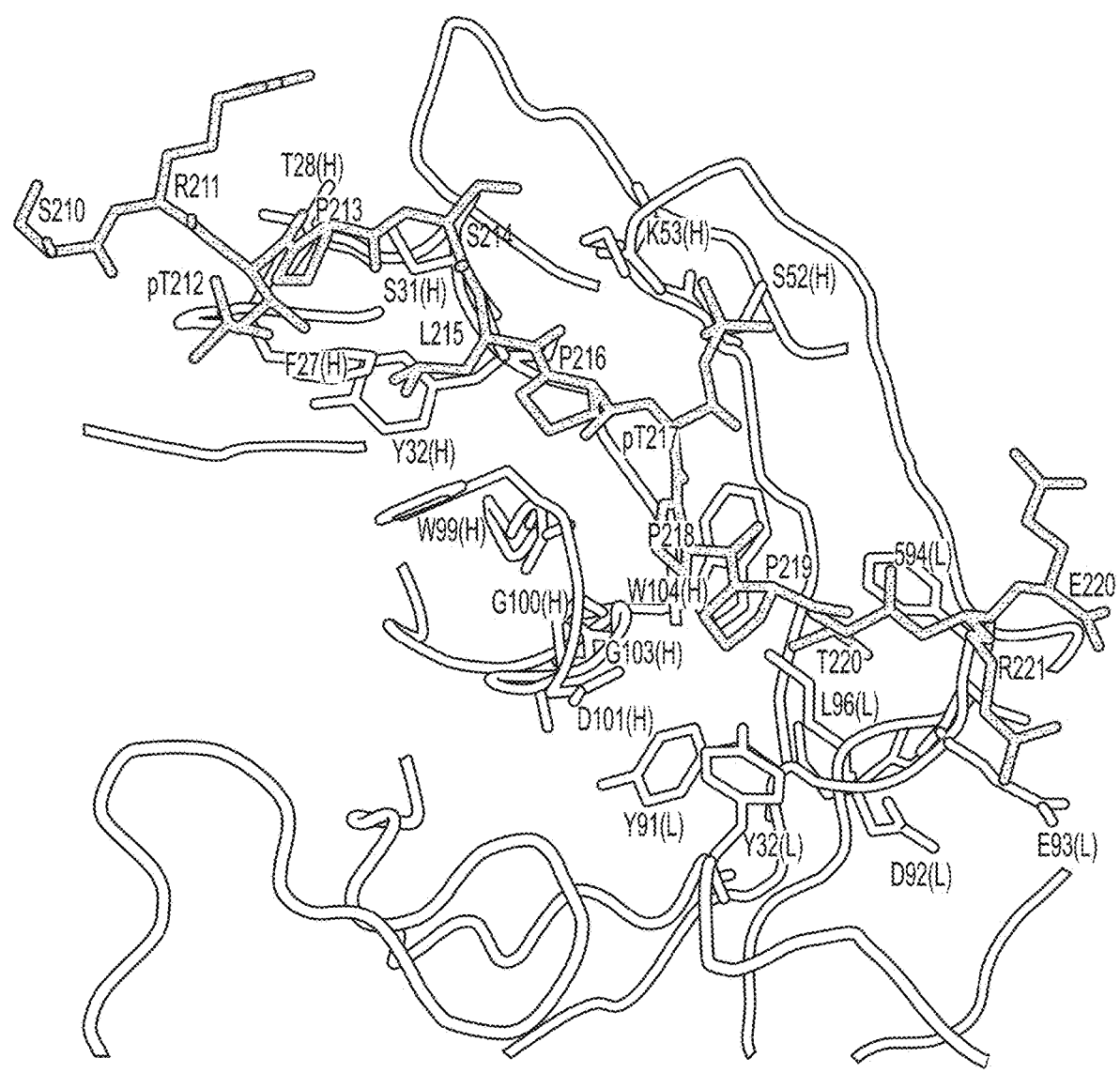
FIG. 8 shows the crystal structure of the PT3 Fab+pT212/pT217-tau peptide complex, with PT3 shown in ribbons (light gray) with its paratope residues shown in stick representation, and tau peptide shown in stick representation (black).

The structure of PT3 Fab with pT212/pT217-tau peptide was determined by X-ray crystallography at 2.0 Å resolution (FIG. 7). There are three copies of the complex in the asymmetric unit (copy 1: chains A, C, E; copy 2: chains B, D, F; copy 3: chains H, L, P), consisting of heavy chains A, C, and H, light chains B, D, and L, and peptide chains E, F, and P. The three copies were highly similar—variable regions were within 0.3 Å rmsd. FIG. 7 and FIG. 8 show copy 3 (chains H, L, P). As seen in FIG. 7, the Fab heavy and light chains form a shallow binding pocket, and the peptide lays across the Fab. The tau phosphopeptide is in an extended conformation with characteristics consistent with polyproline-II helix secondary structure.

Figure 9:
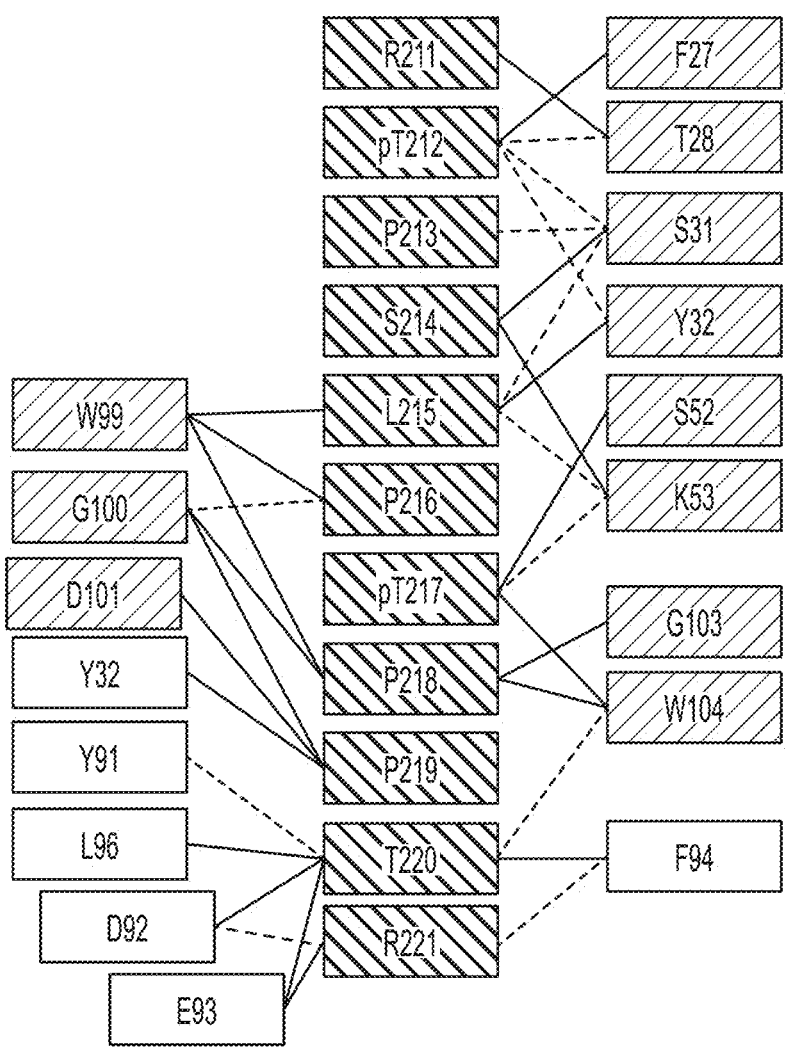
FIG. 9 shows an interaction diagram for the PT3 Fab+pT212/pT217-tau peptide structure, with the peptide residues shown in the black boxes with white lettering, the VH residues shown in dark gray, the VL residues shown in light gray, and where the dotted lines represent hydrogen bonds and the solid lines represent van der Waals contacts.

PT3 Fab paratope and pT212/pT217-tau peptide epitope residues that comprise the interaction interface are shown in FIG. 8 and FIG. 9, and in Table 8. The interface between PT3 and its epitope peptide is made up of van der Waals and electrostatic interactions, which extend from peptide residues 211 to 221. The structure of PT3 Fab in complex with the pT212/pT217-tau peptide shows that the epitope includes the phosphates of pT212 and pT217. The heavy chain Y32 hydroxyl group forms an important hydrogen bond with a phosphate oxygen of pT212. The sidechain hydroxyl group of T28 (VH) also forms a hydrogen bond with a phosphate oxygen of pT212. Heavy chain K53 forms a key salt bridge interaction with pT217. Heavy chain W99 forms hydrophobic interactions with side chain residues of L215 and P216 of the peptide. Heavy chain residue W104 has extensive interactions with the peptide and also forms part of the VH/VL interface. Light chain Y32 forms a hydrophobic interaction with P219. Electrostatic interactions with the phosphates of pT212 and pT217 are critical for the selectivity of PT3 for phospho-tau, and hydrophobic interactions additionally contribute to the high affinity of PT3 for pT212/pT217-tau (Example 5) and PHF-tau (Examples 1 and 6).

TABLE 8

Epitope and paratope of PT3 Fab + pT212/pT217-tau peptide.
Residues from PT3 Fab VH or VL that interact with pT212/
pT217-tau peptide residues are indicated.
Hydrogen bonding interactions are indicated with bold type.

| $V_H$ | Peptide | $V_L$ |
|---|---|---|
| T28 | R211 |  |
| F27, T28, S31, Y32 | pT212 |  |
| S31 | P213 |  |
| S31, K53 | S214 |  |
| S31, Y32, K53, W99 | L215 |  |
| W99, G100 | P216 |  |
| S52, K53, W104 | pT217 |  |
| W99, G100, G103, W104 | P218 |  |
| G100, D101 | P219 | Y32 |
| W104 | T220 | Y91, D92, E93, F94, L96 |
|  | R221 | D92, E93, F94 |

Example 4—Human Framework Adaptation for PT3

The anti-tau mouse antibody PT3 was humanized using the Human Framework Adaptation (HFA) method (Fransson et al., *J Mol Biol.* 398(2):214-31, 2010). For human framework adaptation CDRs were defined according to Martin (Martin and Thornton, *J Mol Biol.* 263(5):800-15, 1996). To find the best combination of humanized HC and LC, several human heavy and light V-region sequences were selected for testing. Four human framework adapted PT3 heavy chain variable regions and four human framework adapted PT3 light chain variable regions were designed and generated as full human heavy chain IgG1 and human light chain kappa molecules (FIG. 10). Based on sequence similarity to mouse PT3 VH and VL in only the framework regions (FR), human germline V genes (4 for VH: IGHV3-23*01, IGHV3-33*01, IGHV3-11*01 and IGHV13*01; 4 for VL: IGVK1-16*01, IGVK1-16*01+, IGKV1-39*01 and IGKV224*01) were selected for producing the human framework adapted VH and VL variants. VL78 (IGVK116*01+) is single point mutant of VL77 (IGVK116*01) and contains a D56S mutation to eliminate a potential isomerization risk. The names of the 16 HFA variant monoclonal antibodies resulting from combining the four HFA HC and four HFA LC molecules are shown in Table 9.

TABLE 9

HFA-PT3 variants. B234 contains the mouse parent variable regions and was included as a positive control. The corresponding human germline gene is indicated in parentheses. VL78 (IGVK1-16*01+) contains a single point mutation of VL77 (IGVK1-16*01).

|  | VH10 (PT3) (SEQ ID NO: 35) | VH91 (IGHV3-23*01) (SEQ ID NO: 36) | VH92 (IGHV3-33*01) (SEQ ID NO: 37) | VH93 (IGHV3-11*01) (SEQ ID NO: 38) | VH94 (IGHV1-3*01) (SEQ ID NO: 39) |
|---|---|---|---|---|---|
| VL7 (PT3) (SEQ ID NO: 40) | B234 | | | | |
| VL77 (IGVK1-16*01) (SEQ ID NO: 41) | | B235 | B296 | B282 | B268 |
| VL78 (IGVK1-16*01+) (SEQ ID NO: 42) | | B250 | B236 | B297 | B283 |
| VL79 (IGKV1-39*01) (SEQ ID NO: 43) | | B265 | B251 | B237 | B298 |
| VL80 (IGKV2-24*01) (SEQ ID NO: 44) | | B280 | B266 | B252 | B238 |

The cloning and DNA synthesis for the panel of 16 HFA-PT3 (hIgG/κ) variants were performed by standard methods. DNA was transfected into HEK (Expi293) cells by standard protocols, and cell supernatants were collected after 5 days in culture. Clarified supernatant was purified using a Protein BioSolutions ProteinMaker (Gaithersburg, Md.) for high-throughput parallel purification by capturing IgG on MabSelectSure Protein A resin pre-equilibrated in 1xdPBS, pH 7.2. After column washing with 1xdPBS, pH 7.2, monoclonal antibody was eluted using 0.1 M sodium acetate, pH 3.5. Elution fractions were neutralized by addition of 2.5 M Tris-HCl, pH 7.2 to 20% by volume, and the final protein formulation was 0.08 M Na acetate, 0.5 M Tris-HCl, pH 7.1.

Initial assessment of the HFA panel was based on purification yield, size-exclusion high-performance liquid chromatography (SE-HPLC) profile, binding to PHF-tau in ELISA binding assays, and biophysical characterization.

The Fab of B296 (B324) and the Fab of B252 (B326) were also generated by pairing the HC and LC variable regions of the corresponding monoclonal antibodies with a human IgG1/κ constant region and a 6xHis tag at the C-terminus of the heavy chain. B324 and B326 were expressed in HEK (Expi293) cells and purified by a similar method as described (Zhao et al., Protein Expr Purif. 67(2): 182-9, 2009).

Example 5—Characterization of HFA-PT3 Antibodies by SPR on Phosphopeptides

A subset of HFA-PT3 monoclonal antibody variants, selected based on biophysical characterization and ELISA binding to PHF, were analyzed by Surface Plasmon Resonance (SPR) with a ProteOn XPR36 for binding to the following phosphopeptides: pT212/pT217-tau peptide (Peptide-2, SEQ ID NO: 48) and pT212-tau peptide (Peptide-8, SEQ ID NO: 54). All experiments were performed at 25° C. using PBST, pH 7.4, (Bio-Rad Cat #176-2720) as both running buffer and sample dilution buffer.

Monoclonal antibody/Peptide binding. After pre-conditioning with PBST, a biosensor surface was prepared by coating a Biorad GLC chip with anti-human Fc (Jackson 109-005-098) to a density of approximately 6500 RU. Anti-human IgG was amine-coupled to the chip surface using EDC/NHS, then washed with ethanolamine. Antibodies were diluted to 2 µg/mL in PBST and injected on the surface for 5 min at 30 µL/min to achieve a maximum density of 900-1000 RU. Peptides were injected as analytes at 60 µL/min for 3 min, followed by 5 min dissociation. Peptide-2 was diluted in PBST to generate a three-fold concentration series (0-30 nM) and measured in duplicate. Single measurements of monoclonal antibody binding to Peptide-8 were recorded over the concentration range 0-100 nM.

Fab/peptide binding. Biotinylated peptide was captured on a neutravidin-coated NLC biosensor chip pre-conditioned with PBST, and Fab was flowed over the surface to measure kinetic parameters. Approximately 5-10 RU of peptide was captured on the chip surface by diluting peptide to 10 ng/mL in PBST and injecting over the flow channels at 30 µL/min for 100 s. Serial dilutions of PT3 Fab (1.1 nM to 90 nM) were injected at 60 µL/min for 3 minutes (association phase), followed by 300 s of buffer only (dissociation phase).

Data were double referenced by subtraction of the interspot response, and the curves generated by the buffer only injection. The chip surface was regenerated with 0.85% phosphoric acid, followed by PBST injection before the next antibody titration injection. Data processing and analysis were performed using instrument software. The data were fit using a simple Langmuir 1:1 binding model.

The kinetic rate constants and equilibrium binding affinities for HFA-PT3 IgGs towards Peptide-8 are shown in Table 10. B234 contains mouse PT3 variable regions and human IgG1/κ constant region. Among the humanized variants, B296 showed the strongest binding to Peptide-8 (pT212-tau).

TABLE 10

ProteOn SPR affinity data for HFA-PT3 mAb panel binding to Peptide-8

| Sample | Protein Description | Avg $k_a$, (1/Ms) | Avg $k_d$, (1/s) | Avg $K_D$, nM |
|---|---|---|---|---|
| B234 | mouse PT3, hIgG1 | 2.31E+06 | 8.02E−03 | 3.48 |
| B235 | VH91/VL77 | No binding | | |
| B252 | VH93/VL80 | 7.42E+05 | 2.42E−02 | 32.6 |
| B280 | VH91/VL80 | 2.18E+05 | 7.57E−03 | 34.7 (poor data fit) |
| B282 | VH93/VL77 | 4.42E+05 | 3.82E−02 | 86.5 |
| B296 | VH92/VL77 | 8.56E+05 | 2.30E−02 | 26.8 | n = 2 for all antibodies

The kinetic rate constants and equilibrium binding affinities for HFA-PT3 IgGs towards Peptide-2 are shown in Table 11. B252 and B296 showed the strongest binding to Peptide-2 (pT212/pT217-tau), with average $K_D$ values of 172 and 190 pM, respectively.

TABLE 11

ProteOn SPR affinity data for HFA-PT3 mAb panel binding to Peptide-2

| Sample | Protein Description | Avg $k_a$, (1/Ms) | $k_a$ Range | Avg $k_d$ (1/s) | kd Range | Avg $K_D$ pM | $K_D$ Range (pM) |
|---|---|---|---|---|---|---|---|
| B234 | mouse PT3, hIgG1 | 9.35E+06 | (8.7-10)E+06 | 3.25E−04 | (2.42-4.08)E−04 | 29.2 | (27.8-30.6) |
| B235 | VH91/VL77 | 3.21E+06 | (2.84-3.58)E+06 | 5.69E−03 | (5.28-6.10)E−03 | 1790 | (1710-1860) |
| B252 | VH93/VL80 | 5.75E+06 | (3.95-7.54)E+06 | 9.01E−04 | (8.56-9.46)E−04 | 172 | (126-217) |
| B280 | VH91/VL80 | 4.71E+06 | (2.21-7.20)E+06 | 2.74E−03 | (2.46-3.01)E−03 | 769 | (418-1120) |
| B282 | VH93/VL77 | 3.12E+06 | (2.34-3.89)E+06 | 1.32E−03 | (1.24-1.40)E−03 | 445 | (360-529) |
| B296 | VH92/VL77 | 5.00E+06 | (3.10-6.90)E+06 | 8.26E−04 | (7.88-8.63)E−04 | 190 | (125-255) | n = 2 for all antibodies

Affinity of the Fabs of B296 and B252 were measured on the pT212/pT217-tau peptide (Peptide-2) by ProteOn and compared to the mouse parent Fab B187 (Table 12). There was a 2.7-5.1-fold increase in off-rate and 3.5-5.6-fold increase in $K_D$ values for the HFA Fabs compared to parental mouse Fab. The Fab of B296 (B324) showed a stronger affinity for pT212/pT217-tau peptide than the Fab of B252 (1326), as well as slower off-rate.

TABLE 12

ProteOn SPR affinity data for HFA-PT3 Fabs binding to Peptide-2

| Sample | Description | Avg $k_a$ (1/Ms) | $k_a$ Range (1/Ms) | Avg $k_d$ (1/s) | $k_d$ Range (1/s) | Avg $K_D$ (pM) | $K_D$ Range (pM) |
|---|---|---|---|---|---|---|---|
| B187 | mouse parental Fab of PT3 | 7.76E+05 | (4.91-10.6)E+05 | 6.39 E−05 | (4.93-7.84)E−05 | 87.4 | (73.8-101) |
| B324 | Fab of B296 | 6.10E+05 | (4.27-7.93)E+05 | 1.74 E−04 | (1.61-1.86)E−04 | 305 | (234-376) |
| B326 | Fab of B252 | 7.10E+05 | (5.07-9.12)E+05 | 3.29 E−04 | (3.04-3.53)E−04 | 493 | (387-599) | n = 2 for all Fabs

Example 6—Characterization of HFA-PT3 Antibodies by SPR on PHF-Tau and Recombinant Tau A subset of HFA-PT3 monoclonal antibodies was tested for binding to PHF-tau isolated from Alzheimer's disease brain. All interactions were studied at 25° C. using PBS pH 7.4, supplemented with 3 mM EDTA, and 0.005% Tween 20 as running or system buffer. HT7 (Pierce, catalog #MN1000), a mouse anti-tau antibody, was used as a positive control.

The interaction of anti-tau monoclonal antibodies with PHF-tau was analyzed by ProteOn using a biosensor surface prepared by capture-coupling PHF-tau using HT7 as the capture reagent. PHF-tau was prepared by 2-times centrifugation at 5000×g at 5° C. for 10 min; the supernatant from the second centrifugation was then diluted 1/40 in running buffer. To prepare the chip, HT7 was covalently immobilized to the surface of a GLC (ProteOn) sensor chip using the manufacturer's instructions for amine-coupling chemistry (~5000 response units (RU)). The coupling buffer was 10 mM sodium acetate, pH 4.5. After HT7 immobilization, PHF-tau was injected and captured (~300 RU) by HT7. After capture, PHF-tau was covalently immobilized to the sensor chip by activation of the chip using the manufacturer's instructions for amine-coupling chemistry. Remaining reactive sites were blocked by the injection of ethanolamine. After preparation and stabilization of the PHF-tau-modified surface and reference surface (containing no antigen), the anti-tau antibodies were diluted in the running buffer and injected in solution (0.12-75 nM in 5-fold dilutions). The association was monitored for 3 minutes (120 µL injected at 40 µL/min). The dissociation was monitored for 15 minutes. Regeneration of the sensor surface was performed using 10 mM Gly pH 2.0. The data for monoclonal antibodies were fit using a bivalent binding model where the apparent affinity ($K_D$) was reported as the ratio of $k_{off}/k_{on}$. A Langmuir 1:1 binding model was used for kinetics analysis of Fabs.

Most HFA monoclonal antibodies retained similar tight binding as the mouse parental PT3 monoclonal antibody, ranging from 27-165 pM (Table 13). B252 and B296, the top two HFA monoclonal antibodies, had affinities of 32 and 27 pM, respectively. B235 showed the weakest monoclonal antibody affinity (165 pM) from this panel. B324 (Fab of B296) and B326 (Fab of B252) were assessed for PHF-tau binding and showed a 2.5- and 3.3-fold weaker $K_D$, respectively, than the mouse PT3 parent Fab B187. B324 showed 1.3-fold stronger affinity ($K_D$) and a 1.7-fold slower off-rate than B326. The Fab affinities were weaker than their corresponding monoclonal antibody, suggesting avidity for the monoclonal antibody towards PHF-tau. B352, an IgG4 variant of B296 with the same variable regions, was also tested for binding to PHF-tau and the affinity (43 pM) was within 2-fold of that of B296 (Table 11).

TABLE 13

ProteOn SPR affinities for PT3 HFA mAbs and Fabs with PHF-tau

| Samples | Description | $k_{on}$ (1/Ms) | $k_{off}$ (1/s) | $K_D$ (pM) |
|---|---|---|---|---|
| HT7 | mouse (+ctrl) | (5.69 ± 0.99) E+05 | (1.10 ± 0.18) E−04 | 193 ± 46 |
| B17 (mAb) | mouse PT3, muG2a | (2.48 ± 0.20) E+06 | (2.68 ± 0.43) E−05 | 11 ± 1.9 |
| B234 (mAb) | mouse PT3, hIgG1 | (2.23 ± 0.13) E+06 | (2.71 ± 0.17) E−05 | 12 ± 1.0 |
| B235 (mAb) | VH91/VL77 | (4.90 ± 0.34) E+05 | (8.06 ± 0.24) E−05 | 165 ± 12 |
| B252 (mAb) | VH93/VL80 | (1.32 ± 0.09) E+06 | (4.28 ± 0.19) E−05 | 32 ± 2.6 |
| B280 (mAb) | VH91/VL80 | (1.02 ± 0.03) E+06 | (5.63 ± 0.28) E−05 | 55 ± 3.3 |
| B282 (mAb) | VH93/VL77 | (6.65 ± 0.09) E+05 | (4.08 ± 0.25) E−05 | 61 ± 3.9 |
| B296 (mAb) | VH92/VL77 | (1.07 ± 0.02) E+06 | (2.93 ± 0.19) E−05 | 27 ± 1.8 |
| B297 (mAb) | VH93/VL78 | (1.44 ± 0.07) E+06 | (6.03 ± 0.32) E−05 | 42 ± 3.0 |
| B187 (Fab) | PT3 Fab | (1.67 ± 0.05) E+06 | (1.13 ± 0.04) E−05 | 68 ± 3 |
| B326 (Fab) | B252 Fab | (1.02 ± 0.05) E+06 | (2.30 ± 0.04) E−04 | 224 ± 12 |
| B324 (Fab) | B296 Fab | (8.16 ± 0.45) E+05 | (1.36 ± 0.06) E−04 | 167 ± 12 |
| B352 (IgG4 mAb) | B296 as hIgG4 | (2.55 ± 0.56) E+05 | (1.11 ± 0.54) E−05 | 43 ± 23 | mAbs: n = 2 with 3 replicates within each experiment
Fabs: n = 2 with 2 replicates within each experiment
B352: n = 2 with 4 replicates in each experiment The interaction of anti-tau monoclonal antibodies and Fabs with recombinantly expressed control tau (human tau isoform 2N4R 441 aa, N-terminal 6×His-tag, SEQ ID NO: 63) was studied with a Biacore T200. A biosensor surface was prepared by coupling an anti-human IgG Fc specific antibody (Ab) or anti-Fd to the surface of a CM5 sensor chip using the manufacturer's instructions for amine-coupling chemistry (~6500 response units (RU). The coupling buffer was 10 mM sodium acetate, pH 4.5. The anti-tau antibodies were diluted in the running buffer and injected to obtain a capture of at least 5 RU. Capture of anti-tau monoclonal antibodies or Fabs was followed by injection of recombinantly expressed control tau in solution (0.12 to 75 nM in 5-fold dilutions). The association was monitored for 3 minutes (150 µL injected at 50 µL/min). The dissociation was monitored until at least 5% decrease in signal is observed for reasonable off-rate determination. Regeneration of the sensor surface was obtained with 0.85% phosphoric acid followed by 50 mM NaOH. The data for both monoclonal antibodies and Fabs were fit using a 1:1 Langmuir binding model if binding was observed.

Neither B324 nor B326 showed significant binding to control tau. B296 also showed no binding to control tau.

Example 7—Crystal Structure of B324+pT212/pT217-Tau Peptide Complex

The co-structure of B324 with pT212/pT217-tau peptide (SEQ ID NO: 62) was determined by X-ray crystallography, which led to the identification of the tau epitope and B324 (and B296) paratope.

Sample Preparation and Crystallization. B324, which is the Fab of B296 with VH92 and VL77, was produced by transient expression in HEK 293 cells, and purified by Ni-affinity chromatography, SEC, and ion exchange in a final buffer of 20 mM MES pH 6.0, 0.2 M NaCl. pT212/pT217-tau peptide (SEQ ID NO: 62), described in Example 3, was used for co-crystallization. For preparation of the B324 Fab+pT212/pT217-tau peptide complex, a 10-fold molar excess of peptide was added.

Crystallization of B324 Fab+pT212/pT217-tau peptide was performed at 9-18 mg/mL in 20 mM MES pH 6.0, 0.2 M NaCl. Initial crystallization screening was performed with the Mosquito crystallization robot by the sitting drop vapor diffusion method at 20° C. using two in house screens and PEGs (Qiagen). Crystals appeared from 0.1 M sodium acetate pH 4.6, 20% PEG 10K and seeds were made by mechanical homogenization with a Seed Bead kit (Hampton Research) for use in further optimization screening.

Data Collection and Structure Determination. A crystal appeared from 0.1 M sodium acetate pH 5.5, 37% PEG200, and it was harvested and flash-cooled in liquid nitrogen without cryoprotection for X-ray diffraction data collection. The crystallography data were collected at the Advanced Photon Source (Argonne, Ill.) on the IMCA-CAT beamline 17-ID-B at 100 K. Diffraction intensities were collected on a Pilatus 6M detector over a 180 rotation with an exposure of 0.5 s per half-degree image. The data were processed with XDS (Kabsch, 2010, Id.) to the maximum resolution of 2.6 Å. The X-ray crystal structure of B324 in complex with pT212/pT217-tau peptide was solved by molecular replacement with Phaser (McCoy et al., 2007, Id.) using a related Fab structure as a search model and refined with Refmac (Murshudov et al., *Acta Crystallogr D Biol Crystallogr.* 53(Pt 3):240-55, 1997) (Table 14). Intermolecular contact distances were calculated with CONTACT (Collaborative Computational Project, 1994, Id.) using a distance cutoff of 4.0 Å and inspected visually with Pymol.

TABLE 14

| X-ray data | |
|---|---|
| Data Collection | |
| Content | B324 + pT212/pT217-tau peptide |
| Mother Liquor | 0.1M NaAct 5.5, 37% PEG 200 |
| Cryo | none |
| Source/Detector | APS IMCA-CAT 17ID-B/Pilatus 6M |
| Wavelength (Å) | 1.000 |
| Temperature (K) | 100 |
| Distance (mm) | 450 |
| Total rotation (°) | 180 ** |
| Exp(sec)/0.5° | 0.5 |
| Space group | I222 |
| Unit cell axes (Å) | 97.60, 104.43, 133.35 |
| Unit cell angles (°) | 90, 90, 90 |
| Molecules/asym. unit | 1 |
| $V_m$ (Å³/Da)/solv.(%) | 3.43/64 |
| Resolution (Å) | 30-2.6 (2.67-2.60) |
| No. measured reflections | 113,798 (6,597) |
| No. unique reflections | 21,019 (1,367) |
| Completeness (%) | 98.6 (87.6) |
| Redundancy | 5.4 (4.8) |
| R-merge | 0.040 (0.417) |

TABLE 14-continued

X-ray data

| | | |
|---|---|---|
| <I/σ> (unavg) | 10.8 | (1.1) |
| <I/σ> (avg) | 24.5 | (3.5) |
| B-factor (Wilson) (Å$^2$) | 69.4 | |
| Refinement Statistics | | |
| No. of atoms | 3331 | |
| $R_{work}/R_{free}$ | 0.230/0.265 | |
| r.m.s.d. from ideal geometry | | |
| Bond lengths (Å) | 0.005 | |
| Bond angles (°) | 1.027 | |
| Average B factors (Å$^2$) | 96.2 | |
| Ramachandran plot | | |
| Residues in favored regions (%) | 95.14% | |
| Residues in allowed regions (%) | 3.94% | |
| Outliers (%) | 0.93% | |

Values for the highest resolution shell are indicated in parentheses.

Figure 11:
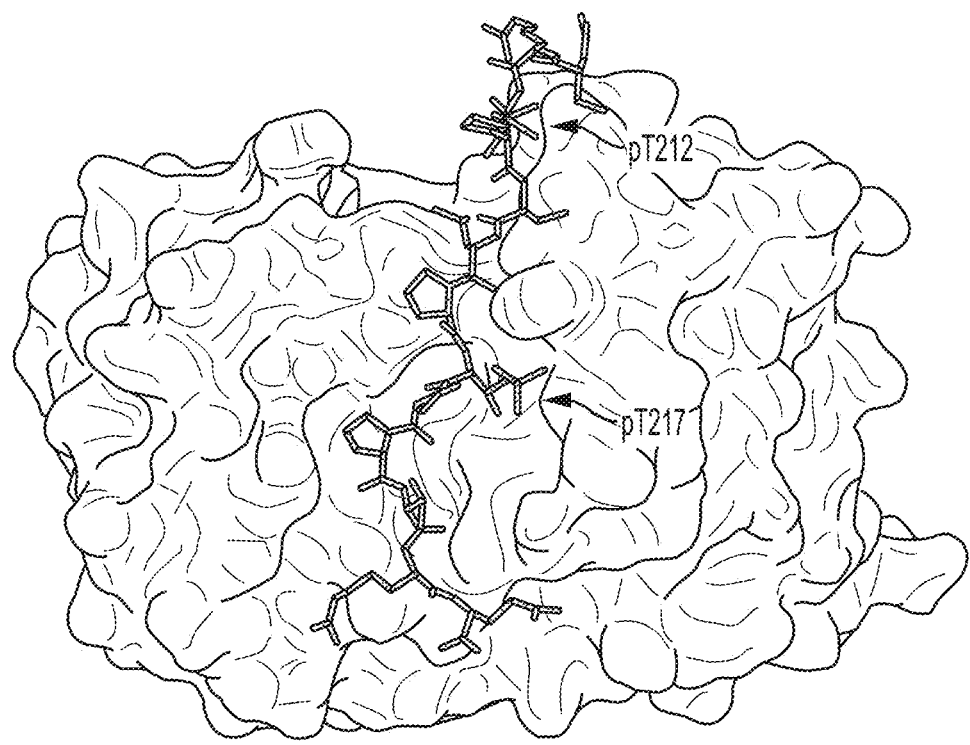
FIG. 11 shows the crystal structure of the B324+pT212/pT217-tau peptide complex, with B324 shown in a space filling representation (light gray), and tau peptide shown in stick representation (black).
Figure 12:
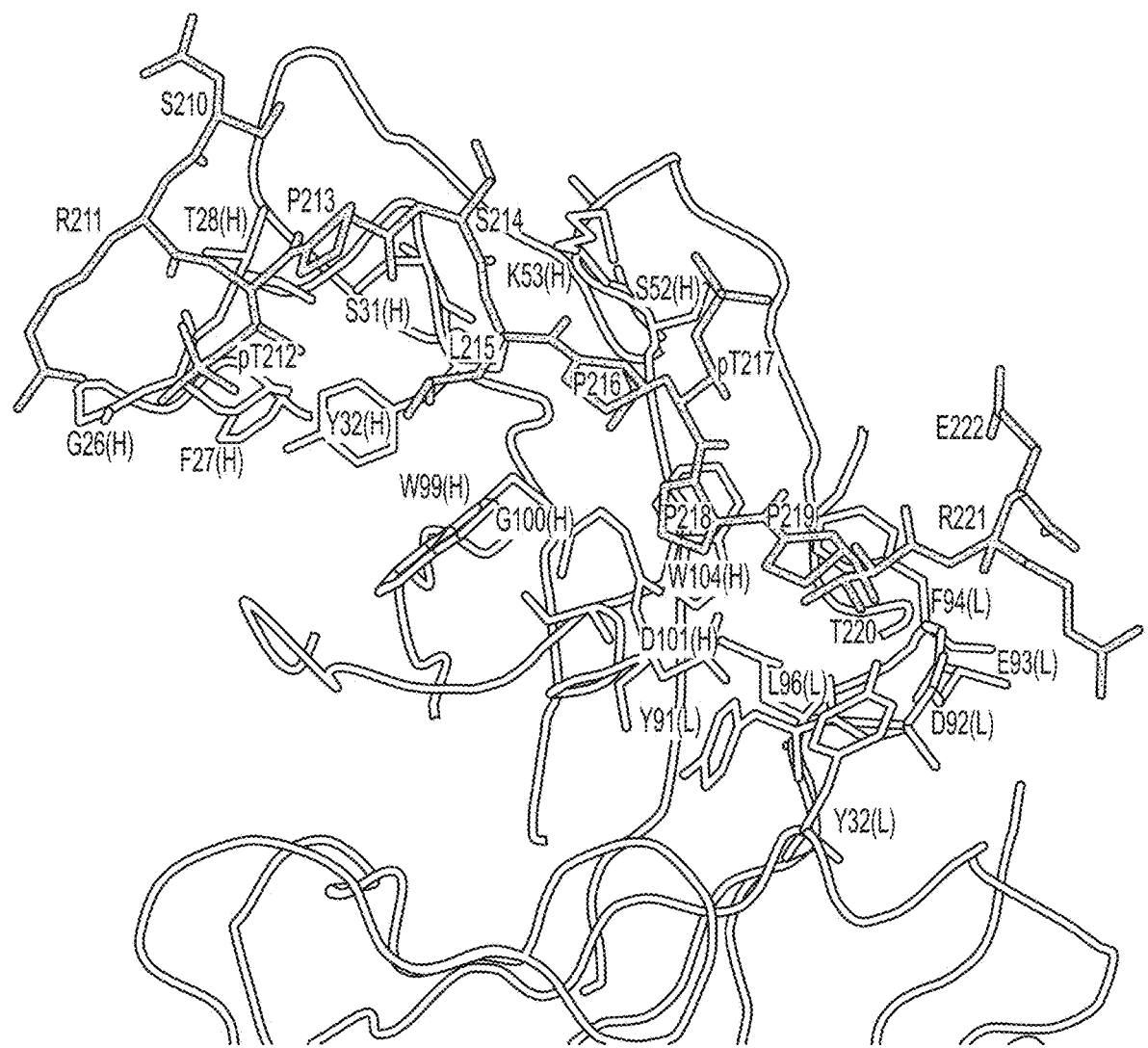
FIG. 12 shows the crystal structure of the B324+pT212/pT217 tau peptide complex, with B324 shown in ribbons (light gray) with its paratope residues shown in stick representation, and tau peptide shown in stick representation (black), note that D92(L) and E93(L) have no electron density for Cγ and sidechain carboxylate atoms.
Figure 13:
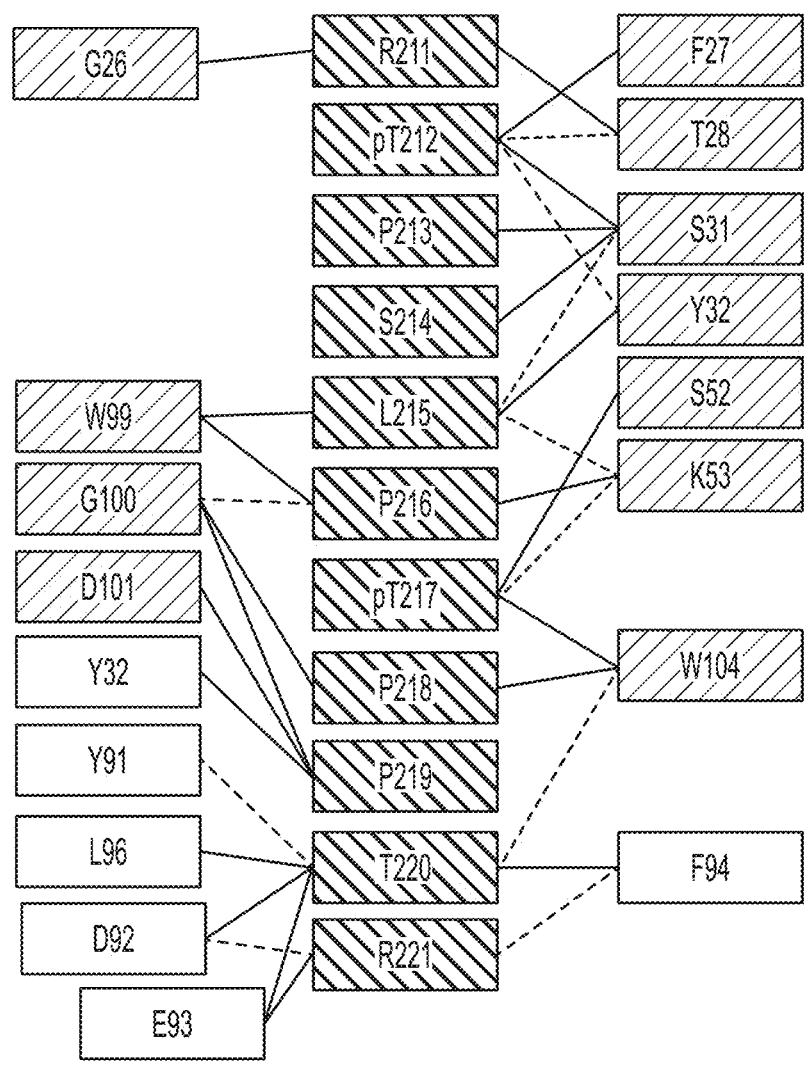
FIG. 13 shows an interaction diagram for the B324+pT212/pT217 tau peptide structure, with the peptide residues shown in the black boxes with white lettering, the VH residues shown in dark gray, the VL residues shown in light gray, and where the dotted lines represent hydrogen bonds and the solid lines represent van der Waals contacts.

Structural Analysis. The overall structure of the B324+pT212/pT217 tau peptide interaction is shown in FIG. 11. The pT212/pT217-tau peptide fits into a groove formed at the interface of B324 VH and VL. The interface between B324 and the pT212/pT217 tau peptide is comprised of van der Waals and electrostatic interactions, which extend from peptide residues 211 to 221 (FIG. 12). The following CDR's are involved in direct binding to pT212/pT217-tau peptide: CDR-H1, CDR-H2, CDR-H3, CDR-L1, CDR-L3. The structure of B324 in complex with pT212/pT217 tau peptide shows that the epitope includes the phosphates of pT212 and pT217. A diagram of the interacting B324 Fab residues and pT212/pT217-tau peptide residues is shown in FIG. 13. Some of the key interactions are as follows: the VH Y32 hydroxyl group and VH T28 hydroxyl group each form hydrogen bonds to different phosphate oxygens of pT212; there are hydrophobic interactions from the sidechains of the VH Y32 and VH W99 to the methyl groups of L215 of the tau peptide; VH K53 forms a salt bridge interaction with tau peptide residue pT217; the sidechain of VH W104 forms a hydrophobic interaction with the pT217 methyl group and a CH-π stacking interaction with P218, and it forms part of the VH/VL interface; the indole amide of VH W104 forms a hydrogen bond with sidechain hydroxyl of T220; there is a hydrophobic interaction between the sidechain of VL Y32 and P219; there is a hydrophobic interaction between VL L96 and the methyl group of T220; and a hydrophobic interaction is formed by VL F94 sidechain and the T220 methyl group. Electrostatic interactions with the phosphates of pT212 and pT217 are critical for the selectivity of B324 for phospho-tau, and hydrophobic interactions additionally contribute to the high affinity of B324 for pT212/pT217-tau peptide (Example 5) and PHF-tau (Example 6). The epitope and paratope of mouse PT3 and B324 are very similar, indicating that neither the epitope nor the paratope are significantly altered after humanization (FIGS. 9 and 13, Tables 8 and 15).

TABLE 15

Epitope and paratope of B324 + pT212/pT217-tau peptide. Residues from B324 VH or VL that interact with pT212/pT217-tau peptide residues are indicated. Hydrogen bonding interactions are indicated with bold type.

| VH | Peptide | VL |
|---|---|---|
| G26, T28 | R211 | |
| F27, T28, S31, Y32 | pT212 | |
| S31 | P213 | |
| S31 | S214 | |
| S31, Y32, K53, W99 | L215 | |
| K53, W99, G100 | P216 | |
| S52, K53, W104 | pT217 | |
| G100, W104 | P218 | |
| G100, D101 | P219 | Y32 |
| W104 | T220 | Y91, D92, E93, F94, L96 |
| | R221 | D92, E93, F94 |

Example 8—Functional Testing in Cellular Assays

Figure 14:
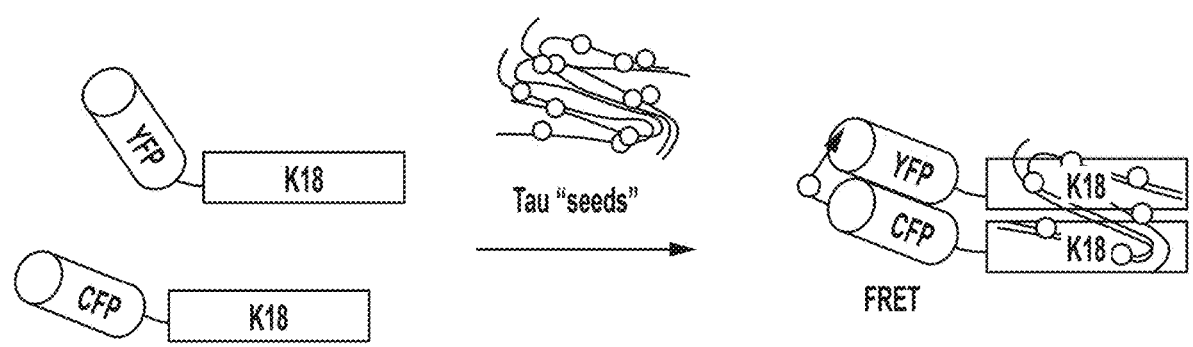
FIG. 14 shows a schematic of the FRET biosensor cell model.

PT3 was tested for inhibition of tau seeding in two types of cellular assays: co-incubation assays and depletion assays. Both assay types make use of HEK cells expressing two chromophore-tagged K18 tau fragments that generate a signal when in close proximity, for example, due to aggregation. When the cells are treated with seeds of aggregated and phosphorylated full length tau derived from different sources, a K18 aggregate is induced that can be quantified by change in bioluminescence resonance energy transfer (BRET) ratio (i.e., BRET assay) or by counting fluorescence resonance energy transfer (FRET)-positive cells using fluorescence-activated cell sorting (FACS) (i.e., FRET assay; FIG. 14) (Holmes et al., 2014, PNAS 111(41):E4376-85).

HEK Cell Homogenates Co-Incubation Assay (BRET Assay)

Figure 15:
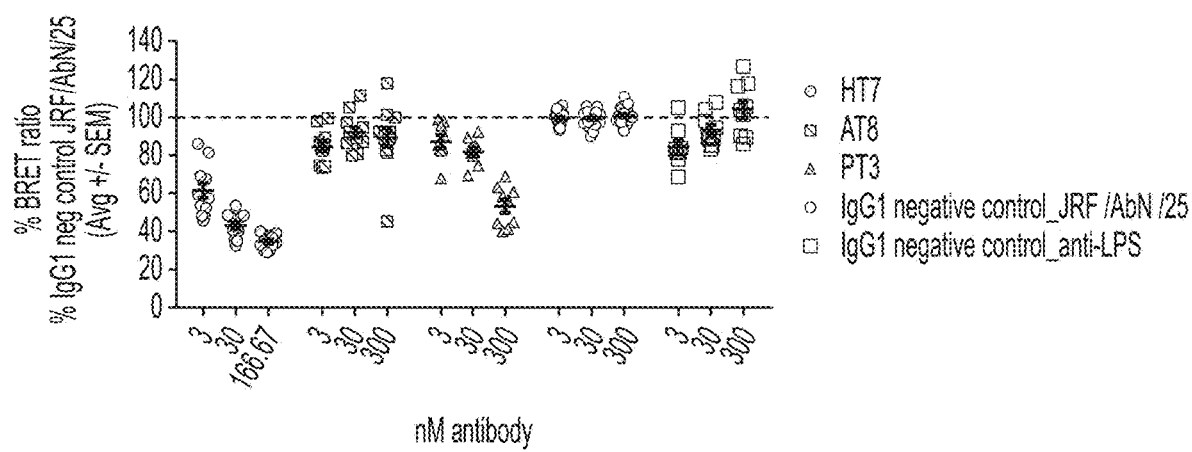
FIG. 15 shows inhibition by PT3 of K18 aggregate induction seeded by HEK cell homogenates containing GFP-tauP301L aggregates, as determined using the BRET assay.

Homogenates containing tau seeds for co-incubation were generated from a stable GFP-tauP301L-overexpressing HEK cell-line that contains K18-induced aggregated GFP-tagged full length tau. The recipient cells were HEK cells stably expressing K18/P301L-NanoLuc and K18/P301L-HaloTag. The tau seeds were co-incubated with the test antibody and the receiving chromophore-K18-containing HEK cells for 72 h. K18 aggregate formation was measured by the change in BRET ratio (590 nm/450 nm). PT3 blocked aggregate induction by 46.97% at 300 nM, 18.02% at 30 nM, and 12.57% at 3 nM (FIG. 15).

Spinal Cord Co-Incubation Assay (FRET Assay)

Figure 16:
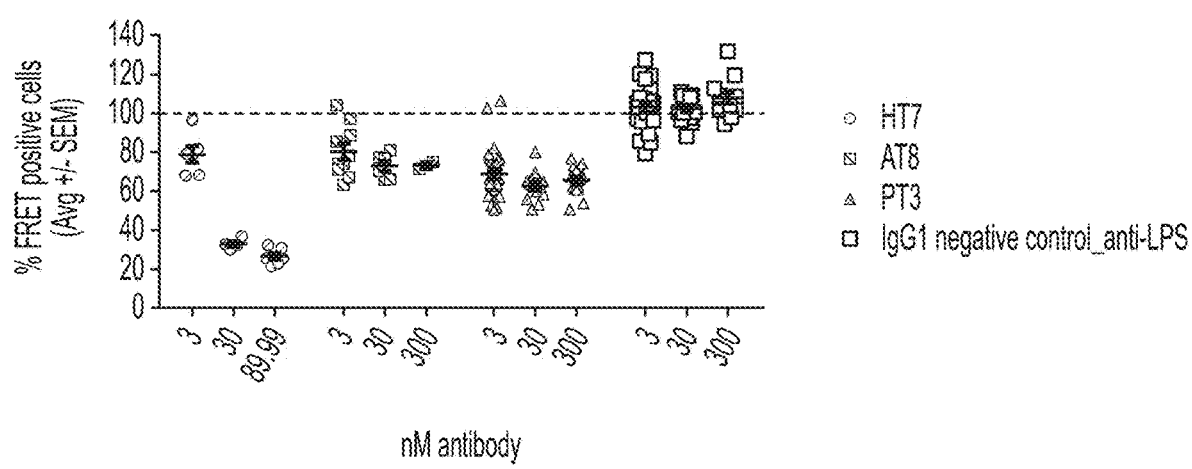
FIG. 16 shows inhibition by PT3 of K18 aggregate induction seeded by TgP301S spinal cord homogenates, as determined using the FRET assay.

Homogenates containing tau seeds for co-incubation were generated from spinal cords from 22- to 23-week-old P301S transgenic animals that contain aggregated transgenic human tau. For increased sensitivity, the recipient cells used in the assay were HEK cells stably expressing K18/P301S-YFP and K18/P301S-CFP. The tau seeds were co-incubated with the test antibody and the receiving chromophore-K18-containing HEK cells for 72 h. K18 aggregate formation was measured by counting FRET-positive cells by FACS. PT3 blocked aggregate induction by 34.03% at 300 nM, 37.02% at 30 nM, and 30.68% at 3 nM (FIG. 16).

Immunodepletion Cellular Assays

To investigate if the maximum percentage inhibition value is related to the density of epitopes on the seeds or to the number of seeds that contain the PT3 epitope, immunodepletion assays were performed. In the immunodepletion assays, the tau seeds were incubated with test antibody and removed from the solution with protein G beads. The depleted supernatant was tested for residual seeding capacity in the chromophore-K18-containing HEK cells and analyzed by FACS as previously described (Holmes et al., *Proc Natl Acad Sci USA.* 111(41):E4376-85, 2014).

Figure 17:
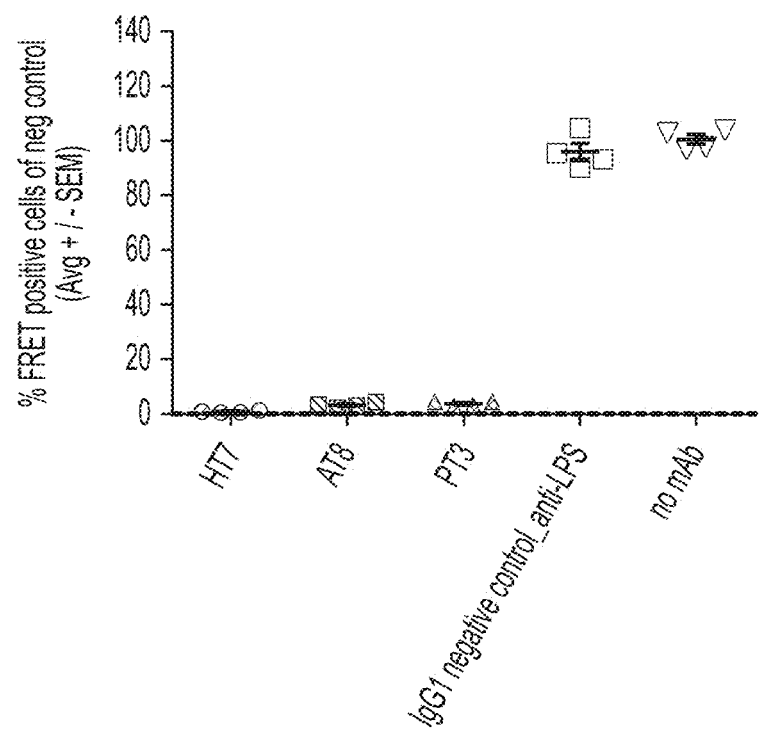
FIG. 17 shows the results of the mouse TgP301S spinal cord extract immunodepletion assay, with data from 2 independent experiments.
Figure 18:
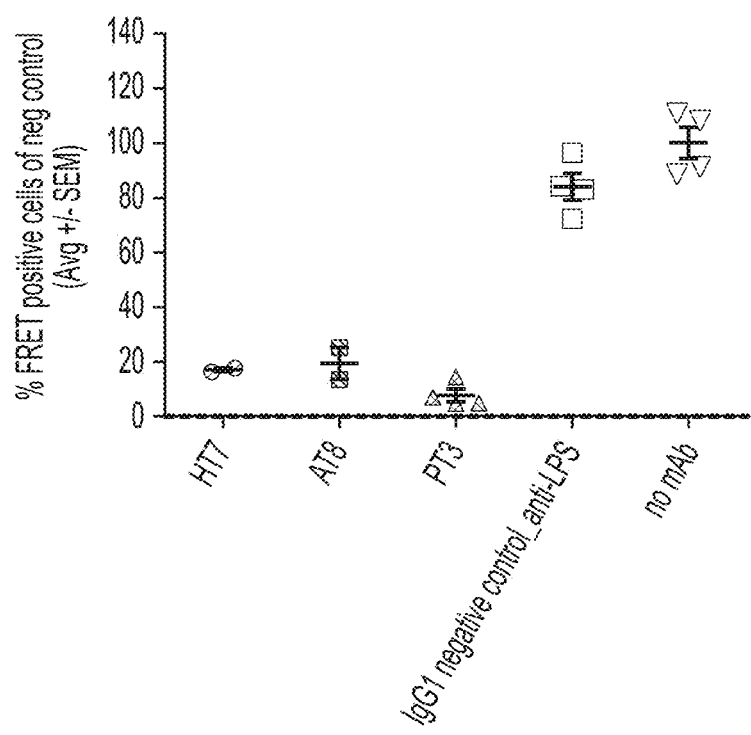
FIG. 18 shows the results of the human AD brain extract immunodepletion assay, with data from 2 experiments (except in the case of HT7 and AT8, for which n=1). PT3 inhibits tau seeding as determined using the FRET assay.

Homogenates containing tau seeds for immunodepletion were generated from spinal cords from 22- to 23-weeks-old P301S transgenic animals (FIG. 17) or from cryopreserved human AD brain tissue (FIG. 18). In the human AD brain immunodepletion assay, the supernatant after depletion was tested in the presence of the transfection reagent Lipofectamine2000 to obtain an acceptable assay window. The tau seeding could be almost completely (>90%) depleted with PT3 in both the spinal cord extracts and total homogenates from human AD brain (FIGS. 17 and 18).

Results

PT3 inhibited tau seeds derived from both HEK cell lysates and TgP301S spinal cord lysates. The maximum inhibition obtained in the assays varied for different anti-phospho-tau antibodies and for the different seeds (Table 16). The observed inhibition values for PT3 at 300 nM were 46.97±5.87% for HEK cell seeds, and 34.03±2.05% for TgP301S spinal cord extracts. The different maximal inhibition values for phospho-tau antibodies in the different cellular assays can point to differences in phosphorylation status of the tau seeds used. Tau seeds generated in TgP301S spinal cord are of neuronal origin and are expected to have more similarities to PHF-tau than tau seeds from HEK cell origin, and this could explain the generally higher efficacies observed with phospho-tau antibodies against spinal cord extracts versus HEK cell lysates.

The tau seeding could be almost completely depleted with PT3 in both the spinal cord extracts and total homogenates from human AD brain, and this result suggests that lack of full inhibition in the co-incubation experiments with the spinal cord seeding material was not resulting from the presence of seeds devoid of PT3 epitopes but rather from limited epitope density on the seeds.

TABLE 16

Summary of results from functional testing in the cellular assays

| MAb | BRET/GFP-tauP301L co-incubation assay | FRET/P3015 spinal cord co-incubation assay | FRET/P301S spinal cord immunodepletion assay | FRET/human AD brain homogenate immuno-depletion assay |
|---|---|---|---|---|
| PT3 | 46.97 ± 5.87 | 34.03 ± 2.05 | 96.24 ± 0.43 | 92.24 ± 2.30 |
| AT8 | 10.52 ± 9.48 | 26.4 ± 1.74 | 96.71 ± 0.42 | 80.69 ± 5.79 |
| HT7 | 65.44 ± 1.08$^a$ | 73.51 ± 1.78$^b$ | 99.16 ± 0.21 | 82.99 ± 0.68 |

Unit is % of negative control, average of different experiments; antibody concentration in all assays was 300 nM except for $^a$inhibition at 166.67 nM and $^b$inhibition at 89.99 nM.

The mechanism of action for tau antibody therapy is still a matter of debate and multiple mechanisms have been proposed. Antibody-mediated clearance of extracellular seeds by microglial cells has recently been suggested as one dominant mechanism of action (Funk et al., *J Biol Chem.* 290(35):21652-62, 2015 and McEwan et al., 2017, PNAS 114:574-9). In this context, immunodepletion of human-brain-derived seeding material can be considered the most translational cellular result, and the high efficacy of the parent mouse antibody PT3 in this type of cellular assay suggests that the HFA versions of PT3 will be effective therapeutics.

Example 9—In Vivo Efficacy of Murine PT3 in the ePHF Injection Model

To evaluate tau antibody efficacy in vivo, mice displaying brain tau pathology are essential model systems (Julien et al., *Methods Mol Biol.* 849:473-91, 2012). Several of these models have been described, and they can generally be divided in three groups: 1) tau transgenic mice overexpressing WT or mutant (e.g., P301L or P301S) tau with the mutants showing severe pathology after 5-9 months, depending on the strain (Allen et al., *J Neurosci.* 22(21): 9340-51, 2002; Scattoni et al., *Behav Brain Res.* 208(1): 250-7, 2010; Terwel et al., *J Biol Chem.* 280(5):3963-73, 2005; Yoshiyama et al., *Neuron.* 53(3):337-51, 2007); 2) mice with spatio-temporally-regulated expression of mutant tau (e.g., P301L) (Liu et al., *Brain Imaging Behav.* 6(4): 610-20, 2012) or a pro-aggregating fragment (e.g., K18) (Mocanu et al., *J Neurosci.* 28(3):737-48, 2008); and 3) mice with expression of both mutant tau and APP displaying both plaque and tau pathologies (Oddo et al., *J Neurochem.* 102(4):1053-63, 2007).

While mice expressing mutant tau develop a strong pathology, the onset of pathology can vary between animals, causing variability in studies, and the relative contribution of cell-autonomous tau aggregation and spreading to the overall tau aggregation signal is not clear. Therefore, models that can be used to effectively study tau seeding and spreading (e.g., de Calignon et al., 2012, *Neuron.* 73(4):685-97, 2012; Liu et al., Id.) are of high value. The translational value of such models is further strengthened by the finding that injection of ALZ17 mice (a strain expressing normal human tau) with brain homogenates derived from different tauopathies induces the formation of tau inclusions with a morphology that resembles tauopathy in the human brain. For example, injection of mice with material from Argyrophilic grain disease samples resulted in deposits with a spheroid or comma-like structure characteristic of the disease itself, and AD-like tau pathology was observed in mice injected with AD material (Clavaguera et al., 2013, PNAS 110(23):9535-40).

Thus, a transgenic P301L mouse injection model has been established, wherein a pro-aggregating fragment of tau, such as synthetic K18 fibrils (Li and Lee, *Biochemistry.* 45(51): 15692-701, 2006) or PFH-tau seeds derived from human AD brain, is injected in cortical or hippocampal regions of P301L transgenic mouse models at an age at which cell-autonomous aggregation has not started. The injection model aims to mimic the critical extracellular seeding component of tau spreading. The injected K18 or PHF-tau seed induces tauopathy at the injection site and, to a lesser degree, at the connected contralateral region (Peeraer et al., *Neurobiol Dis.* 73:83-95, 2015). The model enables testing of the anti-seeding potential of antibodies, such as anti-tau antibodies of the invention, when co-injected with the AD-brain-derived PHF-tau seeds or the K18 fibrils (Iba et al., 2015, *J Neurosci.* 33(3):1024-37, 2013; Iba et al., *Acta Neuropathol.* 130(3):349-62).

Figure 19G:
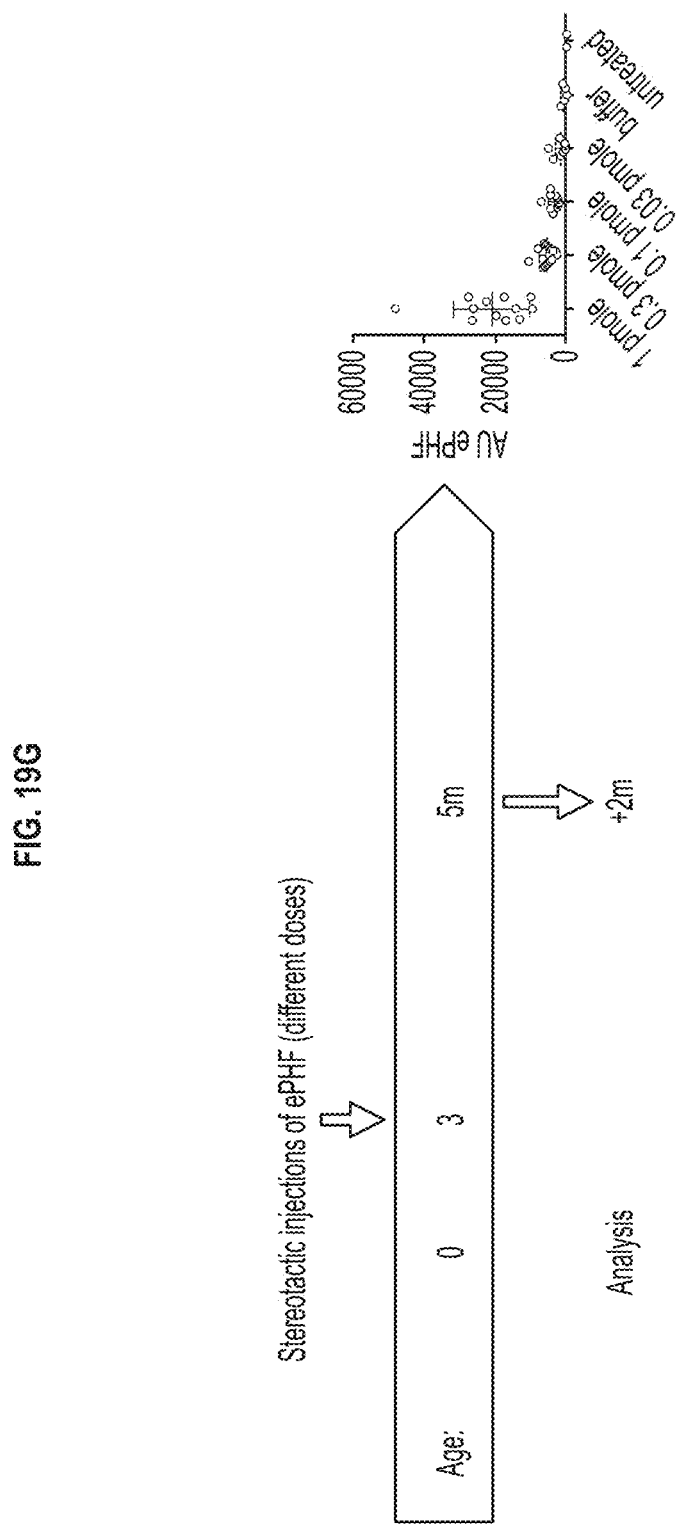

A schematic of the transgenic P301L mouse injection model is shown in FIG. 19A-19G. Briefly, cortical injection of a sarcosyl-insoluble fraction of post-mortem AD brain triggers a slowly progressing increase of tau aggregation. In the injected hemisphere, the first signals are measured 1 month after injection and progress further 3 months after injection. Five months after injection, some animals start to form tangles driven by the P301L mutation (Terwel et al., 2005, Id.). AT8 staining levels increase between 1 and 3 months (FIGS. 19C-19D and 19E-19F), so antibody efficacy experiments are analyzed 2 months after co-injection. Additionally, hippocampal injection of a sarcosyl-insoluble fraction of post-mortem AD brain triggers a dose-dependent progressing increase of tau aggregation measured by MesoScale Discoveries (MSD) analysis of sarcosyl insoluble fractions from the injected hemispheres (FIG. 19G).

Animal Treatment and Intracranial Injections

For injection studies, transgenic tau-P301L mice, expressing the longest human tau isoform with the P301L mutation (tau-4R/2N-P301L) (Terwel et al., 2005, Id.) were used for surgery at the age of 3 months. All experiments were performed in compliance with protocols approved by the local ethical committee. For stereotactic surgery, the mice received a unilateral (right hemisphere) injection in the cortex (AP +2.0, ML +2.0 from bregma, DV, 2.7 mm from dura) or hippocampus (AP −2.0, ML +2.0 (from bregma), DV 1.8 mm (from dura)) 3 µl (speed 0.25 µl/min) with a sarcosyl insoluble prep from postmortem AD tissue (enriched paired helical filaments, ePHF) in the presence or absence of monoclonal antibodies. In the case of intraperitoneal (IP) injections with antibodies or saline, treatments (20 mg/kg, 2×/week) were started 1 week before the intracranial injection and continued until the mice were sacrificed for dissection (2 months after intracranial injection).

Extraction Procedure

Mouse tissue from the injected hemisphere was weighed and homogenized in 6 volumes of homogenization buffer (10 mM Tris HCl (pH7.6). The homogenate was centrifuged at 27 000×g for 20 minutes, and after taking an aliquot from the resulting supernatant (total homogenate), 1% N-lauroyl-sarcosine was added. After 90 minutes (900 rpm, 37° C.), the solutions were again centrifuged at 184 000×g for 1 hour. The supernatants were kept as sarcosyl-soluble fraction, whereas the pellet containing the sarcosyl-insoluble material was resuspended in homogenization buffer.

Biochemical Analysis

Coating antibody (either anti-AT8 or a total tau antibody) was diluted in PBS (1 µg/ml) and aliquoted into MSD plates (30 uL per well) (L15XA, Mesoscale Discoveries), which were incubated overnight at 4° C. After washing with 5×200 µl of PBS/0.5% Tween-20, the plates were blocked with 0.1% casein in PBS and washed again with 5×200 µl of PBS/0.5% Tween-20. After adding samples and standards (both diluted in 0.1% casein in PBS), the plates were incubated overnight at 4° C. Subsequently, the plates were washed with 5×200 µl of PBS/0.5% Tween-20, and SULFO-TAG™ conjugated detection antibody in 0.1% casein in PBS was added and incubated for 2 hr at room temperature while shaking at 600 rpm. After a final wash (5×200 µl of PBS/0.5% Tween-20), 150 µl of 2× buffer T was added, and plates were read with an MSD imager. Raw signals were normalized against a standard curve consisting of 16 dilutions of a sarcosyl insoluble prep from postmortem AD brain (ePHF) and were expressed as arbitrary units (AU) ePHF. Statistical analysis (ANOVA with Bonferroni post test) was performed with the GraphPad prism software.

Results

Figure 20:
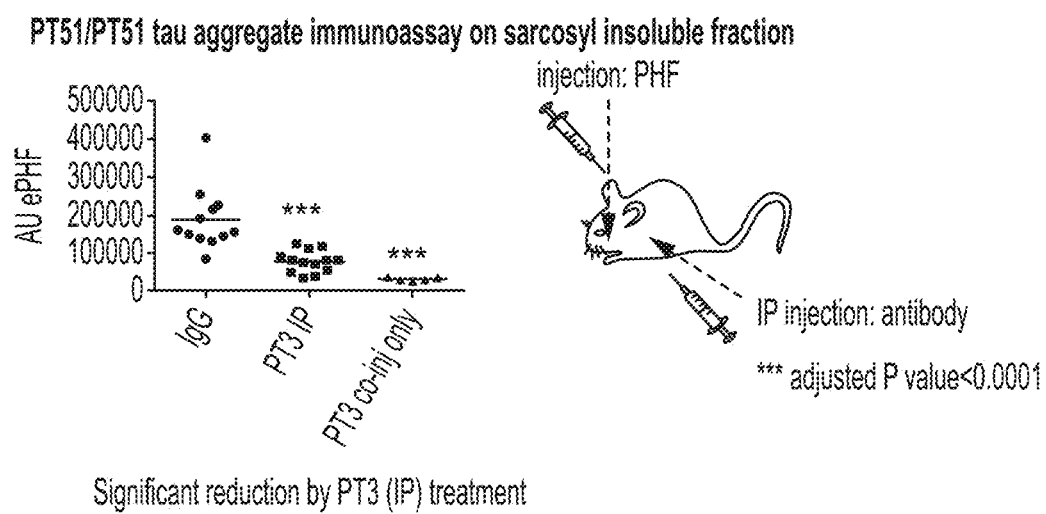
FIG. 20 shows the effect on tau aggregation of peripheral administration (IP) of PT3 followed by seeding with AD-brain-derived PHF-tau in transgenic mice expressing mutant human P301L tau.
Figure 21:
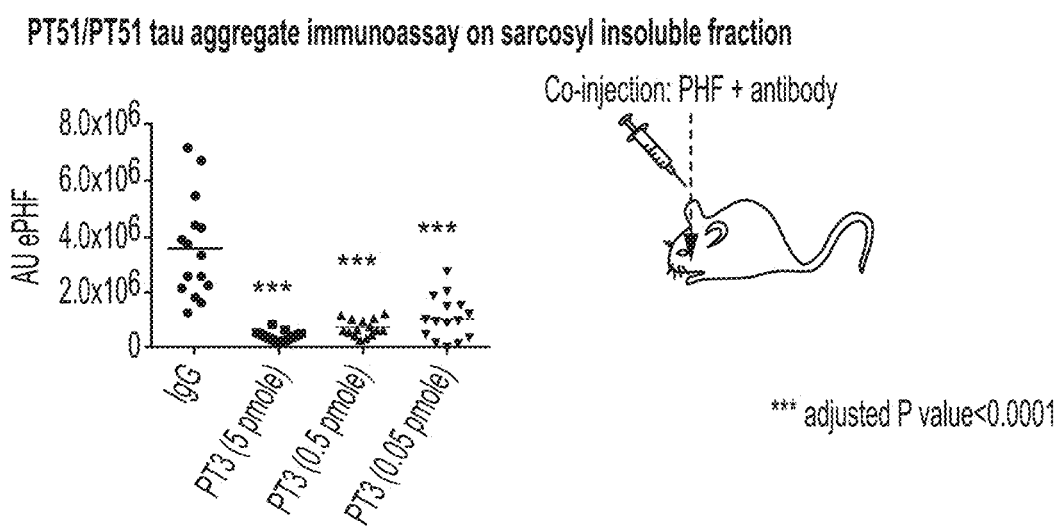
FIG. 21 shows the effect on tau aggregation of co-injection of decreasing doses of PT3 followed by seeding with AD-brain-derived PHF-tau in transgenic mice expressing mutant human P301L tau.

Activity of mouse PT3 under the cortical co-injection model (FIG. 19A-19G) was confirmed in four independent studies. Mice were dosed peripherally according to Table 17 and results are shown in FIG. 20. Further improvement of the model (FIG. 19D) allowed lowering the dose of ePHF-tau and the dose of the co-injected antibody as shown in Table 18 with results shown in FIG. 21. Using this lower dose of ePHF-tau, PT3 was also found to have a significant effect in lowering aggregated tau when administered peripherally (P<0.0001; FIG. 21).

TABLE 17

Peripheral Dosing

| Group | Amount of pmole ePHF | Amount pmole Ab co-injection | Antibody IP | n |
|---|---|---|---|---|
| IgG | 0.2 | 5 | 20 mg/kg (2x/w) | 12 |
| PT3 | 0.2 | — | 20 mg/kg (2x/w) | 13 |
| PT3 | 0.2 | 5 | | 5 |

TABLE 18

Co-Injection Dosing

| Group | Amount of pmole ePHF | Amount pmole Ab co-injection | n |
|---|---|---|---|
| IgG | 0.2 | 5 | 14 |
| PT3 | 0.2 | 5 | 15 |
| PT3 | 0.2 | 0.5 | 15 |
| PT3 | 0.2 | 0.05 | 15 |

Co-injection of ePHF and PT3 isotypes, including the PT3-HFA IgG2a variant (which contains the variable regions VH92 (SEQ ID NO:27) and VL77 (SEQ ID NO:31) on mIgG2a/kappa constant regions) according to the layout in FIG. 19A, attenuated ePHF-induced tau aggregation in P301L mice (FIG. 22A-22C). Injections were done in the cortex. (not the hippocampus). The effect was observed in the injected hemisphere (biochemistry data, FIG. 22B) and in the non-injected hemisphere (IHCAT100 staining, FIG. 22C). Both the IgG2a and IgG1 isotypes significantly reduced the induction of tauopathy when co-injected with the AD-brain-derived PHF-tau (p<0.0001). The results were confirmed in IHC in the contralateral hemisphere.

While the invention has been described in detail, and with reference to specific embodiments thereof, it will be apparent to one of ordinary skill in the art that various changes and modifications can be made therein without departing from the spirit and scope of the invention.

Example 10—Comparison of PSP Tau and AD Tau

Progressive supranuclear palsy (PSP) is a rare and fatal neurodegenerative disorder characterized by parkinsonism, postural instability and falls, supranuclear gaze palsy, and dementia (Steele et al., 1964, Archives of Neurology 10:333-359). Pathologically there is a preferential accumulation of 4-repeat (4R) tau in the brainstem and basal ganglia as well as other brain regions (Dickson D W. Handbook of Clinical Neurology 2008; 89:487-491; Williams & Lees, 2009, The Lancet Neurology 8:270-279). Given the absence of other pathologies such as amyloid, PSP is considered a primary tauopathy, and animal model data suggest that PSP tau may undergo seeding analogous to what is hypothesized to occur in AD (Clavaguera et al. 2013, PNAS 110:9535-9540; Sanders et al., 2014, Neuron 82:1271-1288). As such, PSP can be treated with the antibody of the invention. A series of experiments was undertaken to characterize the similarities of PSP tau and AD PHF tau.

Methods

Human brain tissue: Cryopreserved tissue from two typically highly affected brain regions from clinically diagnosed PSP (n=5) patients (nucleus caudatus=CAU and putamen=PUT) and a less affected brain region (gyrus frontalis superior=GFS) and the same brain regions for two control (=no tauopathy) patients were obtained from the Netherland Brain Bank. Tissue was used for analysis with both aggregation assays and immunohistochemistry staining described below. Cryopreserved tissue from 9 sporadic AD patients was obtained from the University of Pennsylvania and used for analysis with aggregation assays. Cryopreserved tissue from 1 AD patient was obtained from the University of Newcastle and used for immunohistochemistry staining.

Homogenization of brain tissue: Cryopreserved tissue was homogenized in 10 mM Tris, 150 mM NaCl, pH 7.4, filter: 0.22 μm+Complete mini EDTA-free protease inhibitors (Roche, cat #11 836 170 001) with a dounce homogenizer at 1000 rpm for 10 strokes to obtain 10% w/v homogenates. The homogenates were centrifuged at 27.000×g, 10 min at 4° C. and supernatant was stored in aliquots at −80° C. until used.

Aggregation assays: An aggregation specific sandwich MSD immunoassay was performed in which the phospho-tau antibodies AT8 and PT3 were used as capture and detection antibodies. Coating antibody was diluted in PBS (1 μg/ml) and aliquotted into MSD plates (30 uL per well) (L15XA, Mesoscale Discoveries) incubate ON at 4° C. After washing with 5×200 μl of PBS/0.5% Tween-20, plates are blocked with 0.1% casein in PBS and washed again with 5×200 μl of PBS/0.5% Tween-20. After adding samples and standards (both diluted in 0.1% casein in PBS) plates are incubated ON at 4° C. Subsequently, plates are washed with 5×200 μl of PBS/0.5% Tween-20 and SULFO-TAG™ conjugated detection antibody in 0.1% casein in PBS is added and incubated 2 hrs at RT while shaking at 600 rpm. After a final wash (5×200 μl of PBS/0.5% Tween-20), 150 μl of 2× buffer T is added and plates are read with MSD imager. Raw signals are normalized against a standard curve consisting of 7 dilutions of one AD total brain homogenate and expressed as interpolated values as percentage of this standard.

Immunohistochemistry: Cryopreserved human brain tissue was sliced with a cryostat (20 μm thickness) and stored at −80° C. before use. Sections were dried, followed by formalin fixation, blocking of endogenous peroxidase with 3% hydrogen peroxide (DAKO, Glostrup, Denmark, S2023) and permeabilization in PBS1×+0.3% Triton X-100 during 1 hour. Primary antibodies (PT3 0.4 μg/ml; AT8 0.4 μg/ml) were diluted in antibody diluent with background reducing components (DAKO, S3022) and applied to the sections for 1 hour. After extensive washing, slides were incubated with HRP-conjugated anti-mouse secondary antibody (Envision, DAKO, K4000), followed by chromogenic DAB labelling (DAKO, K4368). Slides were counterstained with hematoxylin, dehydrated and mounted with organic mounting medium (Vectamount, Vector labs, Burlingame, Calif., USA, H-5000). Imaging was performed with a Hamamatsu NanoZoomer 2.0 rs (Hamamatsu Photonics, Shizuoka, Japan).

Results

Figure 23A:
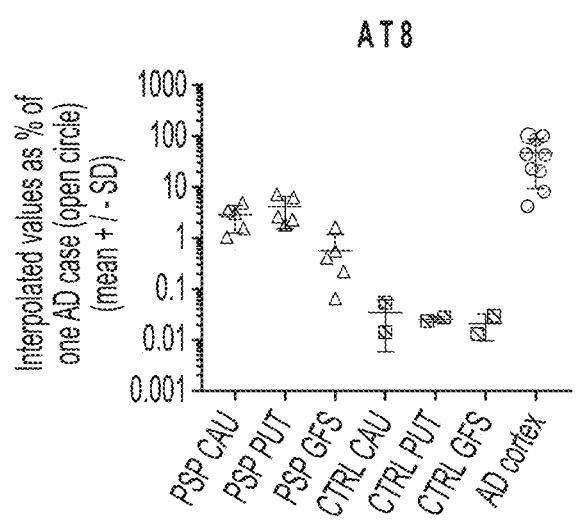
FIGS. 23A-23B show levels of aggregated tau in brain homogenates derived from PSP patients compared to levels of brain homogenates derived from AD patients. Monoclonal antibodies used were (A) AT8 and (B) PT3.
Figure 23B:
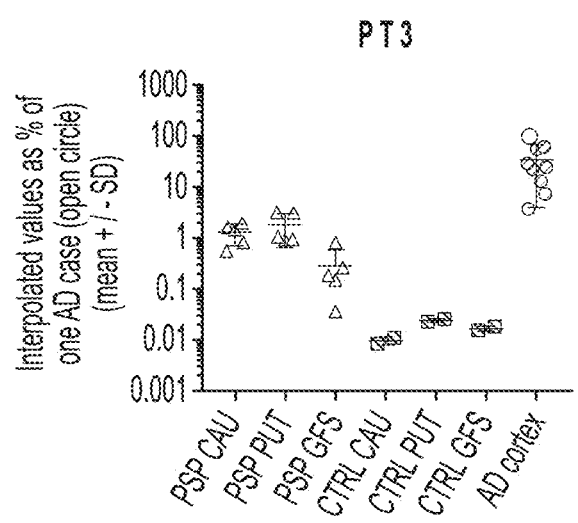

Aggregation assays: Aggregation assays were conducted to characterize the degree of phosphorylation of PSP tau. PT3 reactive aggregates were present in PSP brain, although the levels of aggregation were lower than in AD brain (FIG. 23A-23B). Results obtained with the reference antibody AT8 were similar to those observed with PT3. These results suggest that all phosphorylation sites evaluated using various phospho-tau antibodies are present on PSP tau although there are fewer tau aggregates in PSP compared to AD.

Immunohistochemistry: Staining with the PT3 antibody on cryosections from AD or PSP brain demonstrated staining in the anatomical regions (i.e., the caudate and putamen) affected in PSP (FIG. 24A-24J). Neuropathological hallmarks of PSP, including tau+ neurons and tufted astrocytes, were detected by the phospho-tau antibody PT3. Results obtained with AT8 were similar to those observed with PT3.

Conclusions

Available data suggest that PT3 binds to the tau of PSP.

Example 11—Affinity Maturation of PT3-HFA

SPR Binding Characterization of Affinity Matured Antibodies to PHF-Tau

Affinity matured monoclonal antibodies were tested for binding to PHF-tau isolated from Alzheimer's disease brain. Binding kinetics and affinity studies were performed using ProteOn XPR36 system (Bio Rad, Hercules, Calif.) at 25° C. with PBS pH 7.4, supplemented with 3 mM EDTA, and 0.005% Tween 20 as running or system buffer.

A GLC sensor chip was covalently immobilized with a mouse anti-tau antibody, HT7 (ThermoFisher, catalog #MN1000) using the vendor recommended protocol for amine-coupling chemistry (~5000 response units, RU). The coupling buffer was 10 mM, pH 4.5 sodium acetate. PHF-tau was prepared by 2-times centrifugation at 5000×g in 5° C. for 10 min. The supernatant from the second centrifugation was diluted in running buffer (1/125) and capture-coupled to the HT7 immobilized surface (~300 RU). After capture-coupling, the surface was activated and deactivated to generate a homogenous PHF-tau surface for antibody binding studies. The anti-tau antibodies and their Fabs (prepared in running buffer, 0.024-75 nM at 5-fold dilutions) were injected at 50 μL/min over the PHF-tau surface to measure binding. The association and dissociation profiles were monitored for 4 minutes and 2 hours, respectively. After dissociation, the sensor chip was regenerated using multiple injections of 10 mM Glycine pH 2.0 and the running buffer. A reference surface (without any PHF-tau) was used to monitor non-specific binding of the injected mAbs or Fabs. HT7 antibody was used as a positive control. The binding sensorgrams for mAbs were fit using a bivalent binding model where the apparent affinity or avidity-driven binding ($K_D$) was reported as the ratio of off-rate and on-rate ($k_{off}/k_{on}$). A 1:1 Langmuir binding model was used for kinetics analysis of Fabs.

The parent human antibody (B296) showed tight binding to PHF-tau ($K_D$=6.2 pM) and was dominated by very slow off-rate, where no more than 5% dissociation of the mAb was observed over 2 hours (Table 19, FIGS. 25A-25H). The affinity-matured antibodies showed an improvement in binding to PHF-tau with affinities ranging from 1.8-2.5 pM. B711 and B809 showed a 3-fold improvement in on-rates compared to the parent antibody, the off-rates, however, were virtually indistinguishable between all antibodies (FIG. 25A-25H). The Fabs overall showed an order magnitude weaker binding to PHF-tau compared to their corresponding mAbs, suggesting an avidity-driven binding of the mAbs to PHF-tau. B324 (Fab of the parent mAb, B296), bound to PHF-tau with an intrinsic affinity of 63.2 pM. The Fabs of the affinity-matured mAbs showed a similar improvement in affinities with values ranging from 15.6-31 pM. The two Fabs, B330 (Fab of B711) and B332 (Fab of 809), furthermore showed a similar 3-4-fold improvement in on-rates as their corresponding mAbs.

TABLE 19

ProteOn SPR binding kinetics and affinities for affinity-matured mAbs and their Fabs with PHF-tau

| Samples | Description | $k_{on}$ (×10$^6$ 1/Ms) | $k_{off}$ (×10$^{-5}$ 1/s) | $K_D$ (pM) |
|---|---|---|---|---|
| B296 (mAb) | Humanized parent mAb | 1.89 ± 0.09 | 1.17 ± 0.09 | 6.2 ± 0.5 |
| B711 (mAb) | affinity matured B296 | 6.17 (5.72-6.61) | 1.13 (1.08-1.17) | 1.8 (1.6-2.1) |
| B809 (mAb) | affinity matured B296 | 6.45 ± 1.18 | 1.27 ± 0.15 | 2.0 ± 0.5 |
| B333 (mAb) | affinity matured B296 | 2.68 ± 0.23 | 0.68 ± 0.08 | 2.5 ± 0.4 |
| B324 (Fab) | Fab of B296 | 1.43 ± 0.06 | 9.03 ± 0.08 | 63.2 ± 2.8 |
| B330 (Fab) | Fab of B711 | 4.60 (4.53-4.66) | 7.15 (6.94-7.36) | 15.6 (15.3-15.8) |
| B332 (Fab) | Fab of B809 | 4.64 ± 0.29 | 12.0 ± 0.12 | 25.8 ± 1.7 |
| B331 (Fab) | Fab of B333 | 1.72 ± 0.07 | 5.31 ± 0.10 | 31.0 ± 1.5 |

N = 2-3 replicates within one experiment. Values reported as average ± SD (or range)

Binding to Phosphopeptide by ELISA

Figure 26A:
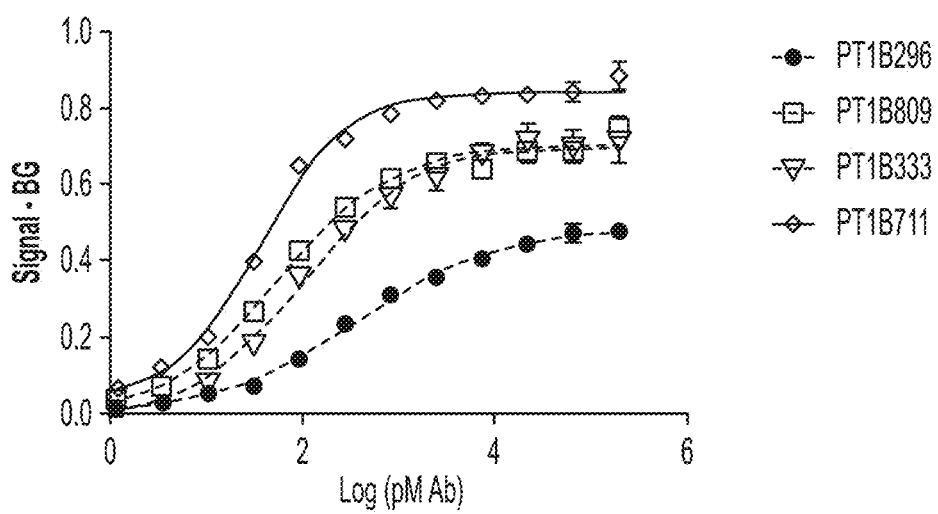
FIGS. 26A-26B show binding of PT3-HFA and affinity matured variants to pT212/pT217 peptide in a direct ELISA experiment using (A) mAbs or (B) Fabs.
Figure 26B:
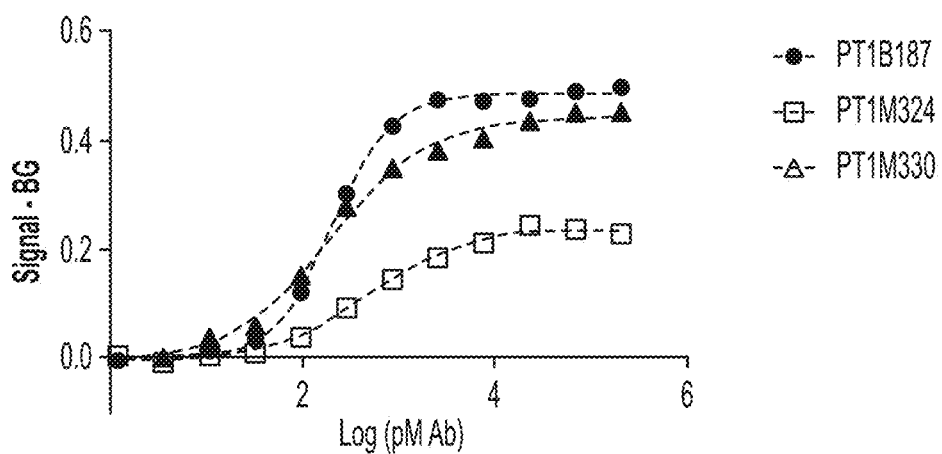

Binding to tau phospho-peptide was analysed by ELISA where peptide (10 ng/mL) was directly coated to the plate overnight. After washing the plate and blocking with 0.1% casein in PBS, plates were incubated with different concentrations of HFA-PT3 (B296) and affinity matured variants of HFA-PT3 (B809, B333 and B711) mAbs (FIG. 26A). After incubation with antibodies, plates were washed and 50 µL per well of HRPO labelled anti-Fab antibody (Jackson Immunoresearch laboratories) (diluted 1:10000 in blocking buffer). After another washing step detection was performed with "One step" TMB (Thermo Scientific) according to the manufacturers' instructions. Plates were analysed in EnVision® 2102 Multilabel Reader (Perkin Elmer, Waltham, Mass., USA). Binding curves were generated using GraphPad Prism7.0 software. From the binding curves in FIG. 26A it can be seen that B296 showed the lowest affinity while the B711 showed most potent binding in comparison to B296 but also to B333 and B809. This suggests that B711 is the humanized PT3 antibody with the strongest affinity for the pT217 peptide. A similar experiment with Fabs (FIG. 26B) demonstrated that M333 (the Fab of B711) had similar peptide binding in comparison to B187, the Fab of parent PT3 molecule. Again, M324 (Fab of B296, HFA-PT3) displayed weaker binding in comparison to the parent Fab and affinity matured variants of PT3-HFA.

TABLE 20

Summary of results from pT217 binding with ELISA

| | $EC_{50}$ (pM) | |
|---|---|---|
| | Average | SD |
| Fabs | | |
| B187 | 109.82 | 73.70037 |
| M324 | 340.8333 | 121.6609 |
| M330 | 106.5133 | 62.22259 |
| mAbs | | |
| B296 | 433.425 | 139.2647 |
| B809 | 91.6675 | 59.01867 |
| B333 | 164.345 | 92.99161 |
| B711 | 70.745 | 48.86815 |

N = 2 replicates within at least 2 experiments.
Values reported as average ± SD

REFERENCES

Abhinandan and Martin, *Mol Immunol.* 45:3832-9, 2008
Adams et al., *Acta Crystallogr D Biol Crystallogr.* 66(Pt 2):213-21, 2010
Allen et al., *J Neurosci.* 22(21):9340-51, 2002
Almagro, *Mol Recognit.* 17:132-43, 2004
Asuni et al., *J Neurosci.* 27:9115-29, 2007
Boutajangout et al., *J Neurochem.* 118:658-67, 2011
Boutajangout et al., *J Neurosci.* 30:16559-66, 2010
Brunden et al., *Nat Rev Drug Discov.* 8:783-93, 2009
Butner and Kirschner, *J Cell Biol.* 115(3):717-30, 1991
Chai et al., *J Biol Chem.* 286:34457-67, 2011
Chothia and Lesk, *J Mol Biol.* 196:901-17, 1987
Clavaguera et al., *Nat Cell Biol.* 11:909-13, 2009
Clavaguera et al., *Proc Natl Acad Sci USA.* 110(23):9535-40, 2013
Clavaguera et al., *Proc Natl Acad Sci USA.* 110(23):9535-40, 2013
Collaborative Computational Project, Number 4, *Acta Crystallogr D Biol Crystallogr.* 50(Pt 5):760-3, 1994
Collin et al., *Brain.* 137(Pt 10):2834-46, 2014
de Calignon et al., *Neuron.* 73(4):685-97, 2012
Emsley and Cowtan, *Acta Crystallogr D Biol Crystallogr.* 60(Pt 12 Pt 1):2126-32, 2004
Epitope Mapping Protocols in Methods in Molecular Biology, Vol. 66, G. E. Morris, Ed. (1996)
Fishwild et al., *Nat Biotechnol.* 14:845-51, 1996
Fransson et al., *J Mol Biol.* 398(2):214-31, 2010
Frost et al., *J Biol Chem.* 284:12845-52, 2009
Funk et al., *J Biol Chem.* 290(35):21652-62, 2015
Goedert et al., *Biochemical J.* 301(Pt3):871-877
Hanger et al., *Trends Mol Med.* 15:112-9, 2009
Hoffmann et al., *Biochemistry.* 36(26):8114-24, 1997
Holmes et al., *Proc Nat Acad Sci USA.* 111(41):E4376-85, 2014
Iba et al., *Acta Neuropathol.* 130(3):349-62, 2015
Iba et al., *J Neurosci.* 33(3):1024-37, 2013
Julien et al., *Methods Mol Biol.* 849:473-91, 2012
Kabsch, *Acta Crystallogr D Biol Crystallogr.* 66(Pt 2):125-32, 2010
Knappik et al., *J Mol Biol.* 296:57-86, 2000
Knight et al., *Platelets.* 15:409-18, 2004
Kohler and Milstein, *Nature.* 256:495-7, 1975
Krebs et al., *J Immunol Methods.* 254:67-84, 2001
Lee et al., *Cell Rep.* 16(6):1690-700, 2016
Lefranc et al., *Dev Comp Immunol.* 27:55-77, 2003
Leong et al., *Cytokine.* 16:106-19, 2001
Li and Lee, *Biochemistry.* 45(51):15692-701, 2006
Liu et al., *Brain Imaging Behav.* 6(4):610-20, 2012
Lonberg et al., *Nature.* 368:856-9, 1994
Malia et al., *Proteins.* 84:427-434, 2016
Martin and Thornton, *J Mol Biol.* 263(5):800-15, 1996
Matsuo et al., *Neuron.* 13(4):989-1002, 1994
McCoy et al., *J Appl Crystallogr.* 40(Pt 4):658-674, 2007
McEwan et al., 2017, *PNAS* 114(3):574-9

Mendez et al., *Nat Genet.* 15:146-56, 1997
Mercken et al., *Acta Neuropathol.* 84(3):265-72, 1992
Mercken, Ph.D. Thesis: University of Antwerp, Wilrijk-Antwerp, 1991
Mocanu et al., *J Neurosci.* 28(3):737-48, 2008
Morris et al., *Nat Neurosci.* 18(8):1183-9, 2015
Morris et al., *Neuron,* 70:410-26, 2011
Murshudov et al., *Acta Crystallogr D Biol Crystallogr.* 53(Pt 3):240-55, 1997
Oddo et al., *J Neurochem.* 102(4):1053-63, 2007
Otvos et al., *J Neurosci Res.* 39(6):669-73, 1994
Padlan et al., *Mol. Immunol.* 28:489-98, 1991
Peeraer et al., *Neurobiol Dis.* 73:83-95, 2015
Queen et al., *Proc Natl Acad Sci USA.* 86:10029-33, 1989
Scattoni et al., *Behav Brain Res.* 208(1):250-7, 2010
Schroeder et al., *J Neuroimmune Pharmacol.* 11(1):9-25, 2016
Seubert et al., *J Biol Chem.* 270(32):18917-22, 1995
Shi et al., *J Mol Biol.* 397:385-96, 2010
Strohl, *Curr Opin Biotechnol.* 20:685-91, 2009
Terwel et al., *J Biol Chem.* 280(5):3963-73, 2005
Wischik et al. *Proc Natl Acad Sci USA.* 85:4884-8, 1988
Wu and Kabat, *J Exp Med.* 132:211-50, 1970
Yang et al., *Protein Eng.* 16:761-70, 2003
Yoshiyama et al., *Neuron.* 53(3):337-51, 2007
Zhao et al., *Protein Expr Purif.* 67(2):182-9, 2009

We claim:

1. An isolated monoclonal antibody or antigen-binding fragment thereof that binds to a phosphorylated tau protein, comprising:
   (a) a $V_H$ having the polypeptide sequence of SEQ ID NO: 26 and a VL having the polypeptide sequence of SEQ ID NO: 31;
   (b) a $V_H$ having the polypeptide sequence of SEQ ID NO: 28 and a VL having the polypeptide sequence of SEQ ID NO: 34;
   (c) a $V_H$ having the polypeptide sequence of SEQ ID NO: 26 and a VL having the polypeptide sequence of SEQ ID NO: 34;
   (d) a $V_H$ having the polypeptide sequence of SEQ ID NO: 28 and a VL having the polypeptide sequence of SEQ ID NO: 31;
   (e) a $V_H$ having the polypeptide sequence of SEQ ID NO: 27 and a VL having the polypeptide sequence of SEQ ID NO: 31;
   (f) a $V_H$ from a heavy chain of SEQ ID NO: 74 and a $V_L$ from a light chain of SEQ ID NO: 75;
   (g) a $V_H$ from a heavy chain of SEQ ID NO: 76 and a $V_L$ from a light chain of SEQ ID NO: 77; or
   (h) a $V_H$ from a heavy chain of SEQ ID NO: 78 and a $V_L$ from a light chain of SEQ ID NO: 79.

2. The isolated monoclonal antibody or antigen-binding fragment of claim 1 comprising a heavy chain having a polypeptide sequence at least 95% identical of any of SEQ ID NOs: 45, 74, 76 and 78, and a light chain having a polypeptide sequence at least 95% identical to any of SEQ ID NOs: 46, 75, 77 and 79.

3. The isolated monoclonal antibody or antigen-binding fragment of claim 2 comprising a heavy chain having a polypeptide sequence of any of SEQ ID NOs: 45, 74, 76 and 78, and a light chain having a polypeptide sequence of any of SEQ ID NOs: 46, 75, 77 and 79.

4. The isolated monoclonal antibody or antigen-binding fragment of claim 3 comprising:
   (a) a heavy chain of SEQ ID NO: 45, and a light chain of SEQ ID NO: 46;
   (b) a heavy chain of SEQ ID NO: 74, and a light chain of SEQ ID NO: 75;
   (c) a heavy chain of SEQ ID NO: 76, and a light chain of SEQ ID NO: 77; or
   (d) a heavy chain of SEQ ID NO: 78, and a light chain of SEQ ID NO: 79.

5. The isolated monoclonal antibody or antigen-binding fragment of claim 1, comprising a human heavy chain IgG1 constant region and a human light chain kappa constant region.

6. An isolated nucleic acid encoding the monoclonal antibody or antigen-binding fragment of claim 1.

7. A vector comprising the isolated nucleic acid of claim 6.

8. A host cell comprising the nucleic acid of claim 7.

9. A pharmaceutical composition comprising the isolated monoclonal antibody or antigen-binding fragment of claim 1 and a pharmaceutically acceptable carrier.

10. A method of reducing pathological tau aggregation or spreading of tauopathy in a subject in need thereof, comprising administering to the subject the pharmaceutical composition of claim 9.

11. The method of claim 10, wherein the tauopathy is selected from the group consisting of familial Alzheimer's disease, sporadic Alzheimer's disease, frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica (boxing disease).

12. A method of producing the monoclonal antibody or antigen-binding fragment of claim 1, comprising culturing a cell comprising a nucleic acid encoding the antibody or antigen-binding fragment under conditions to produce the antibody or antigen-binding fragment, and recovering the antibody or antigen-binding fragment from the cell or cell culture.

13. A method of detecting the presence of PHF-tau in a biological sample from a subject, comprising contacting the biological sample with the antibody or antigen-binding fragment of claim 1, and detecting binding of the antibody or antigen-binding fragment to PHF-tau in the sample from the subject.

14. The method of claim 13 wherein the biological sample is a blood, serum, plasma, interstitial fluid, or cerebral spinal fluid sample.

* * * * *